(12) United States Patent
Bresnick

(10) Patent No.: US 11,116,620 B1
(45) Date of Patent: Sep. 14, 2021

(54) IMPLANT DELIVERY DEVICE WITH BIOFILM PROTECTION SHIELD

(71) Applicant: Stephen David Bresnick, Encino, CA (US)

(72) Inventor: Stephen David Bresnick, Encino, CA (US)

( * ) Notice: Subject to any disclaimer, the term of this patent is extended or adjusted under 35 U.S.C. 154(b) by 0 days.

(21) Appl. No.: 17/118,422

(22) Filed: Dec. 10, 2020

Related U.S. Application Data

(60) Provisional application No. 62/946,376, filed on Dec. 10, 2019, provisional application No. 63/066,760, filed on Aug. 17, 2020.

(51) Int. Cl.
*A61F 2/12* (2006.01)
*A61F 2/00* (2006.01)

(52) U.S. Cl.
CPC .............. *A61F 2/0095* (2013.01); *A61F 2/12* (2013.01)

(58) Field of Classification Search
CPC ................................ A61F 2/0095; A61F 2/12
See application file for complete search history.

(56) References Cited

U.S. PATENT DOCUMENTS

| | | | |
|---|---|---|---|
| 6,146,418 A | 11/2000 | Berman | |
| 8,206,443 B2 | 6/2012 | Preissman | |
| 8,211,173 B2 | 7/2012 | Keller et al. | |
| 8,315,700 B2 | 11/2012 | Citron et al. | |
| 8,409,279 B2 | 4/2013 | Freund | |
| 8,550,090 B2 | 10/2013 | Keller et al. | |
| 8,555,893 B2 | 10/2013 | Keller et al. | |
| 9,168,126 B2 | 10/2015 | Preissman | |
| 9,402,713 B2 | 8/2016 | Keller et al. | |
| 9,414,941 B2 | 8/2016 | Placik et al. | |
| 9,737,395 B2 | 8/2017 | Nguyen et al. | |
| 9,808,284 B2 | 11/2017 | Anderson | |
| 9,808,285 B2 | 11/2017 | Anderson | |
| 10,004,534 B2 | 6/2018 | Anderson | |
| 10,022,475 B2 | 7/2018 | Nguyen et al. | |

(Continued)

FOREIGN PATENT DOCUMENTS

WO 2018199929 A1 11/2018

*Primary Examiner* — Brian A Dukert
*Assistant Examiner* — Rebecca Lynee Zimmerman
(74) *Attorney, Agent, or Firm* — Polsinelli PC

(57) ABSTRACT

Devices, systems, and methods for delivering prosthesis implants into surgically-created implant pockets in a subject and for preventing capsular contracture resulting from surgical insertion of prosthesis implants. The device may include a delivery member operable to wrap around the implant thereby forming a conforming cavity around the implant that conforms to the shape of the implant. The delivery member is also operable to propel the implant from the conforming cavity into the implant pocket in the subject upon the application of mechanical force to the delivery member. The device also includes a shielding member coupled with the delivery member. The shielding member is operable to shield the implant from at least a portion of the dissection tunnel connecting the incision to the implant pocket during delivery of the implant to the implant pocket. The device is capable of shielding the implant from microbial contamination, including contamination by the endogenous flora of the subject, during delivery of the implant into the surgically-created implant pocket.

20 Claims, 31 Drawing Sheets

(56) References Cited

U.S. PATENT DOCUMENTS

| | | |
|---|---|---|
| 10,058,415 B2 | 8/2018 | Preissman |
| 10,092,385 B2 | 10/2018 | Anderson |
| 10,105,213 B2 | 10/2018 | Weinzweig |
| 10,136,988 B2 | 11/2018 | Keller et al. |
| 10,213,294 B2 | 2/2019 | Keller et al. |
| 2007/0276484 A1 | 11/2007 | Abell et al. |
| 2014/0228951 A1* | 8/2014 | Zochowski ............... A61F 2/12 623/8 |
| 2015/0297339 A1* | 10/2015 | Placik ................... A61F 2/0095 623/8 |

* cited by examiner

IMPLANT DELIVERY DEVICE WITH BIOFILM PROTECTION SHIELD

CROSS-REFERENCE TO RELATED APPLICATIONS

This application claims the benefit of U.S. Provisional Application Ser. No. 62/946,376, entitled "Biofilm Protection Implant Shield," filed Dec. 10, 2019, and U.S. Provisional Application Ser. No. 63/066,760, entitled "Implant Delivery Device with Biofilm Protection Shield," filed Aug. 17, 2020, the contents of each of which are incorporated by reference herein, for all purposes, in their entirety.

FIELD OF TECHNOLOGY

The present disclosure is directed to the insertion of prosthesis implants into a surgically-created implant pocket of a subject. In some specific instances, the present disclosure is directed to the insertion of breast implants, including un-filled implants and pre-filled implants such as silicone breast implants and pre-filled saline implants. The present disclosure is further directed to methods, devices, and systems for inserting prosthesis implants in the surgically-created implant pocket of a subject as well as methods for preventing capsular contracture resulting from surgical insertion of prosthesis implants.

BACKGROUND

Capsular contracture remains the most common complication of aesthetic breast augmentation despite advances in the understanding of the biological processes which appear to be involved. Capsular contracture is characterized by the tightening and hardening of the capsule surrounding the implant. The role of biofilms in capsular contracture has been reported extensively and is believed to play an important role in the pathogenesis of capsular contracture. Recent advances in antibiotic irrigation as well as the use of skin barriers and nipple shields has assisted in the reduction of capsular contracture. Yet, despite these advances, a significant number of women develop capsular contracture following breast augmentation and require revisional surgery or live with discomfort, deformity, or suboptimal results.

Form-stable implant studies with textured devices have shown lower capsular contracture rates compared to smooth round devices. However, anaplastic large cell lymphoma (ALCL) is an indolent lymphoma found in women with textured implants. Biofilm infection is hypothesized to be involved in the development of both capsular contracture and ALCL. It is suspected that a source of the biofilm infection may be microbes from the skin and/or exposed breast tissue of the patient that come in contact with the sterile implant during insertion into the surgically-created implant pocket. In particular, the subject's endogenous flora present at the time of the surgery, including those bacteria that may be present in the dissection tunnel connecting the skin incision to the surgically-created implant pocket or the skin surface itself, may attach to the surface of the implant during placement in the implant pocket. Following insertion of the implant, the bacteria may colonize the surface of the implant and form a biofilm. If the surface of the implant is colonized by a large number of bacteria, the subject's defenses may be overwhelmed and the biofilm may trigger a chronic inflammatory response leading to subsequent fibrosis and accelerated capsular contracture. Accordingly, methods and devices capable of shielding the implant from microbial contamination, including contamination by the endogenous flora of the subject, during delivery and insertion of the implant into the surgically-created implant pocket are desirable.

BRIEF DESCRIPTION OF THE DRAWINGS

In order to describe the manner in which the advantages and features of the disclosure can be obtained, reference is made to embodiments thereof which are illustrated in the appended drawings. One of skill in the art will understand that the reference numbers in the following figures are repeated throughout FIGS. 1-39 so as to refer to the same or substantially the same features. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
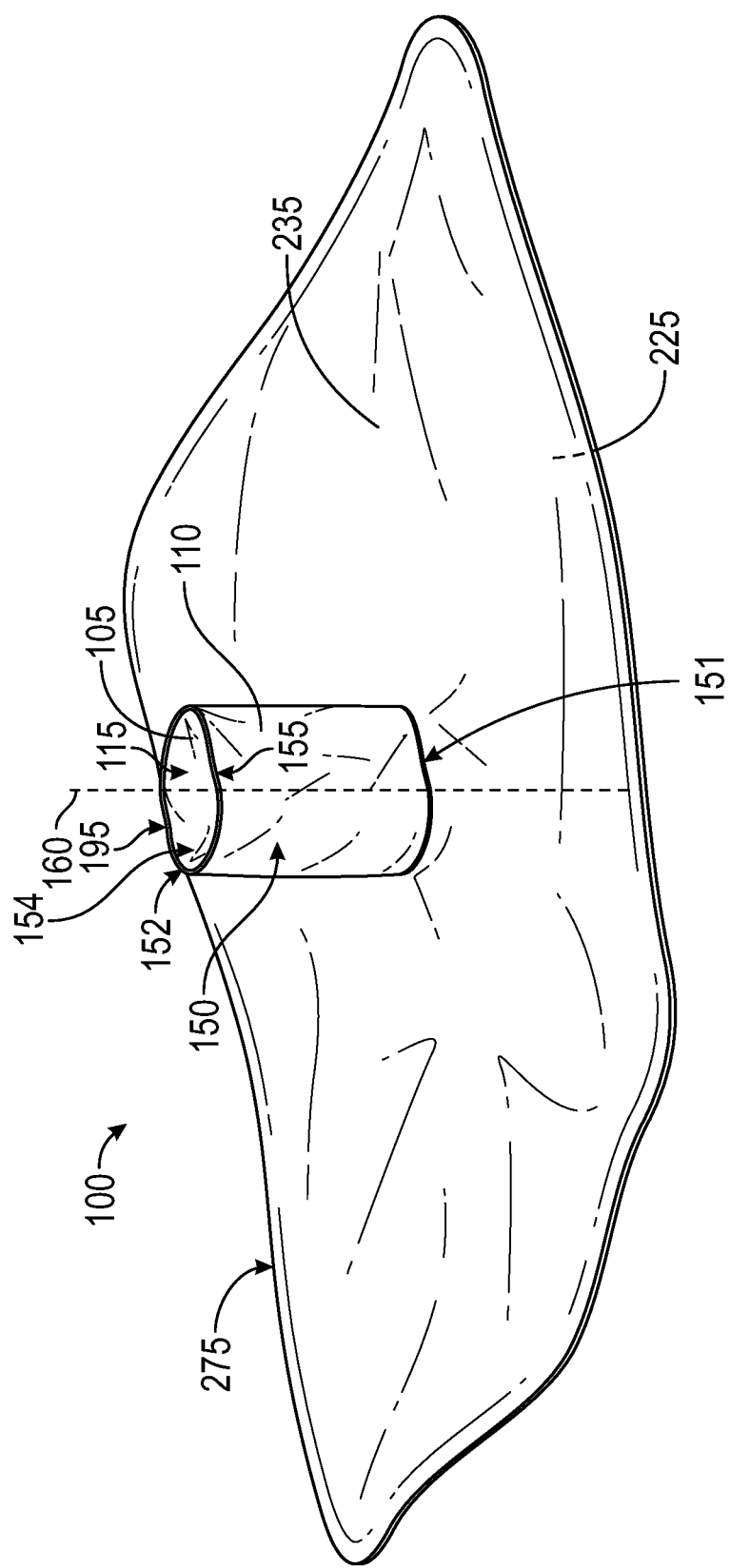
FIG. 1 is an isometric view of an implant delivery device with biofilm protection shield having a substantially rectangular-shaped delivery member and a shielding member, according to an exemplary embodiment of the present disclosure.

It will be appreciated that numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein.

The present disclosure provides apparatus, methods, and systems for inserting prosthesis implants into surgically-created implant pockets in a subject. The presently disclosed apparatus, methods, and systems may be used to deliver any prosthesis implants into a surgically-created implant pocket in a subject. The present disclosure is further directed to methods, devices, and systems for preventing capsular contracture resulting from surgical insertion of prosthesis implants. The prosthesis implant may include, for example, filled implants or pre-filled implants, unfilled implants, saline implants, silicone gel implants, textured implants, smooth implants, highly cohesive silicone gel implants, or oil-filled implants. The prosthesis implant may also be, for example, an implantable device, such as a pacemaker or a joint replacement prosthesis, or the prosthesis implant may be a tissue graft, such as an allograft or an autograft.

In some specific instances, the present disclosure is directed to the insertion of breast implants into the implant pocket in a breast of a subject. In such cases, the breast implant may be an un-filled breast implant or may be a pre-filled breast implant such as a pre-filled saline implant or a pre-filled silicone implant. In particular, the presently disclosed apparatus, methods, and systems are well-suited to the delivery of pre-filled breast implants which require an insertion device capable of withstanding and managing the compressive and frictional forces associated with insertion of the pre-filled implant while still being gentle enough so as to not damage the pre-filled implant during delivery to the implant pocket in the subject. The breast implant may also be, for example, a textured breast implant, a smooth breast implant, a highly cohesive silicone gel breast implant, an oil-filled breast implant, or an un-filled saline breast implant. The present disclosure is further directed to methods, devices, and systems for preventing capsular contracture resulting from surgical insertion of breast implants.

According to at least one aspect of the present disclosure, an implant delivery device having a biofilm protection implant shield useful for delivering an implant into a surgically-created implant pocket in a subject is provided. The implant delivery device may include a delivery member operable to wrap around and tightly contour to the implant and facilitate sterile delivery of the implant by propelling the implant into the implant pocket of a subject upon application of mechanical force to the delivery member. The implant delivery device may also include a shielding member for shielding the implant from at least a portion of the dissection tunnel during delivery of the implant into the implant pocket in the subject. The application of mechanical force to the lower surface of the delivery member imparts a compressive force on the delivery member above the implant (e.g., between the proximal end of the delivery member and the conforming cavity) so as to propel the implant from the delivery member and into the shielding member and into the implant pocket of the subject.

The delivery member of the implant delivery device is operable to wrap around an implant placed on the upper surface of the delivery member, thereby forming a cavity or pocket around the implant that conforms to the shape of the implant. Because the delivery member is operable to conform to the shape of the implant as it is tightly wrapped around the implant, the delivery member is able to be used with any size implant and implants of any shape or dimension including, for example, highly round implants, moderately round implants, substantially flat implants, and teardrop shaped implants. Therefore, unlike many conventional implant delivery systems that are pre-formed and therefore only suitable for use with only a particular implant size or a narrow range of implant sizes or shapes, the presently disclosed implant delivery device may be used to deliver an implant of any specification, dimension, or shape. Additionally, the presently disclosed implant delivery device includes a shielding member for shielding the implant from dissection tunnel flora that is not found in other implant delivery devices.

In further contrast with other implant delivery devices, the presently disclosed implant delivery device may be used just as a delivery device or just as a biofilm implant shield or as both a delivery device and biofilm implant shield depending upon user preference or situation. For example, the implant delivery device may be used as a biofilm implant shield with or without a separate implant delivery device by inserting the shielding member into the incision and dissection tunnel to a depth greater than 1 cm below the incision and allowing the lower surface of the delivery member to engage the skin of the subject adjacent to the incision or otherwise lay flat against the skin of the subject. In such instances, the implant may be inserted into the inner bore of the shielding member by hand or by using a separate implant delivery device thereby shielding the implant from the flora of the dissection tunnel during delivery to the implant pocket.

Additionally, two of the presently disclosed implant delivery devices may be used together, in conjunction, in order to facilitate both the delivery and shielding functions during implant delivery and insertion. In such cases, a first implant delivery device is used as a biofilm implant shield by inserting the shielding member into the incision and dissection tunnel to a depth greater than 1 cm below the incision and allowing the lower surface of the delivery member to engage the skin of the subject adjacent to the incision or otherwise lay flat against the skin of the subject. Subsequently, a second implant delivery device is wrapped around an implant according to the presently disclosed techniques so as to load the implant into the conforming cavity of the delivery member. The distal end of the shielding member of the second implant delivery device may then be inserted into the aperture of the first implant delivery device and mechanical force applied to the lower surface of the delivery member of the second implant delivery device in order to cause the implant to translate from the conforming cavity through the inner bore of the shielding member of the second implant delivery device and into the aperture and shielding member of the first implant delivery device, thereby providing for sterile delivery of the implant to the implant pocket in the subject.

Alternatively, the implant delivery device may be used as an implant delivery device without taking full advantage of the shielding capabilities of the shielding member. In such instances, the shielding member may be inserted into the incision only to a depth sufficient for delivery of the implant to the implant pocket, generally less than or equal to 1 cm below the incision. The application of mechanical force to the delivery member may then be used to propel or force the implant from the cavity formed by the delivery member and through the inner bore of the shielding member and into the implant pocket.

In other instances, the implant delivery device may be used as both an implant delivery device and a biofilm implant shield as described throughout the present disclosure.

The shielding member and the delivery member may be formed from a flexible material. In at least some instances, it is preferred that the delivery member and/or the shielding member are made of a transparent or translucent material. The delivery member and the shielding member may be made from the same or different materials. In at least some instances, the delivery member is made of a pliable material that is resistant to stretching or that is fairly inelastic to mildly elastic, while the shielding member is made of a different material that is characterized by a higher degree of stretchability or elasticity so that it may conform to the walls of the dissection tunnel. It is generally important that the delivery member be made of a material that is flexible, strong and capable of slightly stretching without breaking. In at least some instances, the delivery member may be made of a PVC material mixed with a DEHP plasticizer, ethyl vinyl acetate, or a polyolefin such a polypropylene. In some instances, the delivery member and/or the shielding member may be made of a flexible material that may be selected from the group consisting of plastic-containing fabrics, polymers, plastics, ethylene-vinyl acetate (EVA), polyethylene terephthalate (e.g., mylar), vinyls, polyvinyl chloride, ethylene and alpha-olefin copolymers, silicone, solid silicone, silicone rubber, and any combination thereof.

The shielding member of the implant delivery device is operable to shield the implant from at least a portion of the dissection tunnel during delivery of the implant into the implant pocket in the subject. In some instances, the implant delivery device may optionally include a base that helps to secure the shielding member during delivery of the implant into the shielding member and the implant pocket.

The shielding member has an inner bore extending longitudinally between a proximal end and a distal end. The inner bore extends a predetermined length between the proximal end and the distal end of the shielding member. The inner bore of the shielding member may be tubular, conical, or any combination thereof. In cases in which the inner bore of the shielding member is tubular, the inner bore of the shielding member has an uniform cross-sectional width along its predetermined length. In cases in which the inner bore of the shielding member is conical, the inner bore of the shielding member has a variable cross-sectional width along its predetermined length. Typically, the conical shielding member has a wider cross-sectional width towards the proximal end of the conical shielding member. For example, the shielding member may comprise a conical member in which the cross-sectional width of the inner bore at the proximal end of the shielding member is longer than the cross-sectional width of the inner bore at the distal end of the shielding member. In such cases, the wider cross-section width the proximal end of the shielding member may facilitate or ease insertion of the implant into the shielding member.

In some instances, the shielding member may have an inner bore that is both tubular and conical. In such instances, the shielding member may comprise a tubular member and a conical member. Generally, the conical member comprises the proximal end of the shielding member while the tubular member comprises the distal end of the shielding member. Accordingly, the proximal end of the inner bore of the shielding member may have a variable cross-sectional width while the distal end of the inner bore has an uniform cross-sectional width.

The implant delivery device may optionally include a base that helps to secure the shielding member during delivery of the implant into the inner bore of the shielding member and ultimately to the implant pocket of the subject. The base has an upper surface and a lower surface. The lower surface of the base is operable to substantially engage with at least a portion of the skin adjacent to an incision leading to the implant pocket. The base may have an aperture formed therein which extends through the upper surface and the lower surface of the base. The base may be coupled to the proximal end of the shielding member such that the proximal end of the inner bore of the shielding member is substantially aligned with the aperture formed in the base. The aperture formed in the base is also co-aligned with the aperture formed in the delivery member thereby forming a collective aperture through which the implant may pass when mechanical force is applied to the delivery member.

The base and the delivery member extend away from the collective aperture and are detachably coupled along the radial length of the delivery member so that the base and the delivery member may be peeled apart. However, the base and the delivery member maintain a coupling along the circumference of the collective aperture. In at least some instances, the base and the delivery member are heat sealed together along the circumference of the collective aperture. Therefore, when an implant is disposed in the conforming cavity or pocket of the delivery member and mechanical force is applied to the delivery member, the implant may be squeezed from the conforming cavity and through the collective aperture formed into the delivery member and base and into the proximal end of the inner bore of the shielding member.

According to at least one aspect of the present disclosure, an implant delivery device for delivering an implant into a surgically-created implant pocket in a subject is provided. The device may include a delivery member having an upper surface and a lower surface. The delivery member may have an aperture formed therein that extends through the upper surface and the lower surface of the delivery member. The device may also include a shielding member coupled with the delivery member. The shielding member may have an inner bore extending longitudinally between a proximal end and a distal end, the inner bore extending a predetermined length away from the lower surface of the delivery member. The proximal end of the shielding member may be coupled with the delivery member and the inner bore may be substantially aligned with the aperture formed in the delivery member. The inner bore of the shielding member is operable to receive the implant therethrough. The shielding member may have an aperture formed in the distal end of the shielding member through which the implant exits the shielding member and is received by the implant pocket of the subject.

In at least some instances, the lower surface of the delivery member is operable to engage with a skin of the subject in order to facilitate use of device for just an implant shielding use without using the device as a delivery device. In such instances, the delivery member may engage with the skin of the subject adjacent to the incision and provide stability and support for the shielding member during insertion of the implant into the inner bore of the shielding member. In some instances, the delivery member may have an adhesive disposed on the lower surface of the delivery member.

In at least some instances, the inner bore of the shielding member may be conical or frustoconical. The inner bore may have a larger cross-sectional width at the proximal end than the cross-sectional width of the inner bore at the distal end of the shielding member. In some instances, the inner bore may include both a conical portion and a tubular portion along its predetermined length.

In some cases, the shielding member may include a conical member. In such cases, the proximal end of the conical member may be coupled with the lower surface of the delivery member such that the inner bore of the conical member is substantially aligned with the aperture of the delivery member so that the conical member may receive the implant once the implant is delivered from the conforming cavity formed by the delivery member and through the aperture upon application of mechanical force to the delivery member.

In other cases, the shielding member may include both a conical member and a tubular member. In such cases, the conical member may have an inner bore, a distal end, and a proximal end, and the tubular member may have an inner bore, a distal end and a proximal end. The distal end of the conical member may be coupled with the proximal end of the tubular member such that the inner bore of the conical member is substantially aligned with the inner bore of the tubular member to form the inner bore of the shielding member. The tubular member may have a first predetermined length and the conical member may have a second predetermined length, the predetermined length of the shielding member comprising the sum of the first and second predetermined lengths.

The shielding member may have an outer surface that defines the outer bore of the shielding member. In some instances, the outer bore may be substantially tubular and the inner bore may be substantially frustoconical. In such cases, the outer bore may have a cross-sectional width that is substantially tubular and the inner bore may have a cross-sectional width that is substantially frustoconical. In other instances, the outer bore may be substantially tubular and the inner bore may include a tubular portion and a conical portion. In such instances, the tubular portion of the inner bore may include a substantially uniform cross-sectional width and the conical portion of the inner bore may include a larger cross-sectional width that is larger at the proximal end of the shielding member and decreases towards the distal end of the shielding member. In still other cases, the inner bore may have a substantially uniform cross-sectional width over the predetermined length.

According to at least one aspect of the present disclosure, an implant delivery device for delivering an implant into a surgically-created implant pocket in a subject is provided. The device may include a delivery member having an upper surface and a lower surface. The delivery member may have an aperture formed therein which extends through the upper surface and the lower surface of the delivery member. The device may also include a shielding member that is coupled to the delivery member. The shielding member may have an inner bore extending longitudinally between a proximal end and a distal end. The inner bore may extend a predetermined length away from the lower surface of the delivery member. The proximal end of the shielding member may be coupled with the delivery member and the inner bore may be substantially aligned with the aperture formed in the delivery member. The inner bore of the shielding member may be operable to receive the implant. In some instances, the shielding member may be tubular and have a substantially uniform cross-sectional width over the predetermined length of the shielding member. In such instances, the shielding member may be a tubular shielding member or otherwise comprise a tubular member.

According to another aspect of the present disclosure, an implant delivery device for delivering an implant into a surgically-created implant pocket in a subject is provided. The implant delivery device includes a delivery member having an upper surface and a lower surface. The implant delivery device also includes a shielding member extending through the delivery member. The shielding member has an inner bore, a proximal end and a distal end. The inner bore of the shielding member extends longitudinally a predetermined length away from the lower surface of the delivery member and between the proximal end and the distal end. The inner bore is operable to receive an implant therethrough. In some cases, the shielding member may be tubular and have a substantially uniform cross-sectional width over the predetermined length. In such instances, the shielding member may be a tubular shielding member or otherwise comprise a tubular member.

In at least some cases, the shielding member may be tubular. The inner bore of the shielding member may have a substantially uniform cross-sectional width over the predetermined length. The predetermined length may be, for example, greater than 1 cm or may be from about 2 cm to about 10 cm. The shielding member includes an outer surface and an inner surface, wherein the inner surface of the shielding member defines the inner bore of the shielding member.

The delivery member is operable to shield the implant from the skin of the patient during delivery of the implant into the implant pocket of the subject. Additionally, the shielding member is operable to shield the implant from at least a portion of a dissection tunnel connecting an incision on a skin of the subject and the implant pocket. The delivery member may be further operable to mechanically propel the implant through the inner bore of the shielding member and out the distal end of the shielding member upon the application of mechanical force to the lower surface of the delivery member.

In some instances, the implant delivery device may further include a base that extends radially from the shielding member. In some instances, the base may extend radially from an intersection of the shielding member and the delivery member. The base may include an upper surface and a lower surface, the lower surface being operable to engage a skin of the subject. In at least some instances, the base may be integrally formed with the delivery member and shielding member. The shielding member, the base, and the delivery member may be formed from a flexible material. For example, the flexible material may be selected from the group consisting of plastic-containing fabrics, polymers, plastics, ethylene-vinyl acetate (EVA), polyethylene terephthalate (e.g., mylar), vinyls, polyvinyl chloride, ethylene and alpha-olefin copolymers, silicone, solid silicone, silicone rubber, and any combination thereof.

The presently disclosed implant delivery device may also be used to prevent capsular contracture in a subject resulting from surgical insertion of a breast implant in a surgically-created implant pocket through a dissection tunnel connecting the implant pocket to an incision on the skin of the subject. The implant delivery device is capable of shielding the implant from microbial contamination, including contamination by the endogenous flora of the subject, during insertion of the implant into the surgically-created implant pocket.

According to at least one aspect of the present disclosure, a system is provided. The system includes an implant delivery device for inserting an implant into a surgically-created implant pocket in a subject as described herein. The system further includes an implant that may be inserted by the implant delivery device.

According to at least one aspect of the present disclosure, a kit is provided. The kit may include an implant delivery device for inserting an implant into a surgically-created implant pocket in a subject, as described herein. Packaged together with the implant delivery device, the kit may further include an implant that may be inserted by the implant delivery device. According to another aspect, the kit may include an implant delivery device and a sterile bowl that facilitates loading of the implant delivery device, as described and shown in FIGS. 38-39. In particular, the kit may include an implant delivery device disposed in a sterile bowl and sealed in sterile packaging. In some instances, the kit may include two bowls, such as the double bowl sterile packing used for breast implants. The kit may also include sterile barrier dressing, such as a plastic sterile barrier dressing. The kit may also include a separate lubricant that may be applied to the shielding member and/or the delivery member of the implant delivery device.

According to at least one aspect of the present disclosure, a device for delivering an implant into a surgically-created implant pocket in a subject is provided. The device may include a delivery member having an upper surface and a lower surface. The delivery member may further have an aperture formed therein and extending through the upper surface and the lower surface. The device may also include a shielding member coupled with the delivery member. The shielding member may have an inner bore extending longitudinally between a proximal end and a distal end. The inner bore may extend a predetermined length away from the lower surface of the delivery member. The proximal end of the shielding member may be coupled with the delivery member and the inner bore may be substantially aligned with the aperture formed in the delivery member. The delivery member is operable to wrap around the implant to form a conforming cavity around the implant that conforms to the shape of the implant. The inner bore is operable to receive the implant therethrough when mechanical force is applied to the lower surface of the delivery member. Therefore, the delivery member is operable to propel the implant from the conforming cavity into the implant pocket in the subject upon the application of mechanical force to the lower surface of the delivery member.

According to another aspect of the present disclosure, a method for delivering an implant into a surgically-created implant pocket in a subject through a dissection tunnel connecting the implant pocket to an incision on the skin of the subject is provided. The method may include providing a sterile implant delivery device. The implant delivery device may include a delivery member having an upper surface and a lower surface, the delivery member having an aperture formed therein and extending through the upper surface and the lower surface. The implant delivery device used in the method may also include a shielding member coupled with the delivery member, the shielding member having an inner bore extending longitudinally between a proximal end and a distal end. The inner bore may extend a predetermined length away from the lower surface of the delivery member. The method may further include causing the delivery member to wrap around the implant to form a conforming cavity around the implant that conforms to the shape of the implant. The method may also include inserting, while the implant is disposed within the conforming cavity formed by the delivery member, the distal end of the shielding member of the implant delivery device through the incision in the skin of subject and into the dissection tunnel such that the distal end of the shielding member is received in at least a portion of the dissection tunnel. The method may also include causing, by the application of mechanical force to the lower surface of the delivery member, the implant to translate from the conforming cavity through the aperture formed in the delivery member and into the inner bore of the shielding member and into the implant pocket in the subject. The method may be used to prevent capsular contracture in a subject resulting from surgical insertion of a breast implant in a surgically created implant pocket through a dissection tunnel connecting the implant pocket to an incision on the skin of the patient.

FIG. 1 depicts an isometric view of an implant delivery device 100 for delivering an implant into a surgically-created implant pocket in a subject, according to an exemplary embodiment of the present disclosure. As depicted in FIG. 1, implant delivery device 100 may include a delivery member 275 having an upper surface 225 and a lower surface 235. The implant delivery device 100 includes an aperture 220 (not shown in FIG. 1; see FIG. 4) formed in the delivery member 275 and extending through the upper surface 225 and the lower surface 235.

Implant delivery device 100 further includes a shielding member 150 coupled with the delivery member 275. The shielding member 150 has an inner surface 105, an outer surface 110, a proximal end 151 and a distal end 152. The proximal end 151 has a proximal opening 153 and the distal end 152 has a distal opening 154. As depicted in FIG. 1, the proximal end 151 is coupled with the delivery member 275 while the distal end 152 of shielding member 150 extends away from the delivery member 275. The shielding member 150 has an inner bore 115 defined by inner surface 105. The outer surface 110 defines an outer bore 195 of shielding member 150 that includes the cross-sectional width of the inner bore 115 as well as the thickness of the wall of the shielding member 150 at the particular portion of along the outer surface 110 that the outer bore 195 is determined. The distal end 152 of the shielding member 150 has an aperture 155 that is substantially aligned with inner bore 115 and aperture 220 of the delivery member 275 when the shielding member 150 is extended. As shown in FIG. 1, the inner bore 115 has a longitudinal axis 160 extending therethrough. The longitudinal axis 160 extends substantially perpendicular to the delivery member 275. The inner bore 115 extends longitudinally along the longitudinal axis 160 between the proximal end 151 and the distal end 152 a predetermined length 165 (not shown in FIG. 1; see FIG. 2) away from the lower surface 235 of the delivery member 275. Therefore, the shielding member 150 also extends along the longitudinal axis 160 and substantially orthogonally from the delivery member 275.

As depicted in FIG. 1, the delivery member 275 extends away from shielding member 150 in a direction substantially perpendicular to the longitudinal axis 160. The inner bore 115 is substantially aligned with the aperture 220 formed in the delivery member 275. In at least some instances, the delivery member 275 extends away from shielding member 150 in substantially the same plane as the aperture 220. The aperture 220 and inner bore 115 of shielding member 150 are operable to receive the implant. The proximal end 151 of shielding member 150 is also operable to receive an implant therethrough. The distal end 152 of shielding member 150 is operable to be inserted into an incision in the skin of the subject and further operable to be extended the predetermined length 165 such that the distal end 152 is received into at least a portion of the surgically-created implant pocket or a distal portion of the dissection tunnel connecting an incision in the skin of the subject to the implant pocket. In some instances, at least a portion of the inner bore 115 of the shielding member 150 may extend a second predetermined length above the upper surface 225 of the delivery member 275 (not shown in FIGS. 1-4).

The shielding member 150 of implant delivery device 100 is operable to extend along at least a portion of the dissection tunnel during use. The shielding member 150 is also operable to deliver the implant to the implant pocket or a distal portion of the dissection tunnel without the implant contacting the incision site or at least a portion of the dissection tunnel. In some instances, the shielding member 150 of apparatus 100 may be operable to shield the implant from touching any portion of the dissection tunnel or incision site.

While FIGS. 1-4 depict shielding member 150 as having an inner bore 115 that is tubular with a substantially uniform cross-sectional width 157 along its predetermined length 165 (refer to FIG. 2), the shielding member 150 may have an inner bore 115 that is tubular, conical, or any combination thereof. In cases in which the inner bore 115 of the shielding member 150 is tubular, the inner bore 115 of the shielding member 150 has an uniform cross-sectional width 157 along its predetermined length 165. In cases in which the inner bore 115 of the shielding member 150 is conical, the inner bore 115 of the shielding member 150 has a variable cross-sectional width 157 along its predetermined length 165. Typically, if the shielding member 150 has a inner bore 115 that is conical, the inner bore 115 has a wider cross-sectional width 157 towards the proximal end 151 of the shielding member 150. For example, the cross-sectional width 157 of the inner bore 115 at the proximal end 151 of the shielding member 150 may be longer than the cross-sectional width 157 of the inner bore 115 at the distal end 152 of the shielding member 150. In such cases, the wider cross-section width 157 at the proximal end 151 of the shielding member 150 may facilitate or ease insertion of the implant into the shielding member 150.

In some instances, the shielding member 150 may have an inner bore 115 that is both tubular and conical. In such instances, the shielding member 150 may comprise a tubular member and a conical member. When the shielding member 150 has an inner bore 115 that is both tubular and conical, the conical member generally comprises the proximal end 151 of the shielding member 150 while the tubular member comprises the distal end 152 of the shielding member 150. Accordingly, the proximal end 151 of the inner bore 115 of the shielding member 150 may have a variable cross-sectional width 157 while the distal end 152 of the inner bore 115 has an uniform cross-sectional width 157.

In at least some instances, the shielding member 150 and/or inner bore 115 of the shielding member 150 is substantially cylindrical in cross-sectional shape. In some instances, the shielding member 150 and/or inner bore 115 of the shielding member 150 may be elliptical in cross-sectional shape. In some cases, the inner bore 115 of shielding member 150 is not tapered along the predetermined length 165. In at least some instances, the distal end 152 has substantially the same cross-sectional width as the cross-sectional width of the proximal end 151. In such cases, the cross-sectional width 157 of the inner bore 115 at the distal end 152 of the shielding member is substantially the same as the cross-sectional width 157 of the inner bore at the proximal end 151 of the shielding member. In some cases, the aperture 155 of the distal end 152 of shielding member 150 has substantially the same cross-sectional width as the cross-sectional width of aperture 120 in base 175. In some cases, the cross-sectional width of the aperture 120 in base 175 may be substantially the same as the cross-sectional width 157 of the proximal end 151 of the inner bore 115 of the tubular member 150.

The cross-sectional width 157 of the inner bore 115 of the shielding member 150 may be any cross-sectional width suitable to receive and facilitate insertion of an implant into the implant pocket of a subject. For example, the cross-sectional width 157 of the inner bore 115 of the shielding member 150 may be from about 3 cm to about 12 cm, or from 3.5 cm to about 9 cm, or from about 3.5 cm to about 8.5 cm, or from about 5 cm to about 8 cm. In at least some instances, the cross-sectional width 157 of the inner bore 115 may be selected based on the size of the implant. In general, pre-filled breast implants are from about 9 cm to about 16 cm (most commonly from about 11 cm to about 12 cm) in diameter but deform and elongate when inserted into the aperture 220 and inner bore 115 of device 100.

As used herein, the term "cross-sectional width" shall include the longest distance between two points on the circumference or edge of the cross-section of an object having a circular and/or non-circular cross-section. The two points may be located on the interior or exterior surface circumference or edge of the cross-section of the object. It should be recognized that "cross-sectional width" of objects having a substantially circular cross-section may be referred to as the "diameter" of the object. The terms "cross-sectional width" and "diameter" may be used interchangeably for objects having a substantially circular cross-section. Understanding that the presently disclosed devices and apparatus, or portions thereof, may be deformable or collapsible or formed from collapsible or deformable materials, the cross-sectional width, as referred to herein, is generally measured in the open and/or extended configuration, such as that typical during use.

While FIGS. 1-4 depict the inner bore 115 of the shielding member 150 as substantially circular in cross-sectional profile, inner bore 115 may have any cross-sectional profile, including conical, elliptical, oval, or circular. Likewise, the outer bore 195 or outer profile of the shielding member 150, as defined by outer surface 110 of the shielding member 150, may be conical, elliptical, oval, or circular. In at least some instances the distal end 152 and the proximal end 151 of inner bore 115 have the same cross-sectional profile, wherein the cross-sectional profile is selected from the group consisting of circular, elliptical, and oval. For example, in cases in which the distal end 152 and the proximal end 151 of inner bore 115 have the same cross-sectional profile, the cross-sectional profile of both the distal end 152 and the proximal end 151 of inner bore 115 could have an elliptical cross-sectional profile, or both could have a circular cross-sectional profile, or both could have an elliptical cross-sectional profile. In other cases, the distal end 152 of inner bore 115 may have a cross-sectional profile that is different than the cross-sectional profile of the proximal end 151. For example, in such cases, the distal end 152 may have a cross-sectional profile that is elliptical while the proximal end 151 may have a circular cross-sectional profile. In cases in which the distal end 152 and the proximal end 151 of inner bore have different cross-sectional profiles, they may still have the substantially the same cross-sectional width. It should be recognized that when the cross-sectional profile of a portion of the inner bore 115 is circular, elliptical, or oval, the three-dimensional profile (e.g., the exterior profile or shape) of a corresponding portion of shielding member 150 may also be, respectively, circular, elliptical, or oval.

The delivery member 275 is operable to wrap around the implant to form a conforming cavity around the implant that conforms to the shape of the implant. The delivery member 275 is also operable to propel the implant from the conforming cavity through aperture 220 formed in the delivery member 275 and into the inner bore 115 of the shielding member 150 upon the application of mechanical force to the lower surface 235 of the delivery member 275. Therefore, delivery member 275 is operable to deliver the implant through the shielding member 150 and into the implant pocket of a subject thereby providing protected or no touch delivery and insertion of the implant to the implant pocket.

The shielding member 150 is operable to deliver the implant subdermally to the implant pocket, or a distal portion of the dissection tunnel, through the predetermined length 165 of inner bore 115 of the shielding member 150. In at least some instances, the predetermined length 165 may be determined based on a distance between an incision in the skin of a patient and a surgically-created implant pocket formed below the skin. In other cases, the predetermined length 165 may be based on a distance between an incision in the skin and the length of the dissection tunnel or portion of a dissection tunnel connecting the incision to the surgically-created implant pocket. In some instances, the predetermined length 165 between the proximal end 151 and the distal end 152 extends the inner bore 115 operably to deliver an implant subdermally through the aperture 120 and inner bore 115 and into the surgically-created implant pocket or a distal portion of the dissection tunnel or when the lower surface 235 of delivery member 275 is adjacently engaged with the skin of a subject and the distal end 152 is received into at least a portion of the implant pocket or distal portion of the dissection tunnel.

The predetermined length 165 of the inner bore 115 of the shielding member 150 may be adjusted based on the desired depth of insertion into the dissection tunnel, the size of the implant used, the location of the incision, and the characteristics of the subject's breast. In at least some instances, the predetermined length 165 of the inner bore 115 may have a predetermined length 165 equal to or less than the measured length of the dissection tunnel. In some instances, the predetermined length 165 of the inner bore 115 of the shielding member 150 may be greater than 1 cm, or greater than 1.5 cm, or greater than 2 cm, or greater than 2.5 cm, or greater than 3 cm, or greater than 3.5 cm, or greater than 4 cm, or greater than 4.5 cm, or greater than 5 cm, or greater than 5.5 cm, or greater than 6 cm, or greater than 6.5 cm, or greater than 7 cm, or greater than 7.5 cm, or greater than 8 cm. In other instances, the predetermined length 165 may be from about 2 cm to about 10 cm, or from about 3 cm to about 10 cm, or from about 2 cm to about 8 cm, or from about 2 cm to about 5 cm, or from about 3 cm to about 8 cm.

The implant delivery device 100, including shielding member 150 and delivery member 275, may be made of any suitable flexible material. For example, the flexible material may include, but is not limited to, plastic-containing fabrics, polymers, plastics, ethylene-vinyl acetate (EVA), polyethylene terephthalate (e.g., mylar), vinyls, polyvinyl chloride, ethylene and alpha-olefin copolymers, silicone, solid silicone, silicone rubber, and any combination thereof. In some cases, the shielding member 150 and delivery member 275 may be formed from the same material. In some instances, the flexible material may be resistant to stretching. In some instances, the shielding member 150 and the delivery member 275 may be integrally formed. In some instances, the flexible material may be a transparent or semi-transparent flexible material.

In other instances, implant delivery device 100, including shielding member 150 and delivery member 275, may be stretchable and/or made of a flexible material that is stretchable. As used herein, the term "stretchable" refers to a material, or property of a device or device component, that may be extensible or elastomeric. That is, a stretchable material, or a stretchable device or device component, may be extended, deformed, or the like, without breaking, and may or may not significantly retract after removal of an extending force. As used herein, the terms "elastomeric" or "elastic" are used interchangeably to refer to that property of a material (or device or device component) where upon removal of an elongating force, the material (or device or device component) is capable of recovering to substantially is unstretched size and shape or the material exhibits a significant retractive force. As used herein, the term "extensible" refers to that property of a material (or device or device component) where upon removal of an elongating force, the material (or device or device component) experiences a substantially permanent deformation or the material does not exhibit a significant retractive force.

In particular, shielding member 150 may be stretchable and/or comprise a stretchable material. Stretchability of the shielding member 150 provides the advantage that when retractors are placed inside of the shielding member 150 during use to open up the dissection tunnel, the shielding member 150 may stretch to allow greater opening of the dissection tunnel as well as engagement of the walls of the dissection tunnel thereby providing effective shielding for the implant as well as reducing the frictional forces associated with implant insertion. The stretchability of the shielding member 150 also provides the advantage of stretching during insertion of the implant so as to reduce the forces associated with implant insertion and to facilitate transit of the implant to the implant pocket while providing the implant shielding function, whether retractors are placed within shielding member 150 during use or not. In at least some instances, the shielding member 150 may be elastic or comprise an elastic material. In other instances, the shielding member 150 may be extensible or comprise an extensible material.

In at least some instances, the shielding member 150 may be made of a material that is different than the material that makes up the delivery member 275. For example, while it is advantageous in at least some instances that the shielding member be stretchable or made of a stretchable material, delivery member 275 does not necessarily need to be stretchable or made of a stretchable material. In other instances, delivery member 275 may comprise the same material as shielding member 150 but the stretchability of shielding member 150 is determined by the thickness of the material. In other words, shielding member 150 may be constructed of a material that is thin enough to be stretchable during use while the delivery member 275 may be constructed of the same material but may not be stretchable due to the chosen thickness of the delivery member 275.

In at least some instances, the delivery member 275 is formed from a vinyl or polyvinyl chloride while the shielding member 150 is formed from elastomeric silicone or silicone rubber. In other instances, both the delivery member 275 and the shielding member 150 may be formed from a vinyl or polyvinyl chloride or both the delivery member 275 and the shielding member 150 may be formed from elastomeric silicone or silicone rubber. In at least some instances, the delivery member 275 may be formed from a material that is fairly elastic to mildly elastic while the shielding member 150 may be formed from a material that is slightly stretchable to elastic. In at least some instances, the joint or intersection between the delivery member and the shielding member is heat sealed or sealed with a glue or adhesive.

In some cases, the inner bore 115 may include a lubricant along the inner surface 105 that defines the inner bore 115. In such cases, the lubricant along the inner surface 105 of the inner bore 115 may facilitate insertion and passage of the implant into and through aperture 120 and inner bore 115. In some instances, the outer surface 110 of the shielding member 150 may include a lubricant. In such cases, the lubricant on the outer surface 110 may facilitate insertion of the shielding member 150 into the dissection tunnel. The lubricant may be, for example, a sterile lubricant selected from the group consisting of a surgical lubricant, a water-based lubricating jelly, a dry lubricant, a powdered lubricant, a moisture-activated lubricant, and any combination thereof. The lubricant may be disposed on the inner surface 105 and/or the outer surface 110 at the time of manufacturing and packing. In other instances, the lubricant may be applied to the inner surface 105 and/or the outer surface 110 by a physician or technician prior to use so long as the surfaces and the lubricant remain sterile.

In some instances, the inner bore 115 or inner surface 105 of shielding member 150 may include a lubricating coating or a friction-reducing coating that serves a similar function as the lubricant described above. In some cases, the outer surface 110 of the shielding member 150 may include a lubricating coating or a friction-reducing coating that also serves the same or similar function as the lubricant described above.

Figure 2:
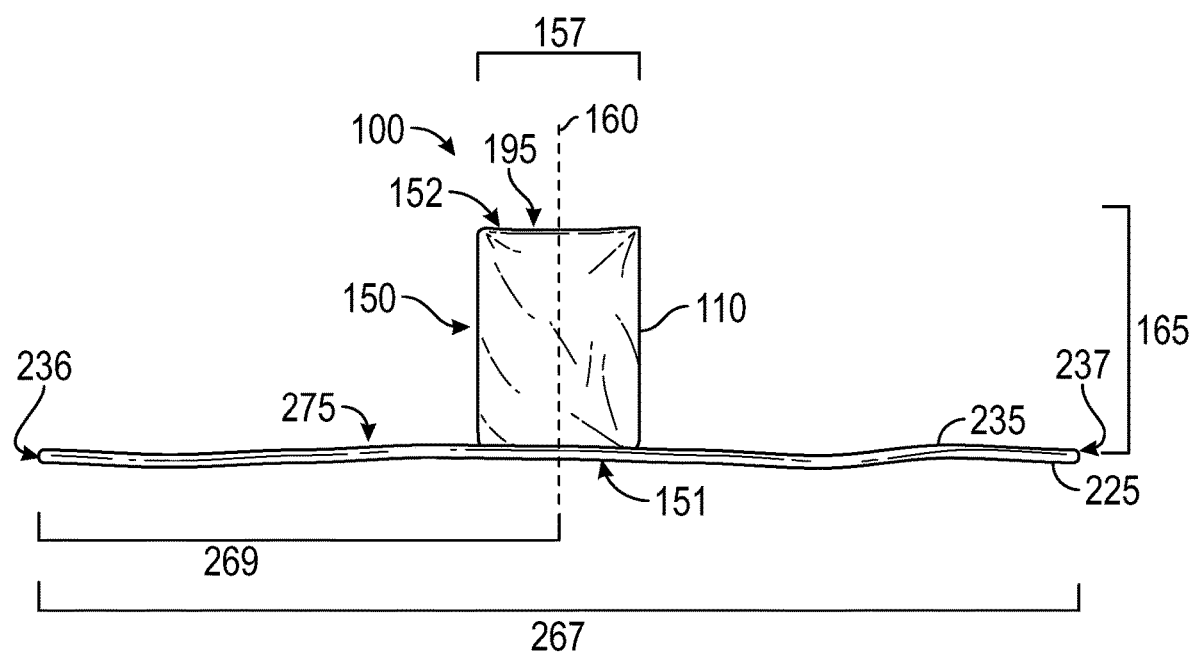
FIG. 2 is a planar view of an implant delivery device with biofilm protection shield having a substantially rectangular-shaped delivery member, according to an exemplary embodiment of the present disclosure.

FIG. 2 is a planar view of the implant delivery device 100, according to an exemplary embodiment of the present disclosure. As depicted in FIG. 2, implant delivery device 100 includes delivery member 275 and shielding member 150 extending through the delivery member 275 to form aperture 220 (not shown in FIG. 2; see FIG. 4). The shielding member 150 has an inner bore 115, a proximal end 151 and a distal end 152. The delivery member 275 radially extends from at least a portion of the proximal end 151 of shielding member 150. The inner bore 115 has a longitudinal axis 160 therethrough which extends substantially perpendicular and/or orthogonally to the delivery member 275. As shown in FIG. 2, the inner bore 115 extends longitudinally a predetermined length 165 away from the lower surface 235 of the delivery member 275 and between the proximal end 151 and the distal end 152. The shielding member 150 likewise extends along the longitudinal axis 160 a predetermined length 165 away from the lower surface 235 of the delivery member 275 and substantially perpendicular and/or orthogonally to the delivery member 275.

Figure 3:
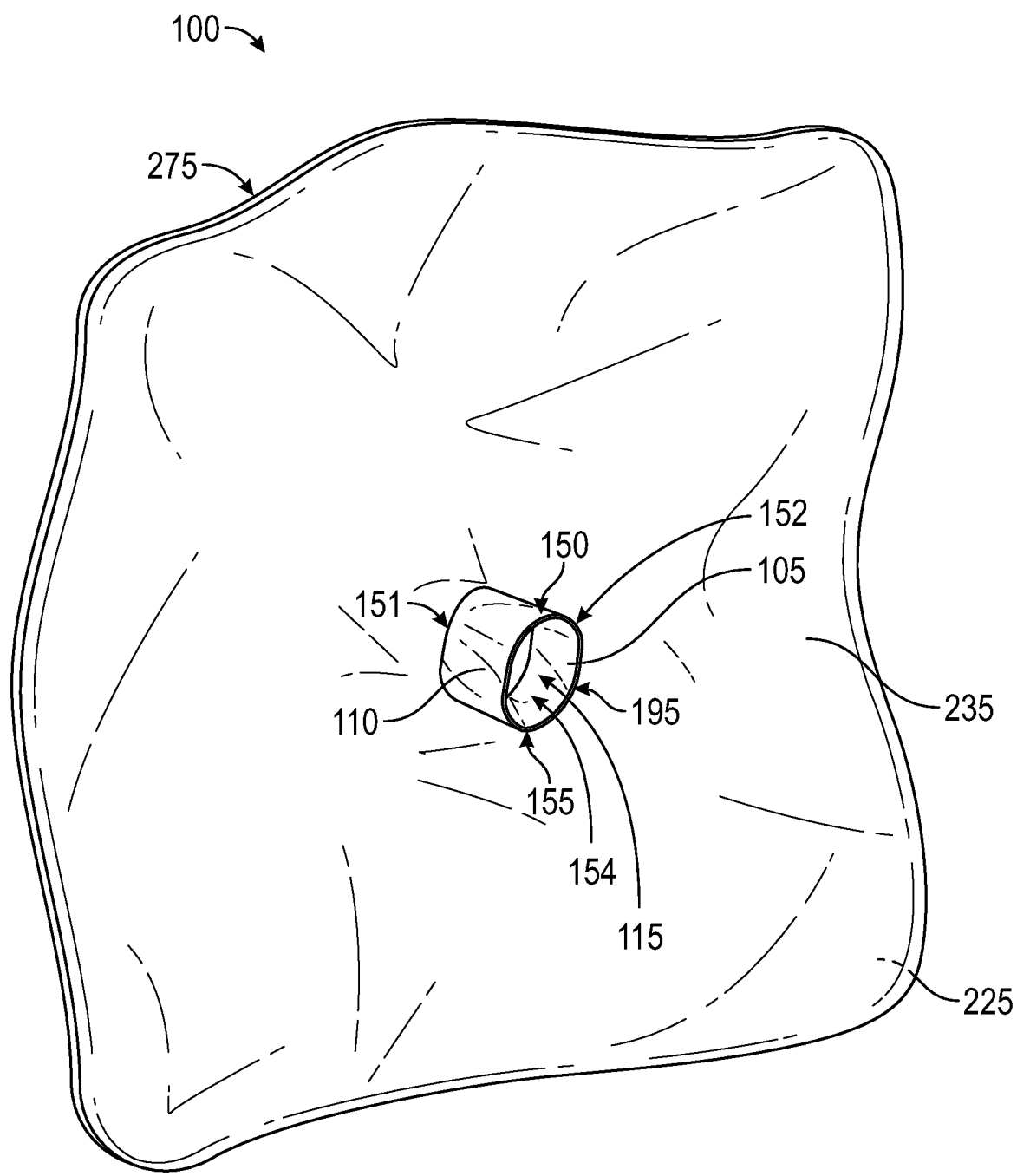
FIG. 3 is a front diagrammatic view of an implant delivery device showing the distal end of the shielding member and the lower surface of the substantially rectangular-shaped delivery member, according to an exemplary embodiment of the present disclosure.
Figure 4:
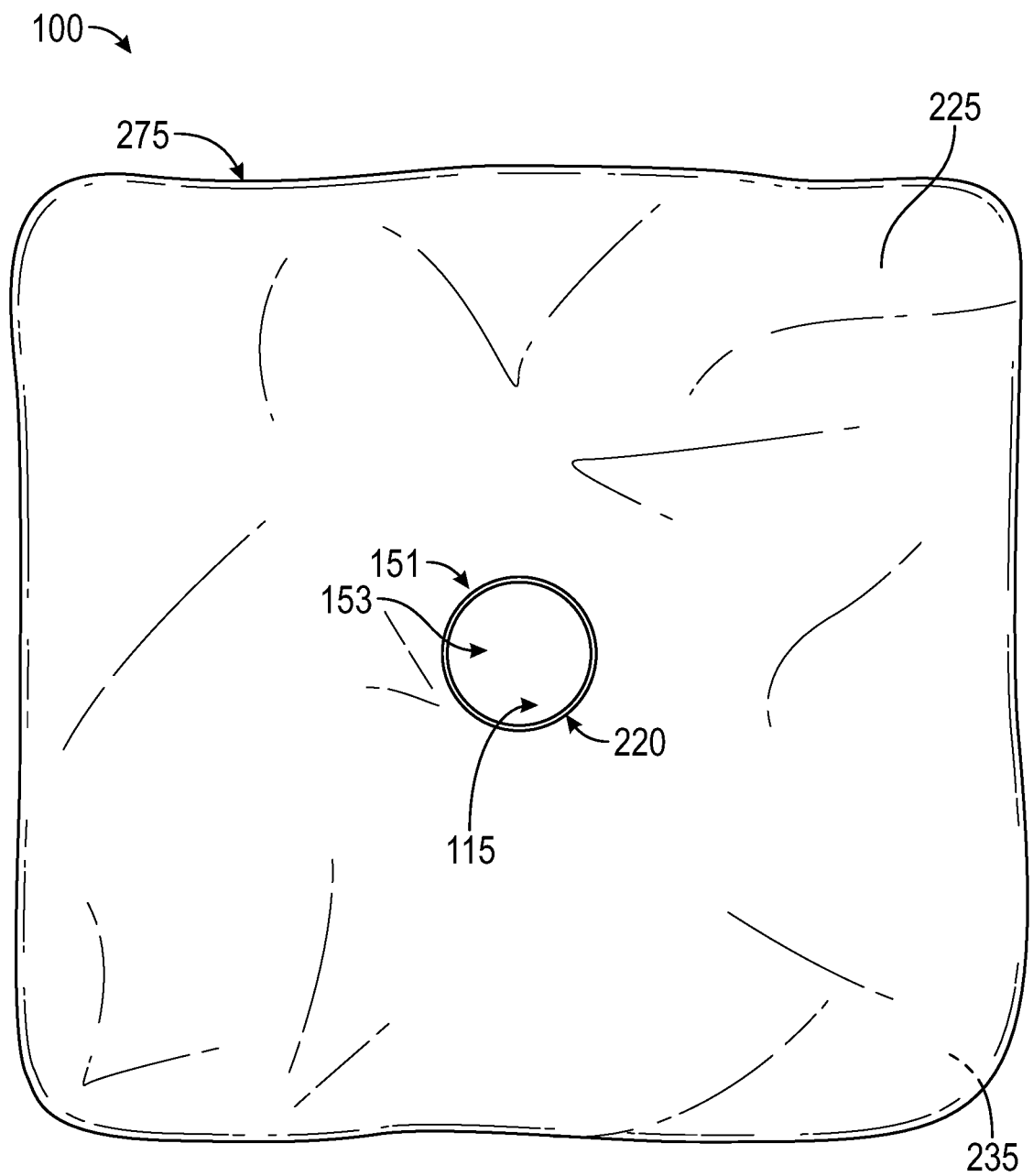
FIG. 4 is a rear planar view of the implant delivery device showing the aperture formed in the delivery member coupled with the proximal end of the shielding member and the upper surface of the substantially rectangular-shaped delivery member, according to an exemplary embodiment of the present disclosure.

FIG. 3 is a front diagrammatic view of the implant delivery device 100 showing the distal end 152 of shielding member 150 and the lower surface 235 of the delivery member 275, according to an exemplary embodiment of the present disclosure. As depicted in FIG. 3, the proximal end 151 of shielding member 150 is coupled with delivery member 275 of the implant delivery device 100. The distal end 152 of the shielding member 150 comprises aperture 155 through which an implant may exit after transiting through at least a portion of the dissection tunnel during delivery to the implant pocket. FIG. 4 is a rear diagrammatic view of the biofilm protection implant shield apparatus 100 showing delivery member 275 having an aperture 220 formed therein and extending through the upper surface 225 and the lower surface 235 of the delivery member 275.

The delivery member 275 can have any shape, configuration, diameter, or thickness so long as the delivery member 275 is operable to wrap around the implant to form a conforming cavity around the implant that conforms to the shape of the implant and so long as the delivery member 275 is operable to cause the translation of the implant from the conforming cavity through aperture 220 and the inner bore 115 of the shielding member 150 upon the application of mechanical force to the lower surface 235 of the delivery member 275. For example, in at least some instances, the delivery member 275 may be substantially rectangular as shown in FIGS. 1-8, or the delivery member 275 may be, for example, substantially circular as shown in FIGS. 9-13.

As depicted in FIG. 2, the delivery member 275 may have a diameter 267. As used herein, the diameter 267 of the delivery member 275 is defined as the minimum distance between two opposite outer edges of the delivery member 275 when the delivery member 275 is fully extended away from the shielding member 150 (e.g., the same position or configuration as when the delivery member is lying flat and extended on a flat surface). For example, as shown in FIG. 2, the diameter 267 of delivery member 275 is the distance between first outer edge 236 and an opposite second outer edge 237. The delivery member 275 may have any diameter 267 sufficient to be operable to wrap around the implant to form a conforming cavity around the implant that conforms to the shape of the implant. The delivery member 275 may also have any diameter 267 sufficient to be operable to cause the translation of the implant from the conforming cavity through aperture 220 and the inner bore 115 of the shielding member 150 upon the application of mechanical force to the lower surface 235 of the delivery member 275.

In at least some instances, the delivery member 275 may have a diameter 267 that is at least 3 times greater than the cross-sectional width 157 of the inner bore 115 of the shielding member 150 and/or the aperture 220 and/or the outer bore 195 of the shielding member 150. In other instances, the delivery member 275 may have a diameter 267 that is at least 4 times greater than the cross-sectional width 157 of the inner bore 115 of the shielding member 150 and/or the aperture 220 and/or the outer bore 195 of the shielding member 150. In still other cases, the delivery member 275 may have a diameter 267 that is at least 5 times greater than the cross-sectional width 157 of the inner bore 115 of the shielding member 150 and/or the aperture 220 and/or the outer bore 195 of the shielding member 150. In other instances, the delivery member 275 may have a diameter 267 that is at least 6 times greater than the cross-sectional width 157 of the inner bore 115 of the shielding member 150 and/or the aperture 220 and/or the outer bore 195 of the shielding member 150. In other cases, the delivery member 275 may have a diameter 267 that is at least 7 times greater than the cross-sectional width 157 of the inner bore 115 of the shielding member 150 and/or the aperture 220 and/or the outer bore 195 of the shielding member 150. In still other cases, the delivery member 275 may have a diameter 267 that is at least 8 times greater than the cross-sectional width 157 of the inner bore 115 of the shielding member 150 and/or the aperture 220 and/or the outer bore 195 of the shielding member 150. In still even other instances, the delivery member 275 may have a diameter 267 that is at least 10 times greater than the cross-sectional width 157 of the inner bore 115 of the shielding member 150 and/or the aperture 220 and/or the outer bore 195 of the shielding member 150.

In at least some instances, the delivery member 275 may have a diameter 267 that is more than 3 times greater than the cross-sectional width 157 of the inner bore 115 of the shielding member 150 and/or the aperture 220 and/or the outer bore 195 of the shielding member 150. In other instances, the delivery member 275 may have a diameter 267 that is more than 4 times greater than the cross-sectional width 157 of the inner bore 115 of the shielding member 150 and/or the aperture 220 and/or the outer bore 195 of the shielding member 150. In still other cases, the delivery member 275 may have a diameter 267 that is more than 5 times greater than the cross-sectional width 157 of the inner bore 115 of the shielding member 150 and/or the aperture 220 and/or the outer bore 195 of the shielding member 150. In other instances, the delivery member 275 may have a diameter 267 that is more than 6 times greater than the cross-sectional width 157 of the inner bore 115 of the shielding member 150 and/or the aperture 220 and/or the outer bore 195 of the shielding member 150. In other cases, the delivery member 275 may have a diameter 267 that is more than 7 times greater than the cross-sectional width 157 of the inner bore 115 of the shielding member 150 and/or the aperture 220 and/or the outer bore 195 of the shielding member 150. In still other cases, the delivery member 275 may have a diameter 267 that is more than 8 times greater than the cross-sectional width 157 of the inner bore 115 of the shielding member 150 and/or the aperture 220 and/or the outer bore 195 of the shielding member 150. In still even other instances, the delivery member 275 may have a diameter 267 that is more than 10 times greater than the cross-sectional width 157 of the inner bore 115 of the shielding member 150 and/or the aperture 220 and/or the outer bore 195 of the shielding member 150.

In at least some aspects, the delivery member 275 may have a diameter 267 that is from about 5 times to about 8 times greater than the cross-sectional width 157 of the inner bore 115 of the shielding member 150 and/or the aperture 220 and/or the outer bore 195 of the shielding member 150. In other aspects, the delivery member 275 may have a diameter 267 that is from about 6 times to about 8 times greater than the cross-sectional width 157 of the inner bore 115 of the shielding member 150 and/or the aperture 220 and/or the outer bore 195 of the shielding member 150. In still other aspects, the delivery member 275 may have a diameter 267 that is from about 4 times to about 8 times greater than the cross-sectional width 157 of the inner bore 115 of the shielding member 150 and/or the aperture 220 and/or the outer bore 195 of the shielding member 150. In yet further aspects, the delivery member 275 may have a diameter 267 that is from about 5 times to about 10 times greater than the cross-sectional width 157 of the inner bore 115 of the shielding member 150 and/or the aperture 220 and/or the outer bore 195 of the shielding member 150.

In at least some aspects, the cross-sectional width of the inner bore may be from about 3.5 cm to about 8 cm. In other aspects, the cross-sectional width of the inner bore is from about 2 cm to about 10 cm. In some instances, the diameter of the delivery member 275 is from about 17.5 cm to about 40 cm, or from about 10 cm to about 50 cm, or from about 21 cm to about 48 cm, or from about 12 cm to about 60 cm, or from about 24.5 cm to about 56 cm, or from about 14 cm to about 70 cm, or from about 28 cm to about 64 cm, or from about 16 cm to about 80 cm, or from about 35 cm to about 80 cm, or from about 20 cm to about 100 cm.

The delivery member 275 may also have a radial length 269, as shown in FIG. 2. As used herein, the radial length 269 of delivery member 275 is defined as the distance between an outer edge (e.g., outer edges 236, 237) of the delivery member 275, when the delivery member 275 is fully extended away from the shielding member 150 (e.g., the same position or configuration as when the base is lying flat on a flat surface and extending away from the shielding member 150), and the outer surface 110 of the proximal end 151 of the shielding member 150 where it is coupled to the delivery member 275. Accordingly, the radial length 269 of the delivery member is the length that the delivery member 275 extends away from the shielding member 150. The delivery member 275 may have any radial length sufficient to be operable to wrap around the implant to form a conforming cavity around the implant that conforms to the shape of the implant. The delivery member 275 may also have any radial length 269 sufficient to be operable to cause the translation of the implant from the conforming cavity through aperture 220 and the inner bore 115 of the shielding member 150 upon the application of mechanical force to the lower surface 235 of the delivery member 275.

Delivery member 275 may have sufficient thickness to provide structural support or rigidity to be operable to propel the implant from the conforming cavity through aperture 220 formed in the delivery member 275 and into the inner bore 115 of the shielding member 150 upon the application of mechanical force to the lower surface 235 of the delivery member 275. In some instances, the delivery member 275 may have a thickness (e.g., the distance or thickness between the lower surface 235 and the upper surface 225 of delivery member 275) that is substantially the same as the thickness of the shielding member 150. In other instances, the delivery member 275 may have a thickness that is substantially thicker than the thickness of the shielding member 150. In other instances, the delivery member 275 may have a thickness that is substantially thinner than the thickness of the shielding member 150. In such instances, the shielding member 150 may be thicker than the thickness of the delivery member 275 so that the shielding member 150 has sufficient rigidity or structural integrity to facilitate insertion into the dissection tunnel while resisting the forces created by insertion of the implant into the inner bore 115 such that the shielding member 150 is operable to shield the implant from the dissection tunnel during transit of the implant along the inner bore to the implant pocket.

Figure 5:
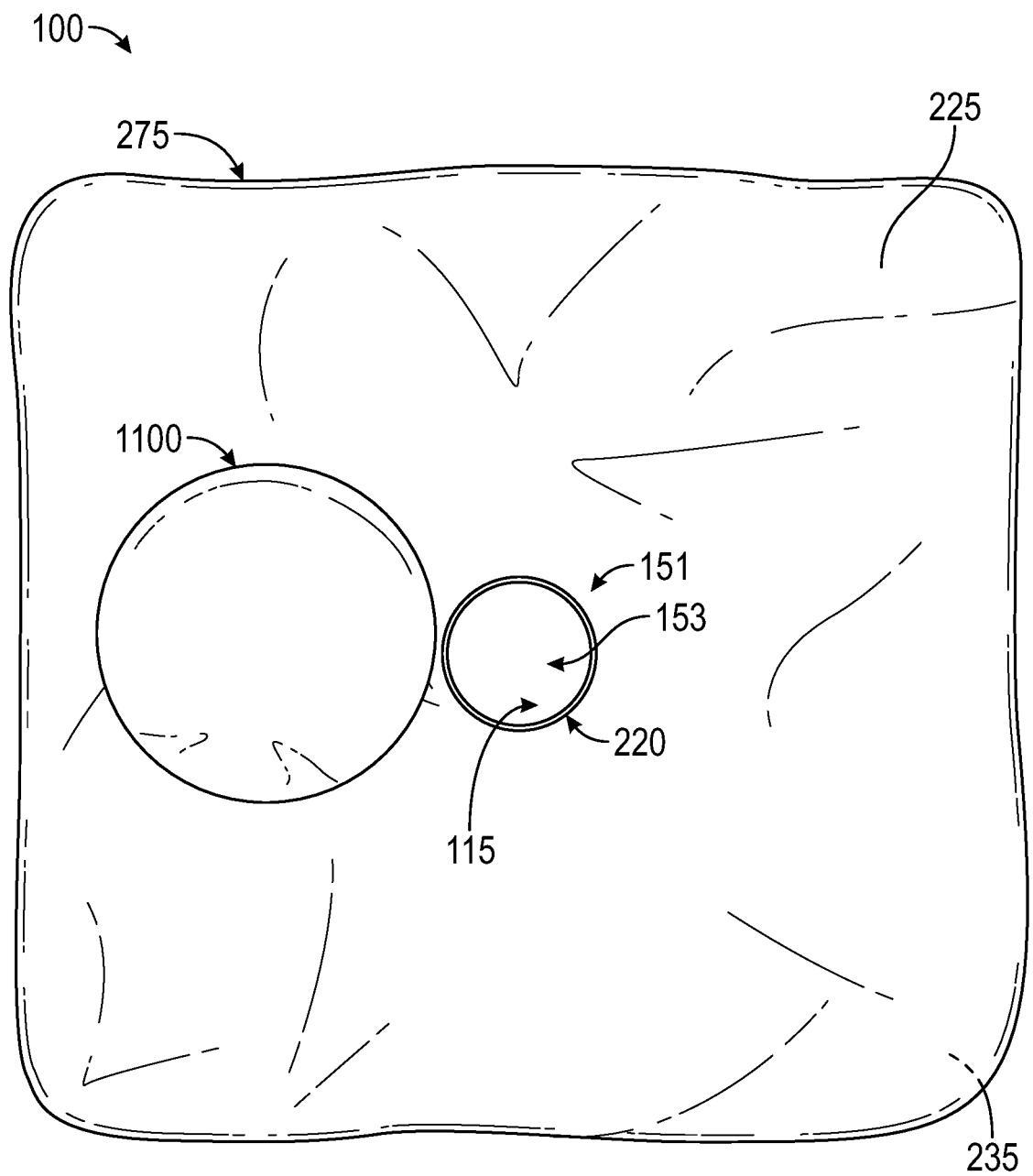
FIG. 5 is a rear planar view of the implant delivery device with an implant placed on the upper surface of the rectangular delivery member, according to an exemplary embodiment of the present disclosure.

FIG. 5 is a rear planar view of the implant delivery device 100 with an implant 1100 placed on the upper surface 225 of the delivery member 275. As shown in FIG. 5, delivery member 275 has a substantially rectangular shape. However, delivery member 275 may have any size and shape so long as it is operable to wrap around the implant 1100 to form a conforming cavity around the implant 1100 that conforms to the shape of the implant 1100 and so long as the delivery member 275 is operable to cause the translation of the implant 1100 from the conforming cavity through aperture 220 and the inner bore 115 of the shielding member 150 upon the application of mechanical force to the lower surface 235 of the delivery member 275. As depicted in FIG. 5, implant 1100 is placed on the upper surface 225 of delivery member 275 so that it may be wrapped by the delivery member 275. Implant 1100 may be placed on the upper surface 225 of delivery member 275 by any sterile means. In at least some instances, the implant 1100 may be placed on the upper surface 225 of the delivery member straight from the implant packaging that the implant 1100 is provided in so that implant delivery device 100 provides no touch insertion and protected delivery to the implant pocket of the subject while the shielding member 150 shields the implant 1100 from the endogenous flora of the dissection tunnel.

Figure 6:
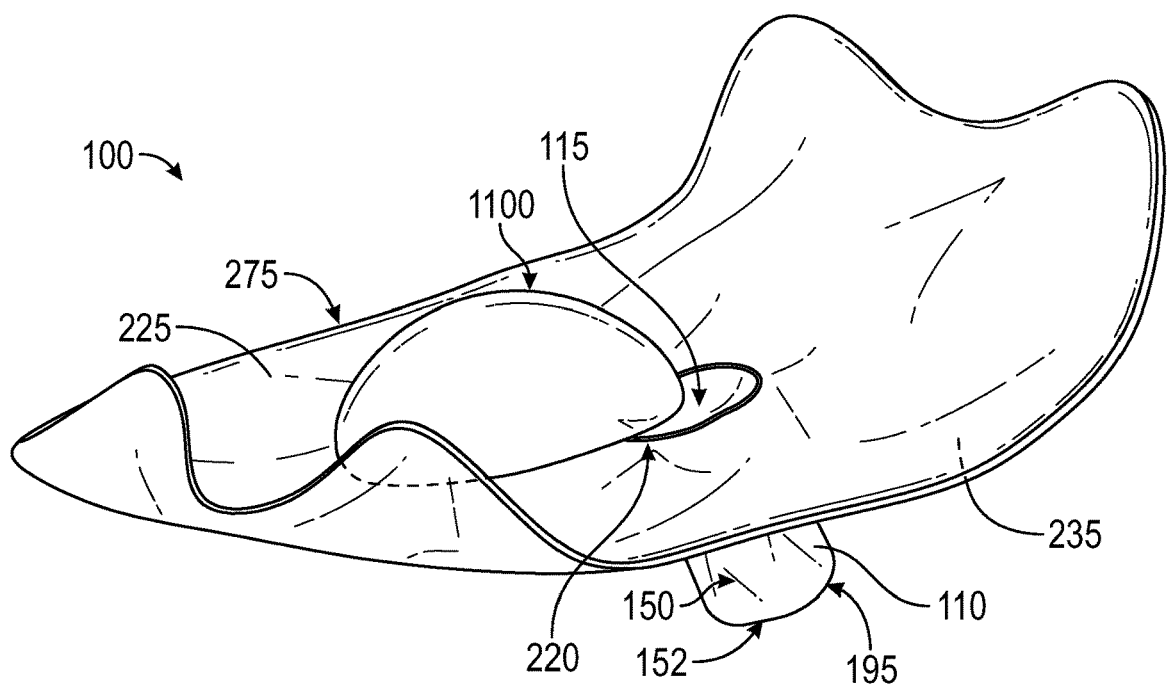
FIG. 6 is a rear diagrammatic view of the implant delivery device depicting the substantially rectangular delivery member starting to wrap around the implant to form a conforming cavity with the implant disposed therein, according to an exemplary embodiment of the present disclosure.
Figure 7:
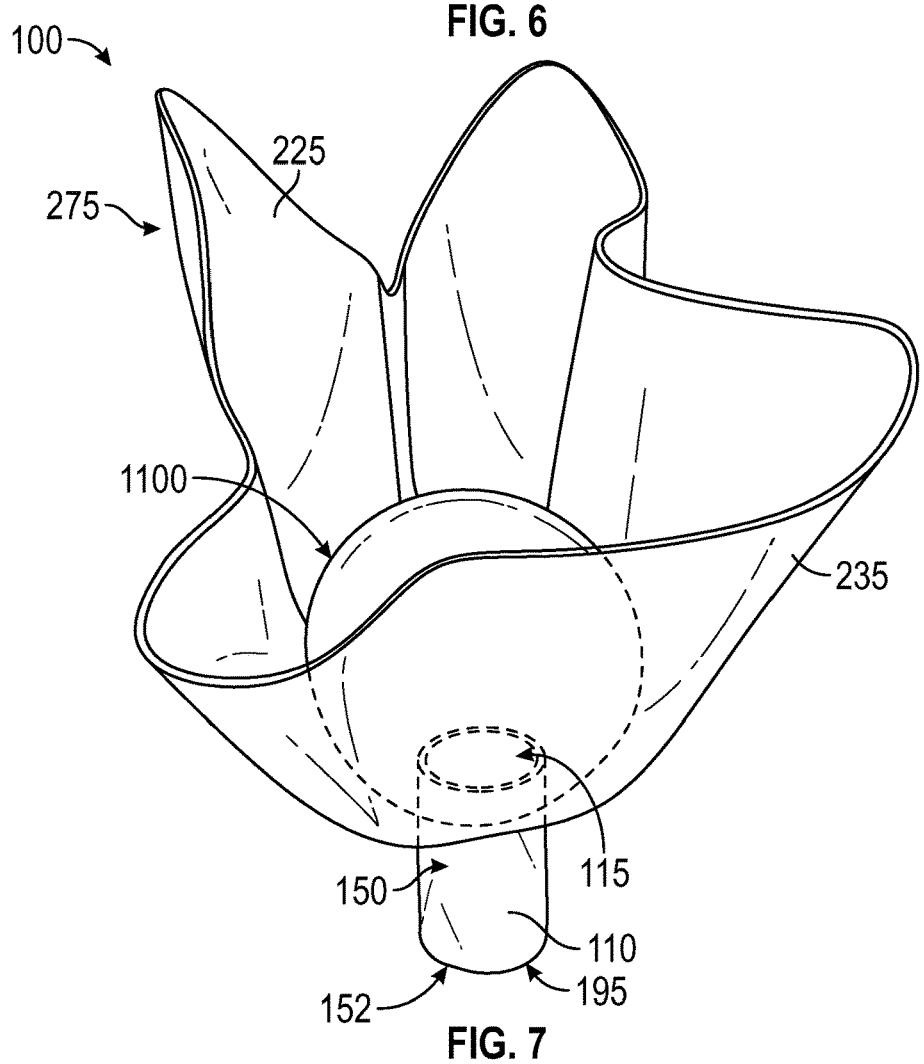
FIG. 7 is a rear diagrammatic view of the implant delivery device having a substantially rectangular delivery member illustrating the wrapping of the delivery member around the implant to form a conforming cavity that conforms to the shape of the implant with the implant disposed therein, according to an exemplary embodiment of the present disclosure.
Figure 8:
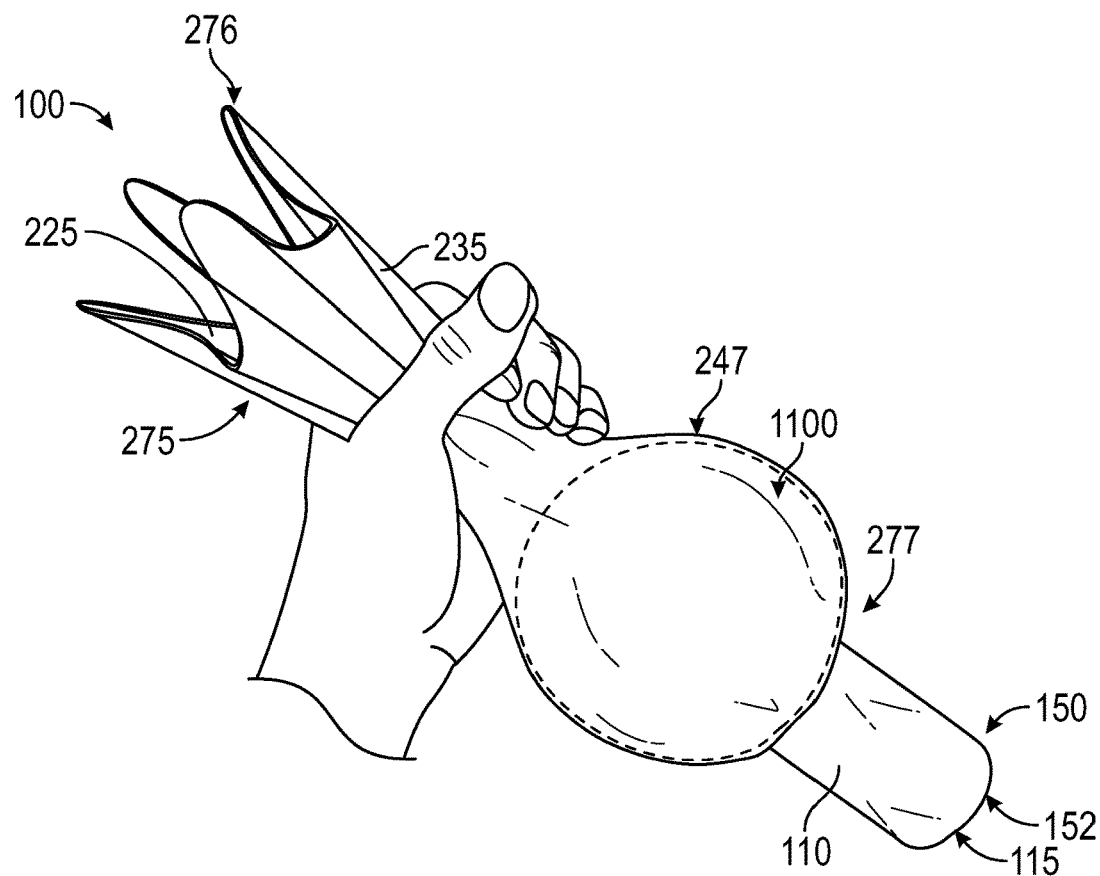
FIG. 8 is a rear diagrammatic view of the implant delivery device having an implant disposed in a conforming cavity formed by the delivery member by wrapping the implant in the substantially rectangular delivery member, according to an exemplary embodiment of the present disclosure.

FIG. 6 is a rear diagrammatic view of the implant delivery device 100. As shown in FIG. 6, the substantially rectangular delivery member 275 is beginning to wrap around the implant 1100 to form a conforming cavity around the implant 1100. FIG. 7 shows the further wrapping of the delivery member 275 around the implant 1100 to begin to create a conforming cavity that conforms to the shape and size of the implant with the implant disposed therein. As shown in FIG. 8, the further wrapping of implant 1100 in the delivery member 275 forms a conforming cavity 247 around implant 1100 such that the implant 1100 is in contact with the upper surface 225 of the delivery member 275 and the flexible delivery member 275 has tightly conformed to the shape of the implant 1100, thereby forming a conforming cavity 247 that substantially takes the shape of the implant 1100. At this point, the implant 1100 is loaded in the implant delivery device 100 and may be safely carried around and manipulated by the surgeon without risk of contamination. In particular, implant 1100 is disposed in the conforming pocket 247 toward the distal end 277 of the delivery member 275 while the hand of the user or surgeon is holding the proximal end 276 of the delivery member 275. Therefore, implant delivery device 100 provides for no touch delivery and protected insertion into the implant pocket of the patient. Once the implant 1100 is loaded in the delivery member 275, the implant 1100 does not translate from the delivery member 275 through aperture 220 and into the inner bore 115 of the shielding member 150 unless mechanical force (e.g., squeezed) is applied to the lower surface 235 of the delivery member 275.

Importantly, because the implant delivery device 100 does not include an aperture or preformed structure for receiving or loading the implant into the delivery device 100, the implant delivery device 100 has the complete flexibility to be used with any size, texture, or shape of breast implant in common use. Accordingly, the implant delivery device 100 does not need to be modified based on the shape or size of the implant as the delivery member 275 is tightly wrapped around the implant 1100, thereby precisely conforming to the size and shape as well as the individual specifications of the implant. The delivery member 275, when loaded with the implant, creates a conforming cavity 247 tightly conforming to the implant 1100 with the conforming cavity 247 being round, elliptical, teardrop shaped, or any shape corresponding to the shape of the selected implant 1100. Because the implant delivery device 100 does not include a preformed cavity, the implant delivery device 100 is equally suited for implants 1100 of any size or shape since the delivery member 275 conforms to the precise shape and specifications of the implant 1100. Further, it has been discovered that use of the presently disclosed implant delivery device 100 provides for the application of substantially equal forces to the implant 1100 surface thereby providing for safer and more efficient delivery and insertion of the implant 1100 without accidentally damaging the implant 1100.

Figure 9:
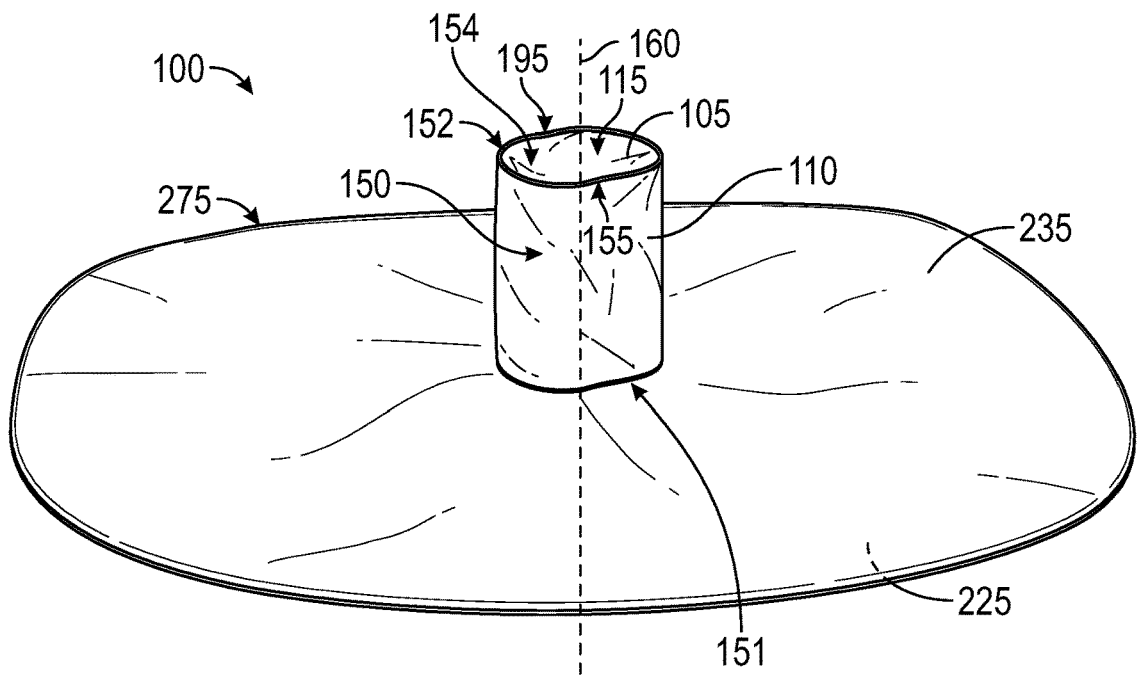
FIG. 9 is an isometric view of an implant delivery device with biofilm protection shield having a substantially ellipse-shaped delivery member and a shielding member, according to an exemplary embodiment of the present disclosure.
Figure 10:
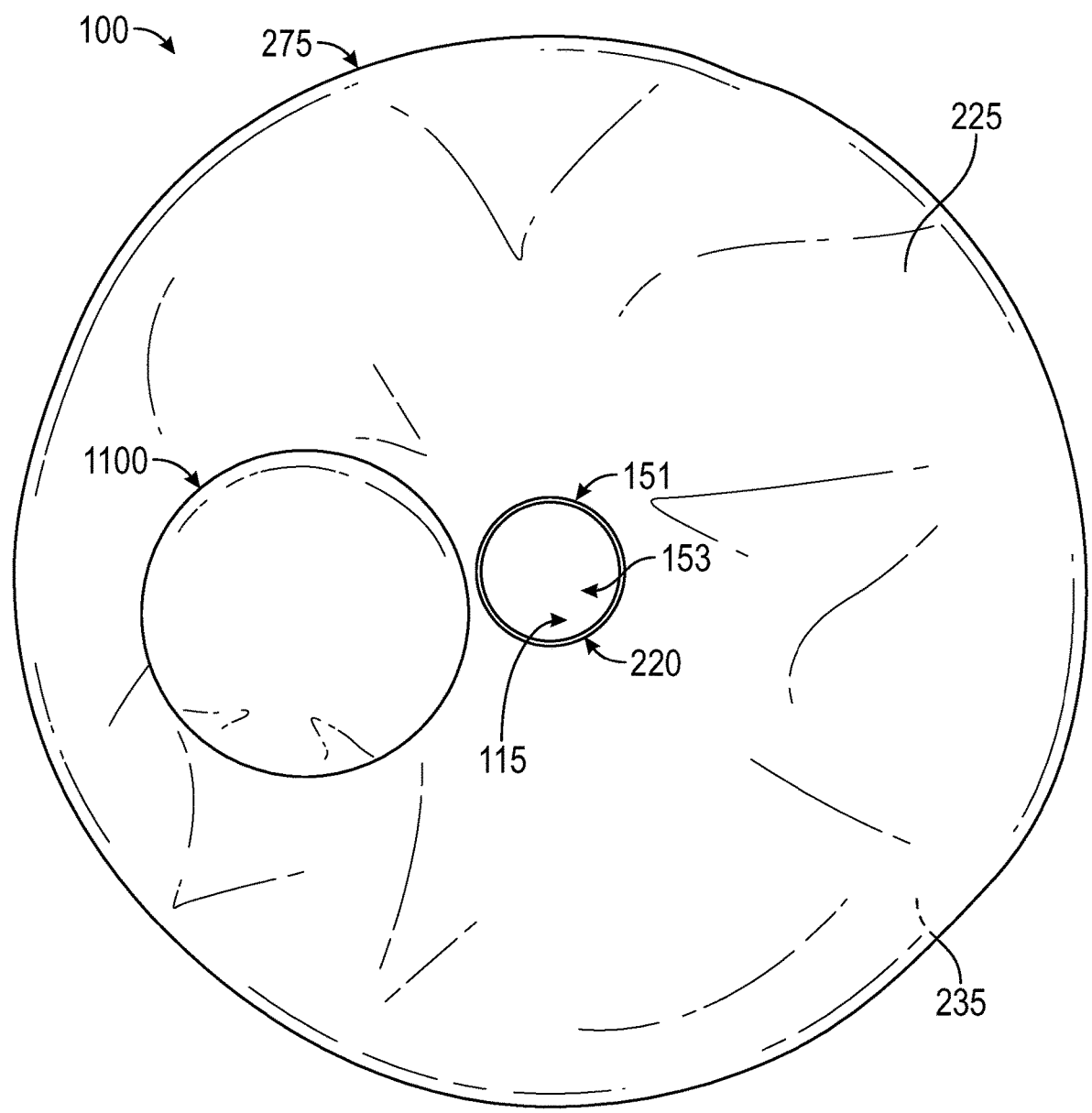
FIG. 10 is a rear planar view of the implant delivery device with an implant placed on the upper surface of the elliptical delivery member, according to an exemplary embodiment of the present disclosure.
Figure 11:
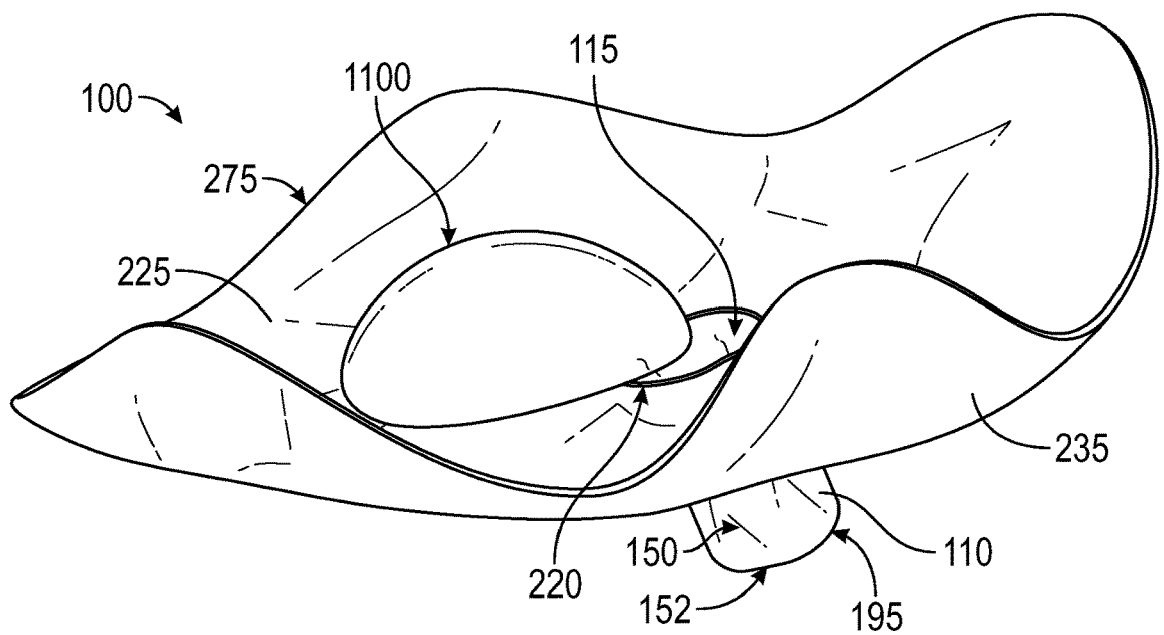
FIG. 11 is a rear diagrammatic view of the implant delivery device depicting the substantially elliptical delivery member starting to wrap around the implant to form a conforming cavity with the implant disposed therein, according to an exemplary embodiment of the present disclosure.
Figure 12:
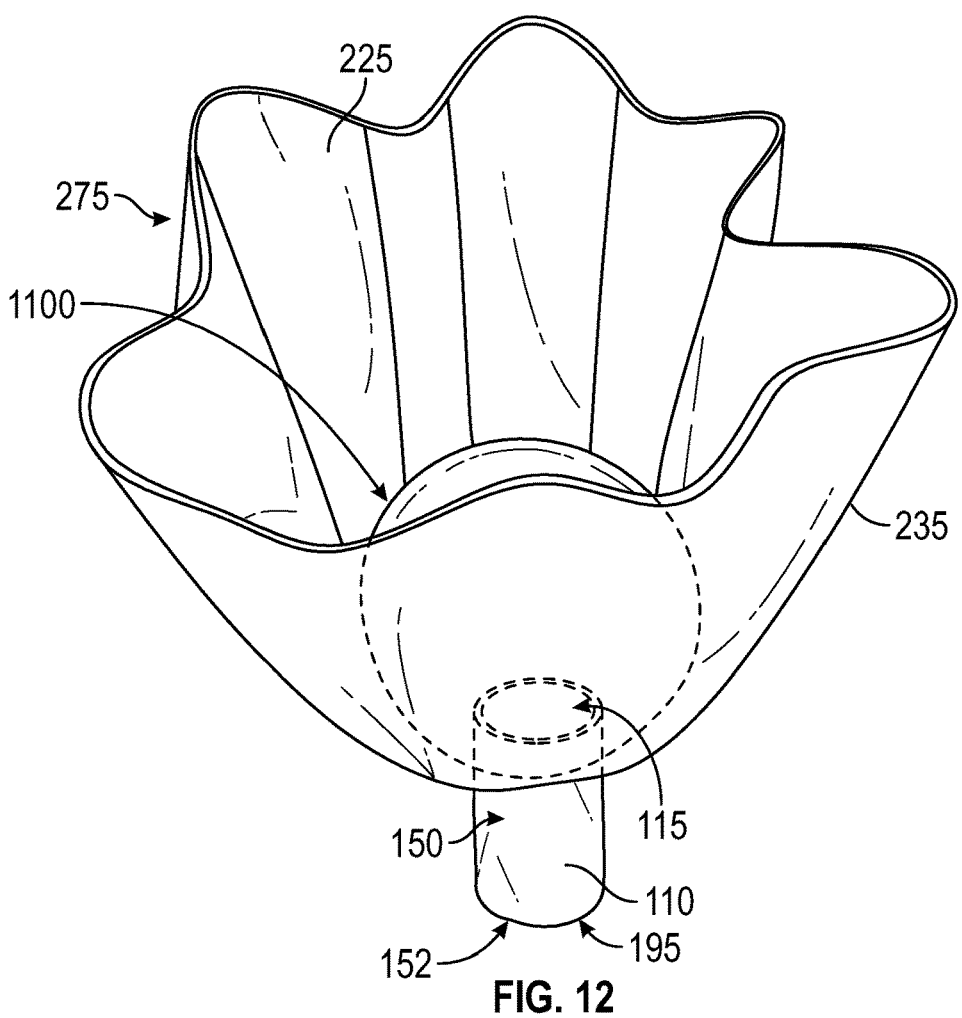
FIG. 12 is a rear diagrammatic view of the implant delivery device having a substantially elliptical delivery member illustrating the wrapping of the delivery member around the implant to form a conforming cavity that conforms to the shape of the implant with the implant disposed therein, according to an exemplary embodiment of the present disclosure.
Figure 13:
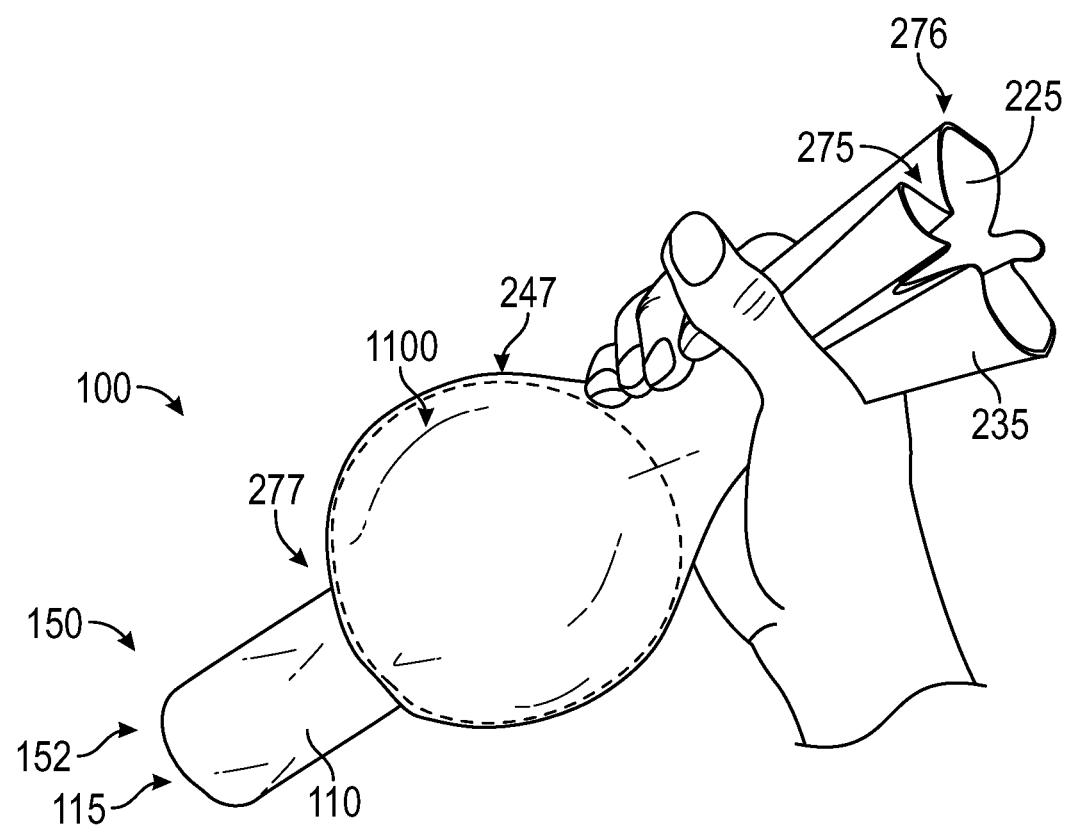
FIG. 13 is a rear diagrammatic view of the implant delivery device having an implant disposed in a conforming cavity formed by the delivery member by wrapping the implant in the substantially elliptical delivery member, according to an exemplary embodiment of the present disclosure.

As shown in FIG. 9, implant delivery device 100 may include a delivery member 275 that is substantially circular in shape. As shown in FIG. 10, the implant 1100 may be placed on the upper surface 225 of delivery member 275, similar to that described for FIG. 5. FIG. 11 depicts the substantially circular delivery member 275 beginning to wrap around the implant 1100 to form a conforming cavity around the implant 1100. FIG. 12 shows the further wrapping of the delivery member 275 around the implant 1100 to begin to form a pocket that conforms to the shape of the implant with the implant disposed therein. As shown in FIG. 13, the further wrapping of implant 1100 in the delivery member 275 forms a conforming cavity 247 around implant 1100 such that the implant 1100 is in contact with the upper surface 225 of the delivery member 275. At this point, the implant 1100 is loaded in the implant delivery device 100 and may be safely carried around and manipulated by the surgeon without risk of contamination. In particular, the implant delivery device 100 loaded with implant 1100 may be manipulated by the surgeon to the incision site for insertion of the implant 1100 and delivery of the implant 1100 to the implant pocket.

Figure 14:
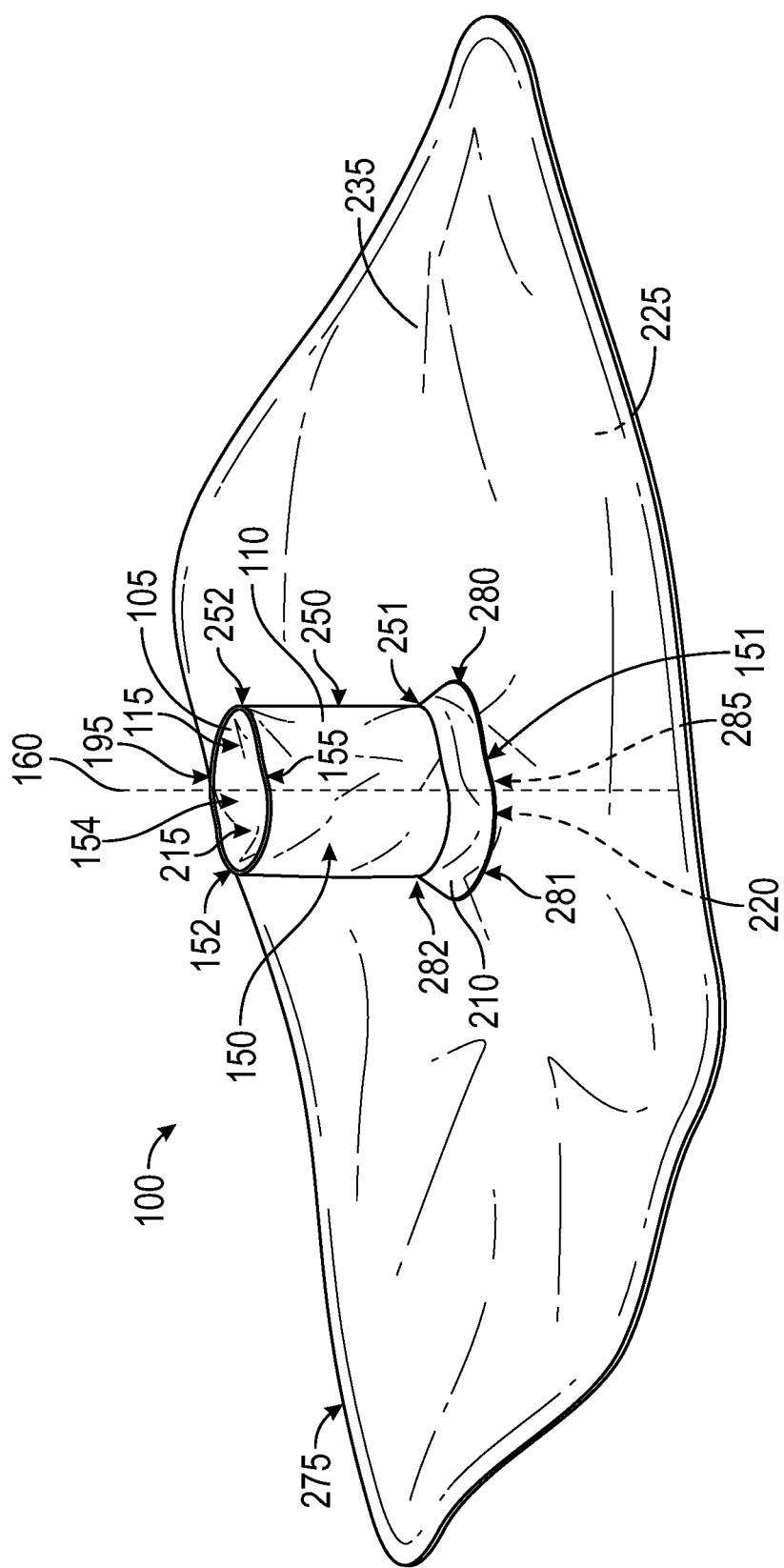
FIG. 14 is an isometric view of an implant delivery device having a delivery member and a shielding member that includes both a tubular member and a conical member, according to an exemplary embodiment of the present disclosure.
Figure 15:
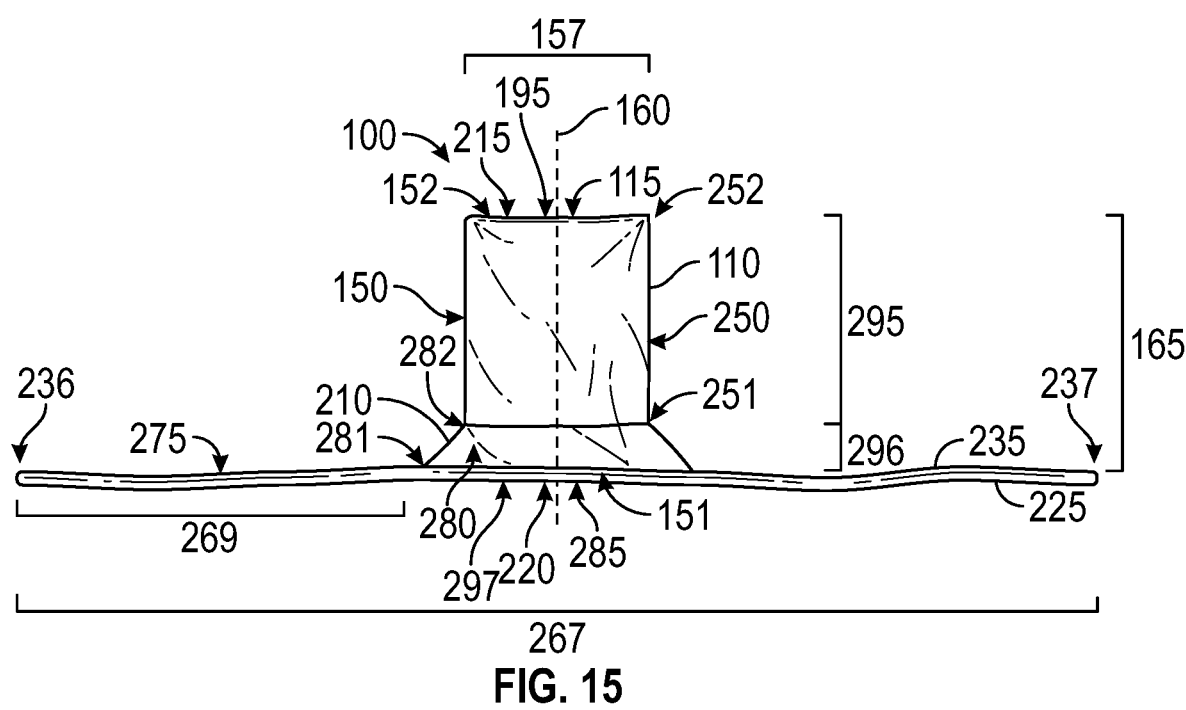
FIG. 15 is a planar view of an implant delivery device having a delivery member and a shielding member that includes both a conical member and a tubular member, according to an exemplary embodiment of the present disclosure.
Figure 16:
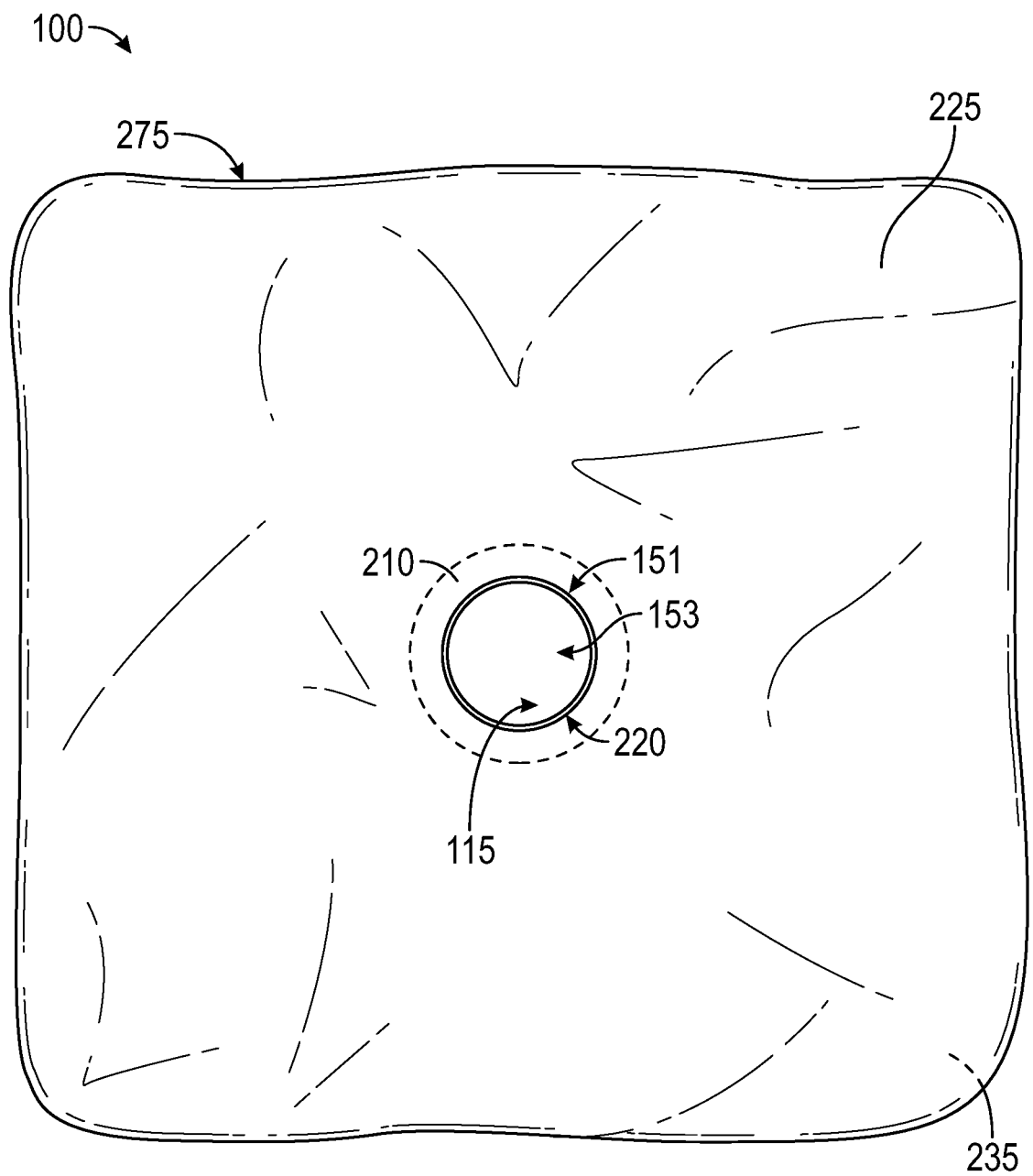
FIG. 16 is a rear planar view of the implant delivery device showing the aperture formed in the delivery member coupled with the proximal end of a shielding member that includes both a conical member and a tubular member, according to an exemplary embodiment of the present disclosure.
Figure 17:
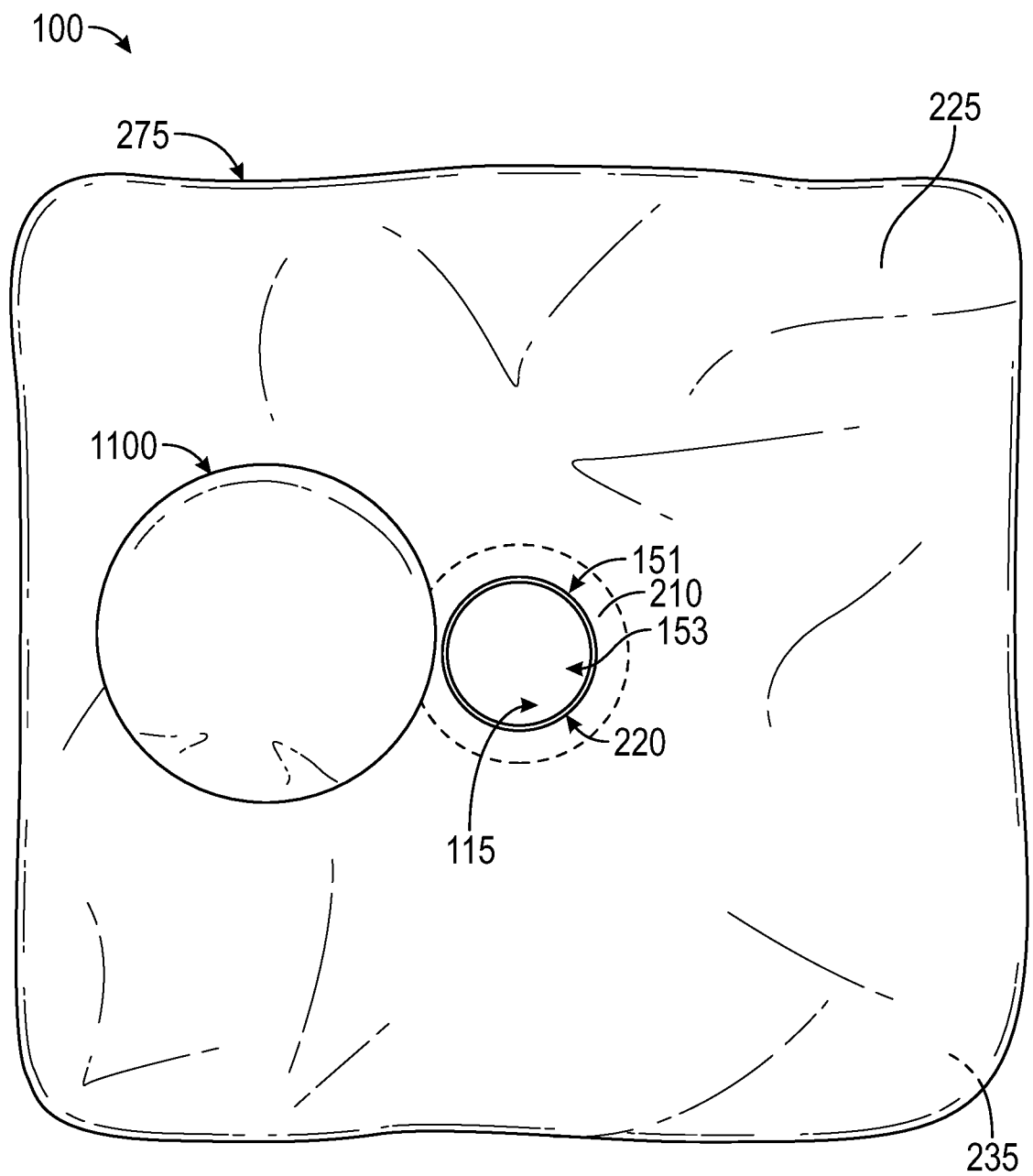
FIG. 17 is a rear planar view of the implant delivery device having a shielding member that includes both a conical member and a tubular member and with an implant placed on the upper surface of the delivery member, according to an exemplary embodiment of the present disclosure.
Figure 18:
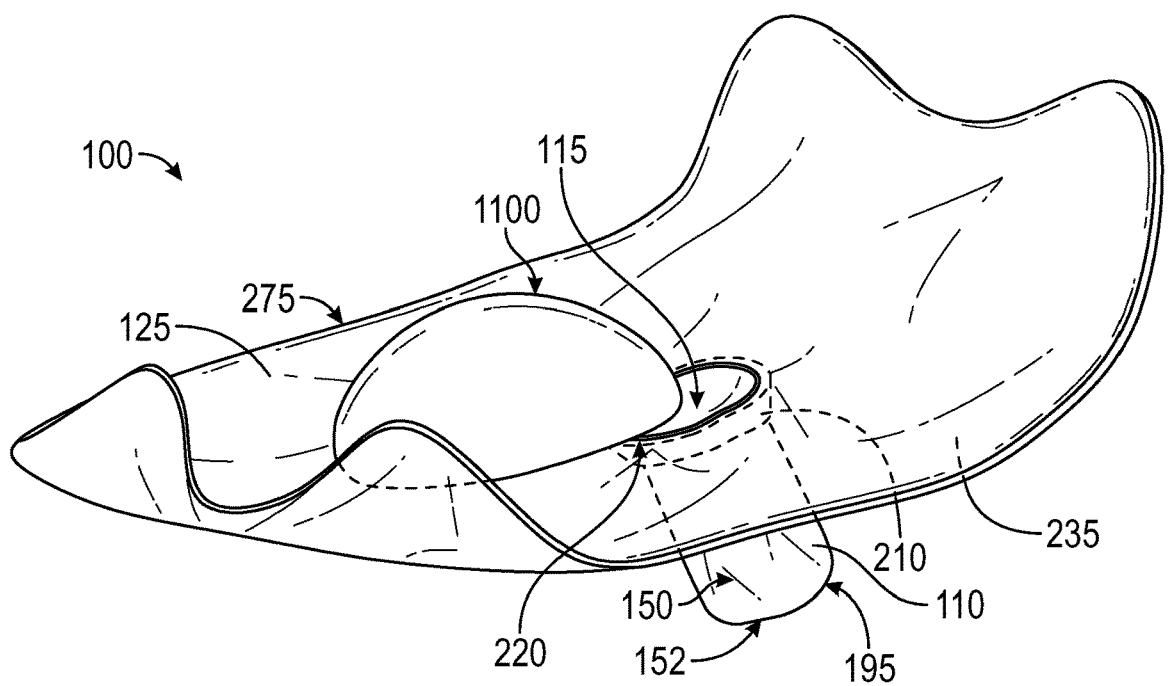
FIG. 18 is a rear diagrammatic view of the implant delivery device having a shielding member that includes both a conical member and a tubular member and depicting the delivery member starting to wrap around the implant to form a conforming cavity with the implant disposed therein, according to an exemplary embodiment of the present disclosure.
Figure 19:
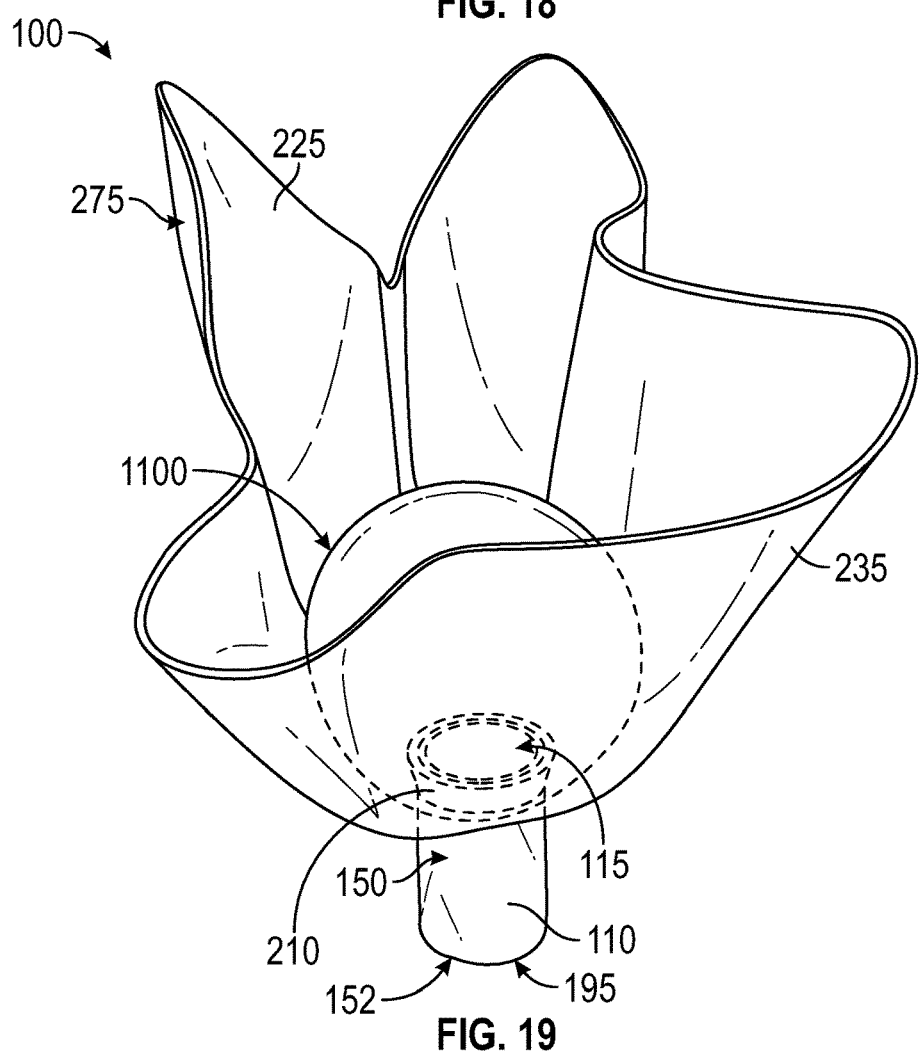
FIG. 19 is a rear diagrammatic view of the implant delivery device, having a shielding member that includes both a conical member and a tubular member, illustrating the wrapping of the delivery member around the implant to form a conforming cavity that conforms to the shape of the implant with the implant disposed therein, according to an exemplary embodiment of the present disclosure.
Figure 20:
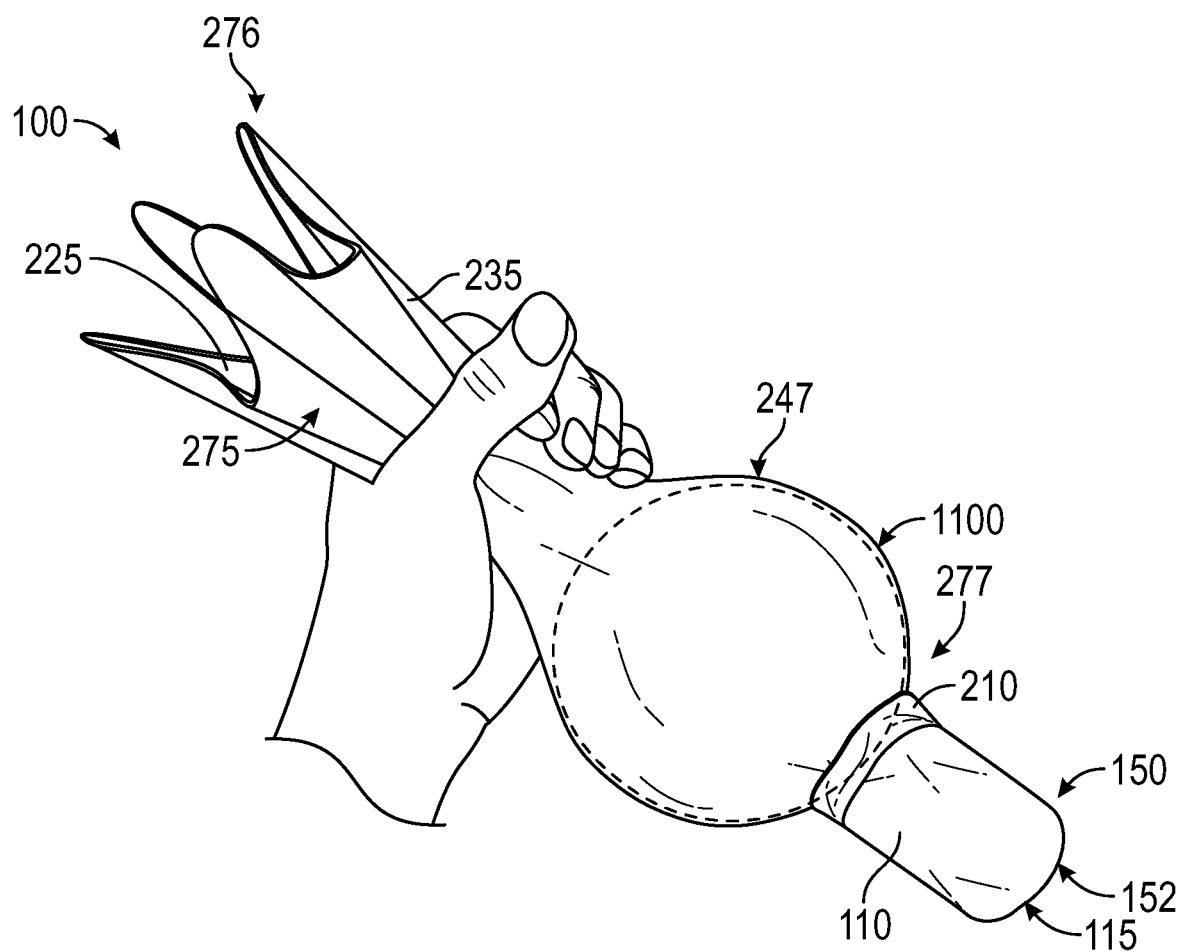
FIG. 20 is a rear diagrammatic view of the implant delivery device having a shielding member that includes both a conical member and a tubular member and having an implant disposed in a conforming cavity formed by the delivery member by wrapping the implant in the delivery member, according to an exemplary embodiment of the present disclosure.
Figure 21:
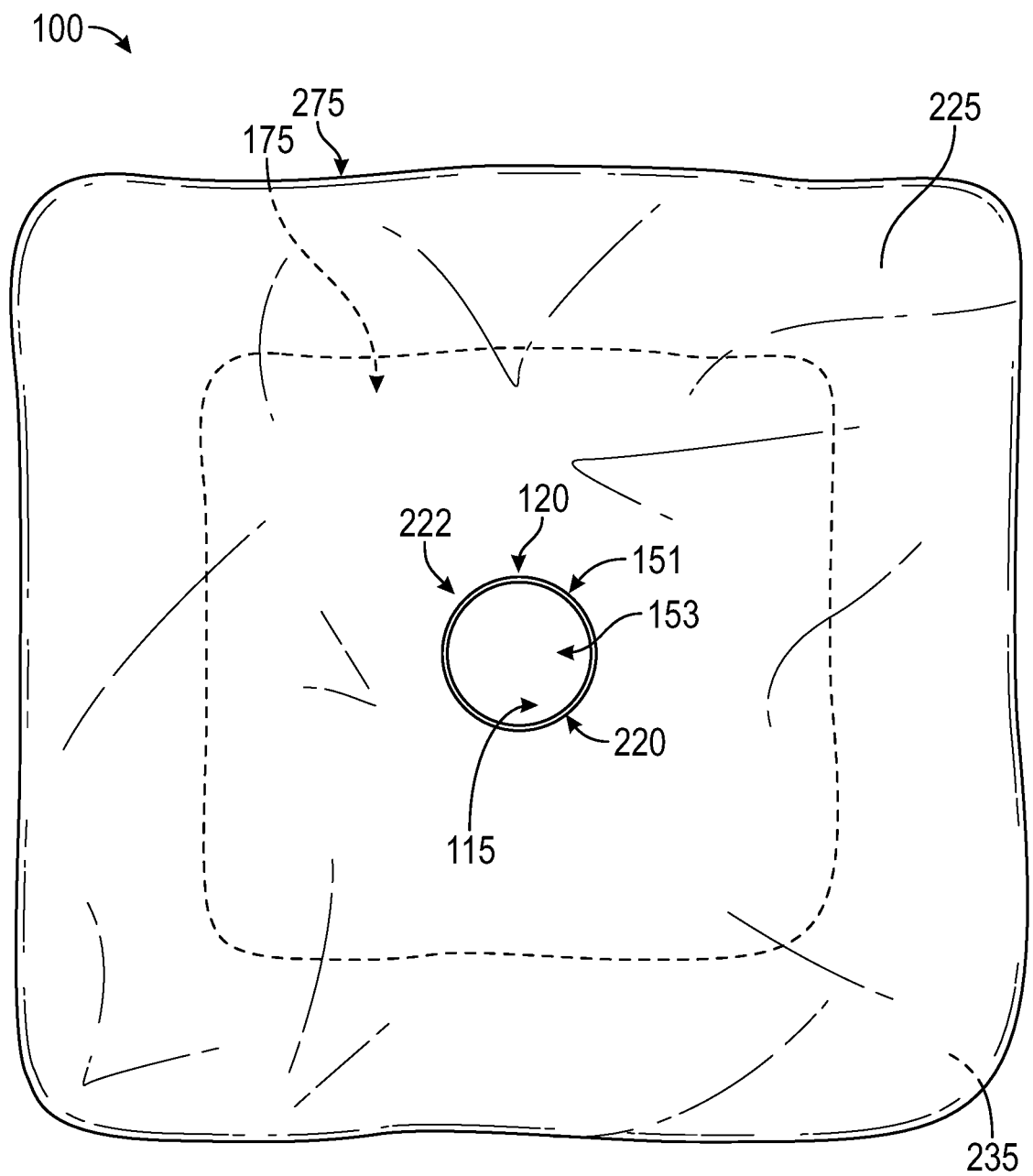
FIG. 21 is a rear planar view of an implant delivery device having a shielding member, a delivery member, and a base, and showing the aperture formed in the delivery member coupled with the proximal end of the shielding member and the base, according to an exemplary embodiment of the present disclosure.
Figure 22:
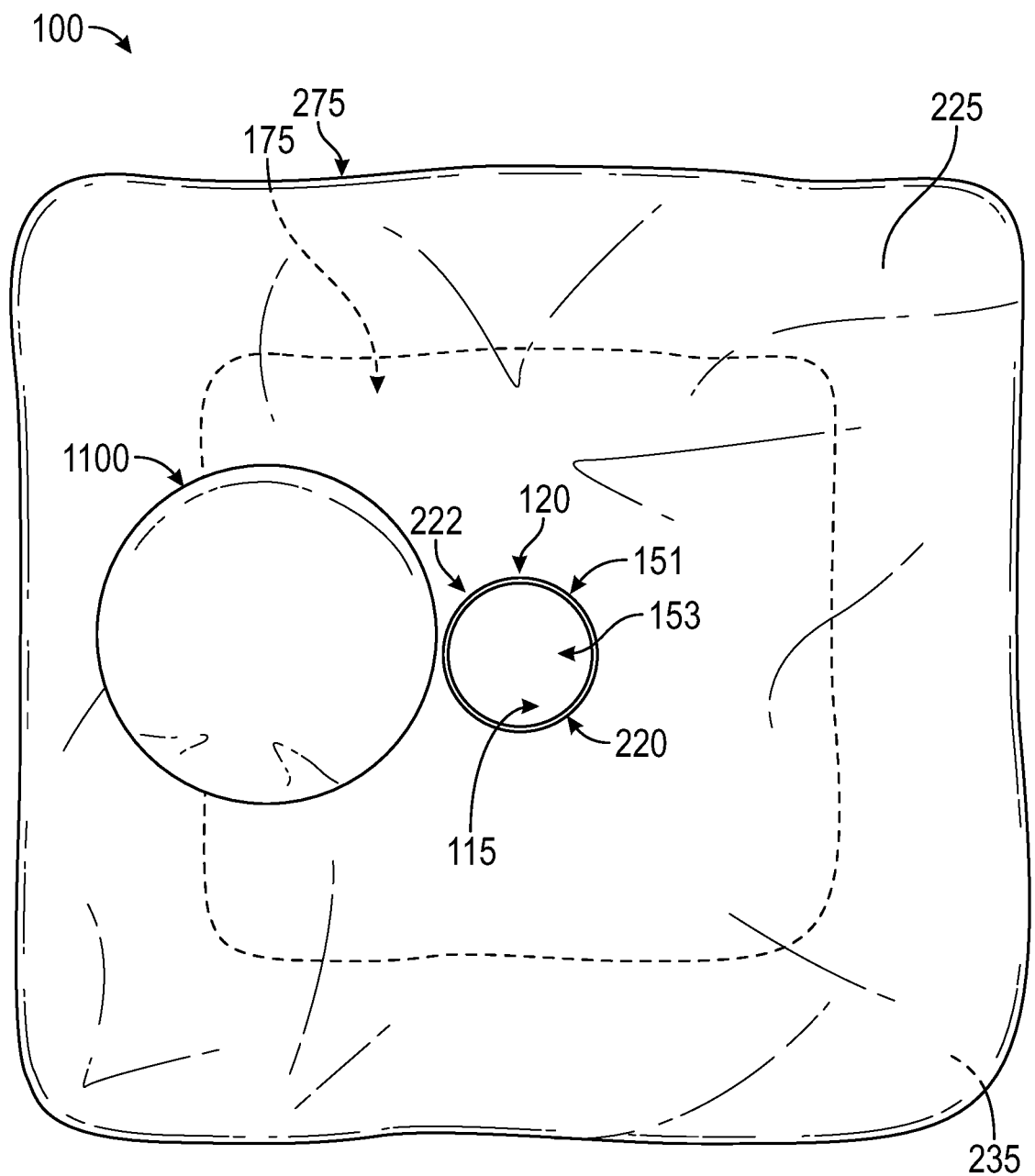
FIG. 22 is a rear planar view of the implant delivery device having a shielding member, a delivery member, and a base, with an implant placed on the upper surface of the delivery member, according to an exemplary embodiment of the present disclosure.
Figure 23:
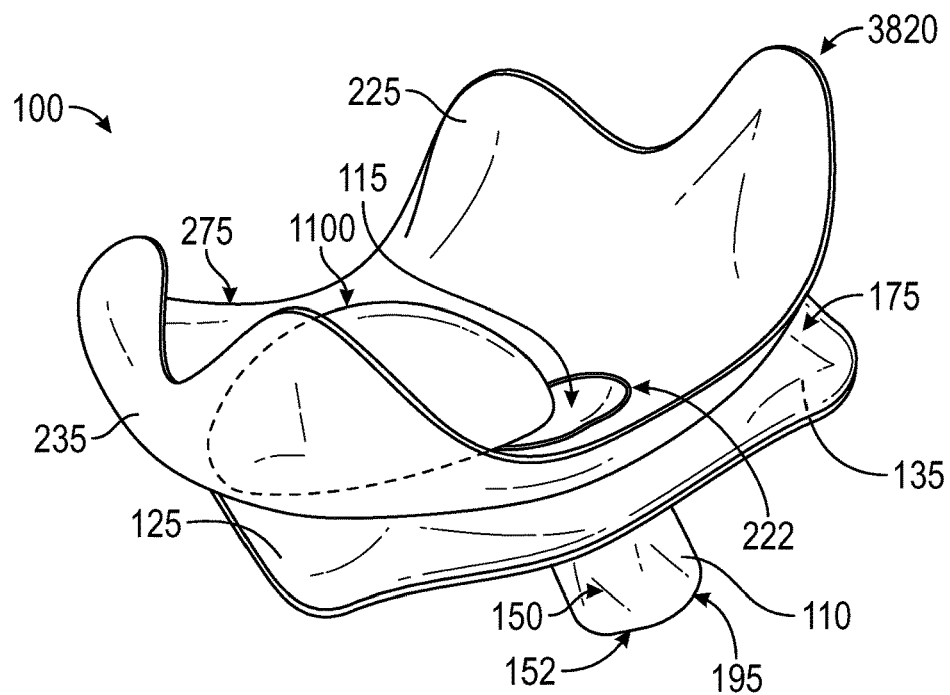
FIG. 23 is a rear diagrammatic view of the implant delivery device having a shielding member, a delivery member, and a base, depicting the delivery member starting to wrap around the implant to form a conforming cavity with the implant disposed therein, according to an exemplary embodiment of the present disclosure.
Figure 24:
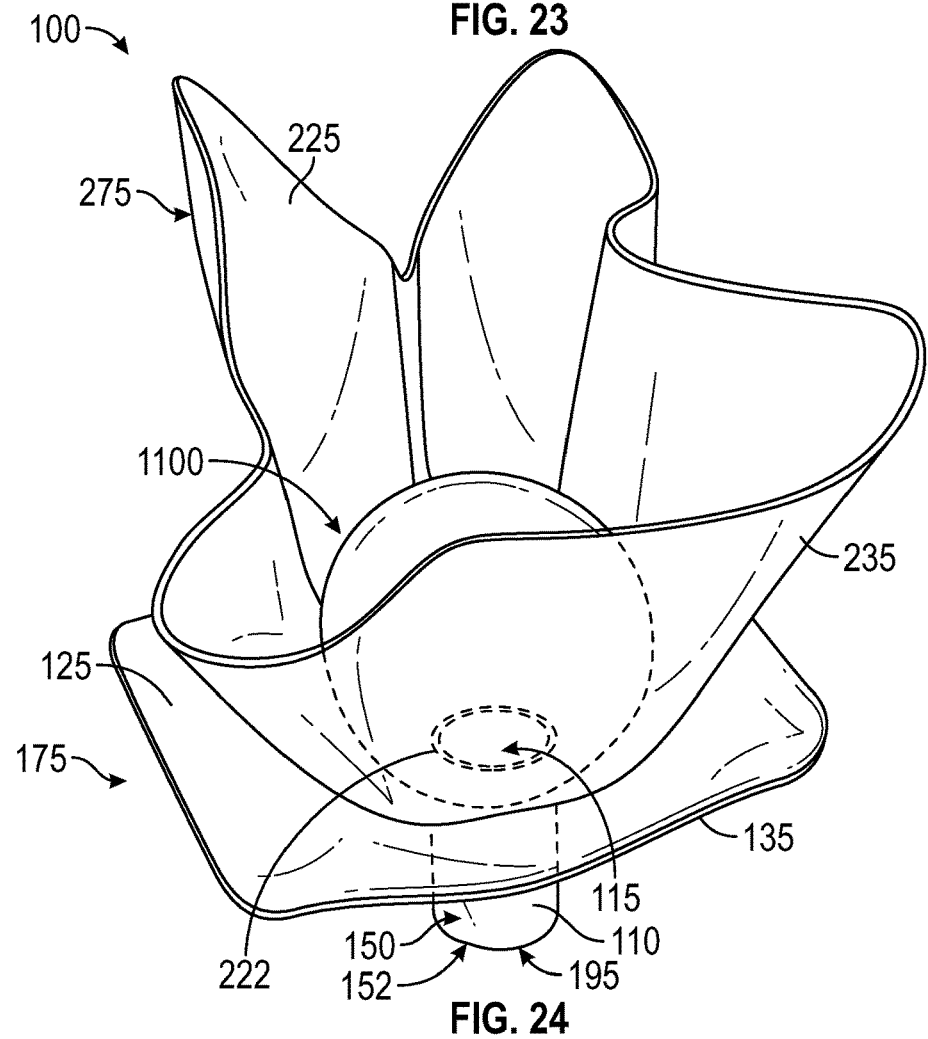
FIG. 24 is a rear diagrammatic view of the implant delivery device having a shielding member, a delivery member, and a base, illustrating the wrapping of the delivery member around the implant to form a conforming cavity that conforms to the shape of the implant with the implant disposed therein, according to an exemplary embodiment of the present disclosure.
Figure 25:
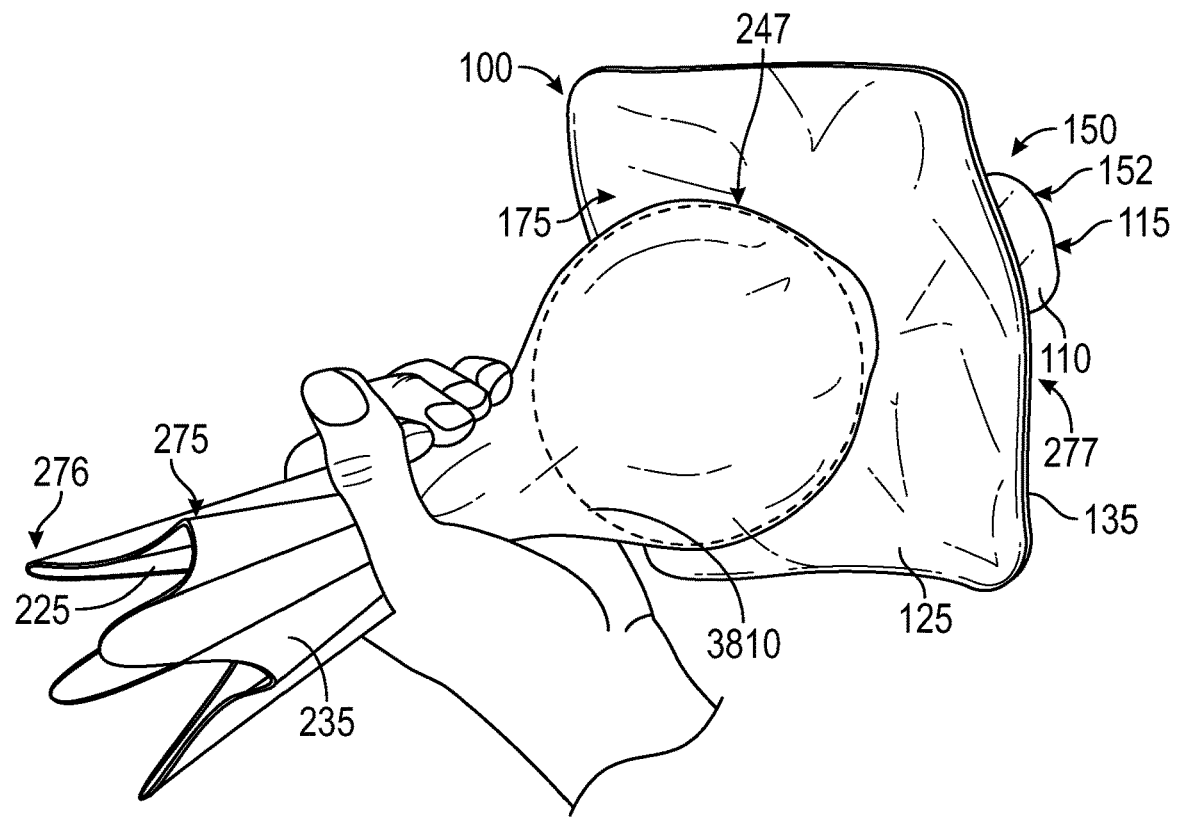
FIG. 25 is a rear diagrammatic view of the implant delivery device having a shielding member, a delivery member, and a base, and having an implant disposed in a conforming cavity formed by the delivery member and a base for engaging at least a portion of the skin of a subject adjacent to an incision, according to an exemplary embodiment of the present disclosure.

According to at least one aspect of the present disclosure, the implant delivery device 100 may include a shielding member 150 that has an inner bore 115 that is conical or an inner bore that is a combination of conical and tubular. For example, implant delivery device 100 may include a conical member 280, as shown in FIGS. 14-15. The conical member 280 may have an inner bore 285 similar to inner bore 115 of tubular member 150 except that the inner bore 185 of conical member 280 is tapered or has a variable (e.g., non-uniform) cross-sectional width over its predetermined length 196. Conical member 280 may have a proximal end 281 and a distal end 282. The proximal end 281 may have a larger cross-sectional width than the distal end 282 such that the cross-sectional width of the inner bore 285 of conical member 280 decreases along its predetermined length 296 from the proximal end 281 to the distal end 282. The outer bore 297 as defined by outer surface 210 of conical member 280 may also be conical or tapered such that the outer bore 297 has a greater cross-sectional width at the proximal end 281 than the distal end 282 of conical member 280. As shown in FIGS. 14-15, the proximal end 281 of conical member 280 may substantially overlie aperture 220 in delivery member 275 such that the inner bore 285 of the conical member 280 is continuous with the aperture 220 such that when an implant is inserted into aperture 220 of delivery member 275 it will be received in the proximal end 281 of inner bore 285 of the conical member 280. In at least some instances, the conical or tapered characteristics of conical member 280 may ease insertion of the implant into aperture 220 of delivery member 275 and facilitate transit of the implant to the implant pocket while being shielded from at least a portion of the dissection tunnel by shielding member 150 of implant delivery device 100.

In some instances, the shielding member 150 of implant delivery device 100 may have an inner bore 115 that is both tubular and conical. In such instances, the shielding member may comprise a tubular member 250 and a conical member 280, for example, as depicted in FIGS. 14-15. As shown in FIG. 14, the conical member 280 may comprises the proximal end 151 of the shielding member 150 while the tubular member 250 may comprise the distal end 152 of the shielding member 150. Accordingly, the proximal end 151 of the inner bore 115 of the shielding member 150 may have a variable cross-sectional width while the distal end 152 of the inner bore 115 may have a uniform cross-sectional width, as shown in FIGS. 14-15. As shown in FIGS. 14-15, the inner bore 285 of conical member 280 may have a greater cross-sectional width at the proximal end 151 of shielding member 150 (proximal end 281 of conical member 280) corresponding to the aperture 220 in delivery member 275 as compared to the opposite distal end 282 of the conical member 280, thus providing for easier insertion of the implant into the aperture 220 and shielding member 150.

As shown in FIGS. 14-15, the proximal end 281 of conical member 280 may be coupled with the lower surface 235 of delivery member 275 such that the inner bore 285 of the conical member 280 is substantially aligned with the aperture 220 of delivery member 275 so that the conical member 280 may receive the implant once the implant is inserted into aperture 220. The distal end 282 of conical member 280 may be coupled with the proximal end 251 of tubular member 250 such that the inner bore 285 of the conical member 280 is substantially aligned with the inner bore 215 of the tubular member 250 to form inner bore 115 of shielding member 150. Aperture 155 of shielding member 150 is formed in the distal end 252 of the tubular member 250. As shown in FIG. 15, the tubular member 250 may have a predetermined length 295 while the conical member may have a predetermined length 296. Therefore, in such cases, the predetermined length 165 of shielding member 150 comprises the predetermined length 295 of tubular member 250 together with the predetermined length 296 of conical member 280.

FIGS. 16-20 illustrate wrapping of implant 1100 by delivery member 275 as previously described, but for an implant delivery device 100 having a shielding member 150 that comprises both a tubular member 250 and a conical member 280, such as is shown in FIGS. 14-15.

In at least some instances, shielding member 150 may have an inner bore 115 that is conical. In such cases, the shielding member 150 may comprises a conical member 280 having an outer surface 210 and an inner bore 285. The proximal end 281 of conical member 280 may be coupled with the lower surface 235 of delivery member 275 while the distal end 282 of conical member 280 forms the aperture 155 of the shielding member 150. The proximal end 281 of conical member 280 may have a larger cross-sectional width than the distal end 282 such that the cross-sectional width of the inner bore 285 of conical member 280 decreases along its predetermined length 296 from the proximal end 281 to the distal end 282. The outer bore 298 as defined by outer surface 210 of conical member 280 may also be conical or tapered such that the outer bore 298 has a greater cross-sectional width at the proximal end 281 than the distal end 282 of conical member 280. The proximal end 281 of conical member 280 may substantially overlie aperture 220 in delivery member 275 such that the inner bore 285 of the conical member 280 is continuous with the aperture 220 such that when an implant is inserted into aperture 220 of delivery member 275 it will be received in the proximal end 281 of inner bore 285 of the conical member 280. In at least some instances, the conical or tapered characteristics of conical member 280 may ease insertion of the implant into aperture 220 of delivery member 275 and facilitate transit of the implant to the implant pocket while being shielded from at least a portion of the dissection tunnel by shielding member 150 of implant delivery device 100.

In some instances, the outer bore 195 as defined by outer surface 110 of shielding member 150 may have the same cross-sectional shape as the inner bore 115 of the shielding member 150. However, in other cases, the outer bore 195 of shielding member 150 may have a different cross-sectional shape than the inner bore 115 of the shielding member. For example, the outer bore 195 and outer surface 110 of shielding member 150 may have a tubular shape and cross-section with a uniform cross-sectional width, while the inner bore 115 is conical or a combination of tubular and conical.

Shielding member 150 may have an outer bore 195 as defined by outer surface 110 that is tubular, for example, characterized by a uniform cross-sectional width. However, the inner bore 115 of shielding member 150 may be frustoconical or conical, as defined by inner surface 105, having a variable cross-sectional width that is wider (greater) at the proximal end 151 of shielding member 150 and narrower (less) as the distal end 152 of the shielding member 150. In such cases, the conical inner bore 115 allows easy insertion of the implant at the proximal end 151 of the shielding member 150 while the narrower distal end 152 provides enough resistance to cause full extension of the shielding member into the dissection tunnel during implant insertion so as ensure effective shielding over the entire predetermined length 165 of the shielding member 150. Meanwhile, the tubular shape of the outer bore 195 and outer surface 110 of the shielding member 150 provides for easy insertion of the distal end 152 of the shielding member 150 into the dissection tunnel prior to implant insertion.

The implant delivery device 100 may optionally include a base 175, as shown in FIGS. 21-25. The base 175 may help to secure the shielding member 150 during delivery of the implant 1100 into the inner bore 115 of the shielding member 150 and ultimately to the implant pocket of the subject. The base 175 has an upper surface 125 and a lower surface 135. The lower surface 135 of the base 175 is operable to substantially engage with at least a portion of the skin adjacent to an incision leading to the implant pocket. The base 175 may have an aperture 120 formed therein which extends through the upper surface 125 and the lower surface 135 of the base 175. The base 175 may be coupled to the proximal end of the shielding member 150 such that the proximal end of the inner bore 115 of the shielding member is substantially aligned with the aperture 120 formed in the base 175. The aperture 120 formed in the base 175 is also co-aligned with the aperture 220 formed in the delivery member 275 thereby forming a collective aperture 222 through which the implant 1100 may pass when mechanical force is applied to the delivery member 275.

The base 175 and the delivery member 275 extend away from the collective aperture 222 and are detachably coupled along the radial length of the delivery member 275 so that the base 175 and the delivery member 275 may be peeled apart. However, the base 175 and the delivery member 275 maintain a coupling along the circumference of the collective aperture 222. In at least some instances, the base 175 and the delivery member 275 are heat sealed together along the circumference of the collective aperture 222. Therefore, when an implant 1100 is disposed in the conforming cavity 247 or pocket of the delivery member 275 and mechanical force is applied to the delivery member 275, the implant 1100 may be squeezed from the conforming cavity 247 and through the collective aperture 222 formed into the delivery member 275 and base 175 and into the proximal end of the inner bore 115 of the shielding member 150 and into the implant pocket in the subject.

The present disclosure also provides a system that includes the implant delivery device 100 and an implant 1100 capable of being inserted by the implant delivery device 100. The present disclosure also provides a kit that includes the implant delivery device 100 packaged together with an implant 1100 capable of being inserted by the implant delivery device 100.

The apparatus, systems, kits, and methods of the present disclosure may be used with any implants. For example, the implant may be, but is not limited to, filled implants, unfilled implants, saline implants, silicone gel implants, textured implants, smooth implants, highly cohesive silicone gel implants, oil-filled implants, and prosthesis implants. The subject may be any subject in need of an implant. The subject may be, for example, but not limited to, a mammal or a human. In some cases, the subject may be a human and the implant may be a breast implant.

While FIGS. 26-36 illustrate methods of using the presently disclosed apparatus and techniques of using the apparatus for inserting a breast implant into a human subject, one of skill in the art will understand and appreciated the depicted methods may be used for any type of implant in any type of subject in need thereof. FIGS. 26-34 illustrate methods for inserting an implant into a surgically-created implant pocket in a subject using the implant delivery device 100 disclosed herein. While the case of a periareolar incision and implant insertion is shown, the presently disclosed methods are suitable for use with any implant insertion or incision-type, including inframammary incision and implant insertion.

Figure 26:
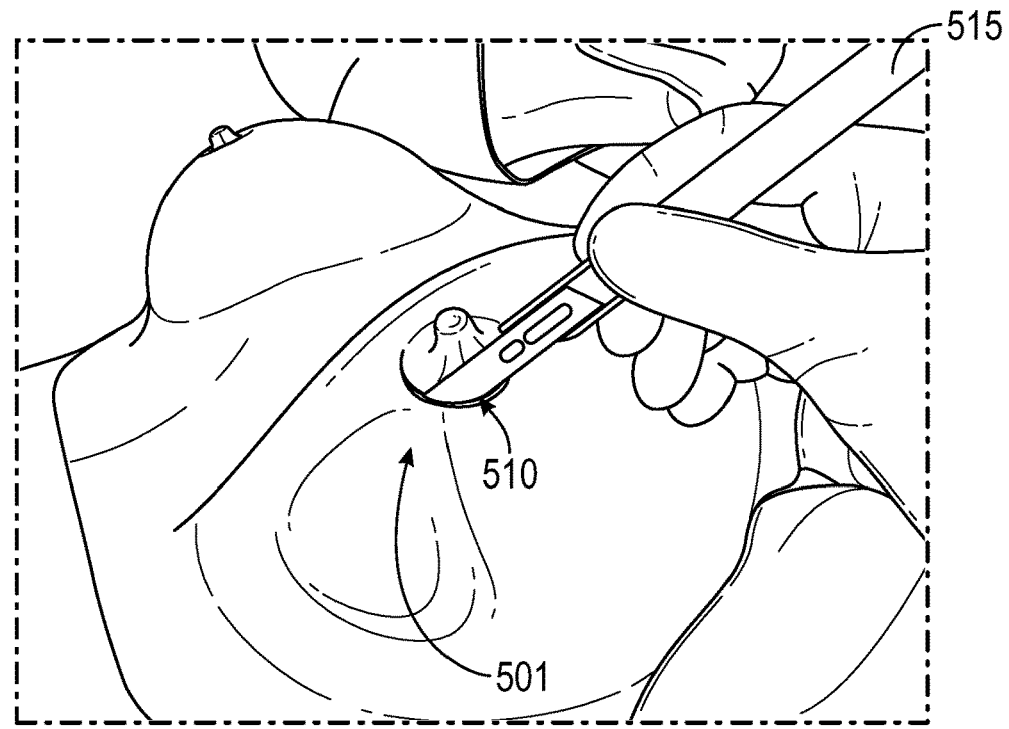
FIG. 26 is an illustration depicting the creation of a periareolar incision in the breast of a subject; according to an exemplary embodiment of the present disclosure.

In order for the implant to be inserted into the surgically-created implant pocket it must first pass through the incision in the skin of the subject and through the dissection tunnel connecting the implant pocket to the incision. As depicted in FIG. 26, a periareolar incision 510 in the skin 501 of the subject is created by scalpel 515.

Figure 27:
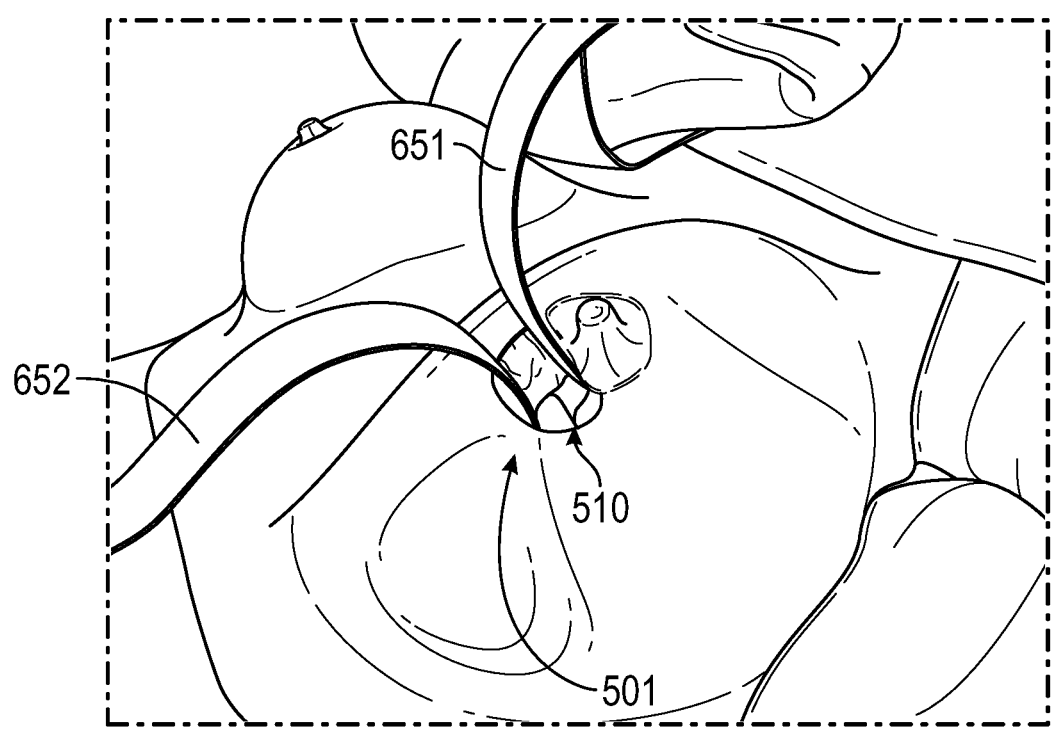
FIG. 27 is an illustration depicting the opening of the periareolar incision using two retractors, according to an exemplary embodiment of the present disclosure.

FIG. 27 depicts the use of retractors 651, 652 to open the periareolar incision 510 and to facilitate full surgical dissection of the implant pocket and the dissection tunnel connecting the implant pocket to the incision. Implant delivery device 100 is a delivery device rather than a retractor and is not capable of dilating the incision or holding open the incision during use like a retractor. However, unlike a retractor, the shielding member 150 of implant delivery device 100 is much quicker and easier to insert into the incision and dissection tunnel and therefore requires less manipulation. The less required manipulation and speed and ease of use of device 100 results in less contamination risk to the implant and greater effectiveness of biofilm shielding. Additionally, since the distal end 152 of the shielding member 150 does not include or require a retracting member, device 100 provides for easy adjustment of the predetermined length 165 prior to use by cutting the distal end 152 of the shielding member 150 to the desired predetermined length 165. Implant delivery device 100 may be used in conjunction with separate retractors, such as retractors 651, 652 shown in FIG. 27, which allows the dissection tunnel and implant pocket to be opened up and reduces the resistance of the implant to insertion as well as reduces the external force required for insertion and delivery of the implant to the implant pocket.

While FIG. 27 depicts the use of retractors during use of implant delivery device 100, one of skill in the art will understand that in other instances, device 100 may be used without retractors particularly depending on the type, nature, and size of the implant being inserted.

Additionally, shielding member 150 may be stretchable or comprise a stretchable material providing for expansion of the dissection tunnel during insertion of the implant into the inner bore 115 of the stretchable shielding member 150. In such cases, the shielding member 150 may stretch to accommodate the implant as well as to engage the walls of the dissection tunnel so that the dissection tunnel is opened sufficient for implant insertion while the shielding member 150 shields the implant from the dissection tunnel or a portion thereof. The stretchability of the shielding member 150 also provides the advantage that when retractors are placed inside of the shielding member 150 during use to open up the dissection tunnel, the shielding member 150 may stretch to allow greater opening of the dissection tunnel as well as engagement of the walls of the dissection tunnel thereby providing effective shielding for the implant as well as reducing the frictional forces associated with implant insertion. The stretchability of the shielding member 150 also provides the advantage of stretching during insertion of the implant so as to reduce the forces associated with implant insertion and to facilitate transit of the implant to the implant pocket while providing the implant shielding function, whether retractors are placed within shielding member 150, placed between the shielding member 150 and the walls of the dissection tunnel, or not used at all.

Figure 28:
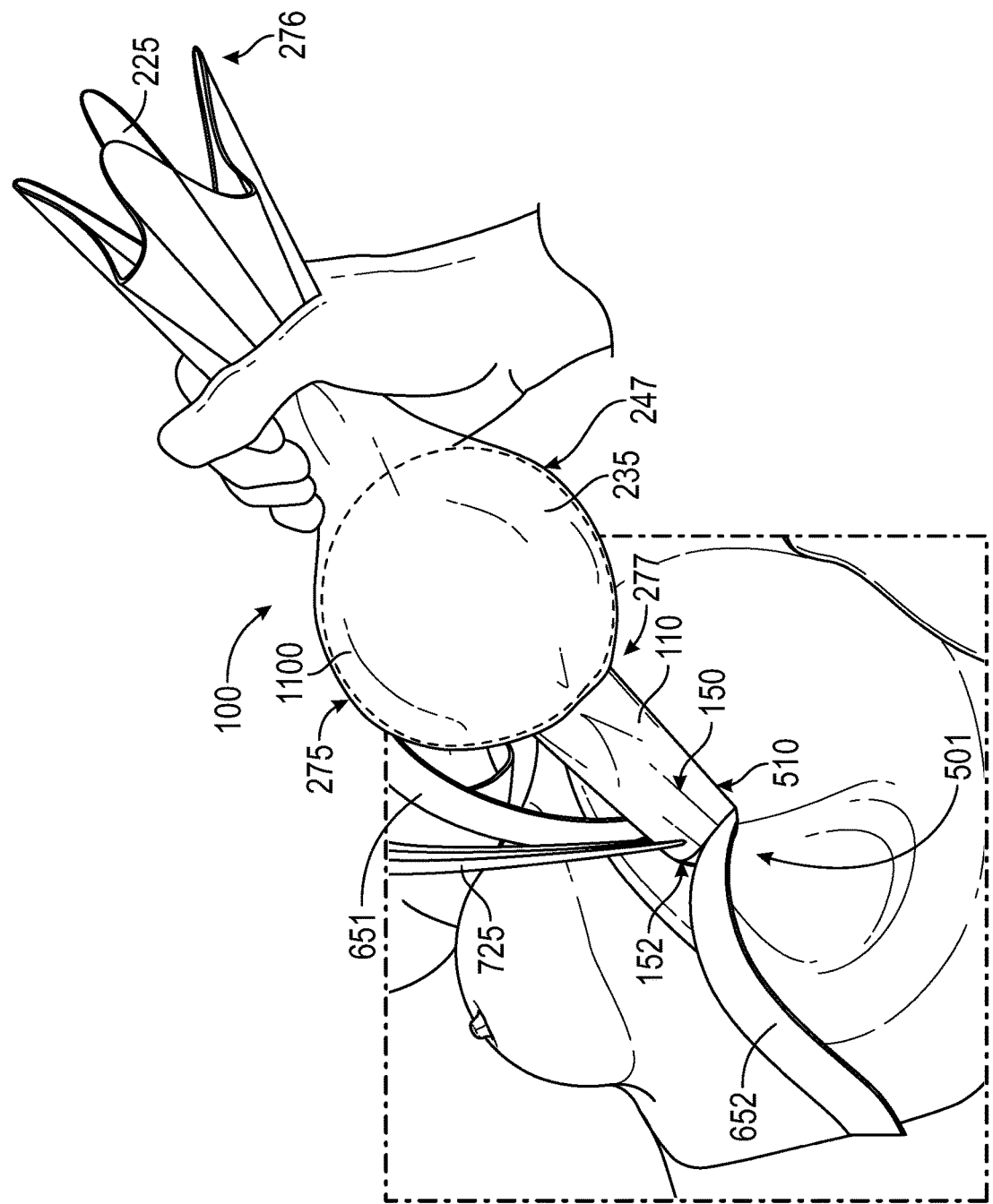
FIG. 28 is an illustration depicting insertion of the distal end of the shielding member of the implant delivery device into the dissection tunnel connecting the periareolar incision to the surgically-created implant pocket while the implant is disposed in a conforming cavity formed by the delivery member, according to an exemplary embodiment of the present disclosure.

As depicted in FIG. 27, the incision 510 and the dissection tunnel are further opened using retractors 651, 652 to facilitate insertion of the shielding member 150 of device 100. As shown in FIG. 28, the implant delivery device 100 loaded with implant 1100 in a conforming cavity 247 formed by delivery member 275 is manipulated to the incision 510 by the surgeon and the distal end 152 of the shielding member 150 is inserted through the incision 510 and into the dissection tunnel using any suitable sterile insertion tool, such as forceps 725. As shown in FIG. 28, the shielding member 150 is further inserted into the dissection tunnel such that the distal end 152 of the shielding member 150 is received in at least a portion of the dissection tunnel or the implant pocket.

The distal end 152 of the shielding member 150 is generally inserted into the dissection tunnel to a depth greater than 1 cm below the incision so as to sufficiently shield the implant during insertion into the dissection tunnel and implant pocket. In general, it is not necessary for the shielding member 150 to shield the implant from the entire length of the dissection tunnel since often only a portion of the dissection tunnel is formed through breast tissue (glandular tissue) which may be colonized by microbes, thereby posing a risk of microbial contamination to the otherwise sterile implant. Often, the remaining portions of the dissection tunnel are formed through sterile muscle or adipose tissue that do not pose a significant contamination risk to the implant during its transit to the implant pocket. Generally, the upper dissection tunnel comprises breast tissue and/or glandular tissue while the lower dissection tunnel comprises tissue other than breast or glandular tissue, such as muscle or adipose tissue. As used herein, the upper dissection tunnel refers to the portion of the dissection tunnel beginning at the incision in the skin of the patient and extending downward for so long as the walls of the dissection tunnel are formed through breast and/or glandular tissue. The lower dissection tunnel, as used herein, refers to the portion of the dissection tunnel beginning at the first instance of tissue other than breast and/or glandular tissue, such as muscle or adipose tissue and extending to the implant pocket. Therefore, the upper dissection tunnel is the upper most portion of the dissection tunnel connecting the incision in the skin of the patient to the lower dissection tunnel which in turn extends to the implant pocket. The length of the upper dissection tunnel can be measured intraoperatively and used to determine the predetermined length of the inner bore 115 and shielding member 150. In at least some instances, the distal end 152 of shielding member 150 is inserted into the dissection tunnel such that the entire length of the upper dissection tunnel is shielded from the implant during transit of the implant to the implant pocket. In such cases, the distal end 152 is inserted into the dissection tunnel to a depth equal to or greater than the length of the upper dissection tunnel. In other instances, the distal end 152 may be inserted into the dissection tunnel such that at least a portion of the upper dissection tunnel is shielded from the implant during transit of the implant to the implant pocket.

In at least some instances, the distal end 152 of the shielding member 150 is inserted greater than 1.5 cm, or greater than 2 cm, or greater than 2.5 cm, or greater than 3 cm, or greater than 3.5 cm, or greater than 4 cm, or greater than 4.5 cm, or greater than 5 cm, or greater than 5.5 cm, or greater than 6 cm, or greater than 6.5 cm, or greater than 7 cm, or greater than 7.5 cm, or greater than 8 cm, below the incision. In at least some instances, the distal end 152 of the shielding member 150 is inserted into the dissection tunnel to a depth of from about 2 cm to about 10 cm, or from about 3 cm to about 10 cm, or from about 2 cm to about 8 cm, or from about 2 cm to about 5 cm, or from about 3 cm to about 8 cm, below the incision. The depth of insertion will generally depend on the size of the implant used, the location of the incision, and the characteristics of the subject's breast. In at least some instances, insertion of the implant into the shielding member 150 may extend the distal end 152 of the shielding member 150 deeper into the dissection tunnel such that the implant is shielded from a greater portion of the dissection tunnel during its transit to the implant pocket.

In at least some instances, the predetermined length 165 of the inner bore 115 of the shielding member 150 may be adjusted based on the desired depth of insertion into the dissection tunnel. In such instances, intraoperative measurements of the length of the dissection tunnel may be used to determine the predetermined length 165 of the inner bore 115 of the shielding member 150 necessary to shield the implant from at least a portion of the dissection tunnel. In such cases, the predetermined length 165 of the inner bore 115 may be adjusted or cut to a predetermined length 165 equal to or less than the measured length of the dissection tunnel.

Figure 29:
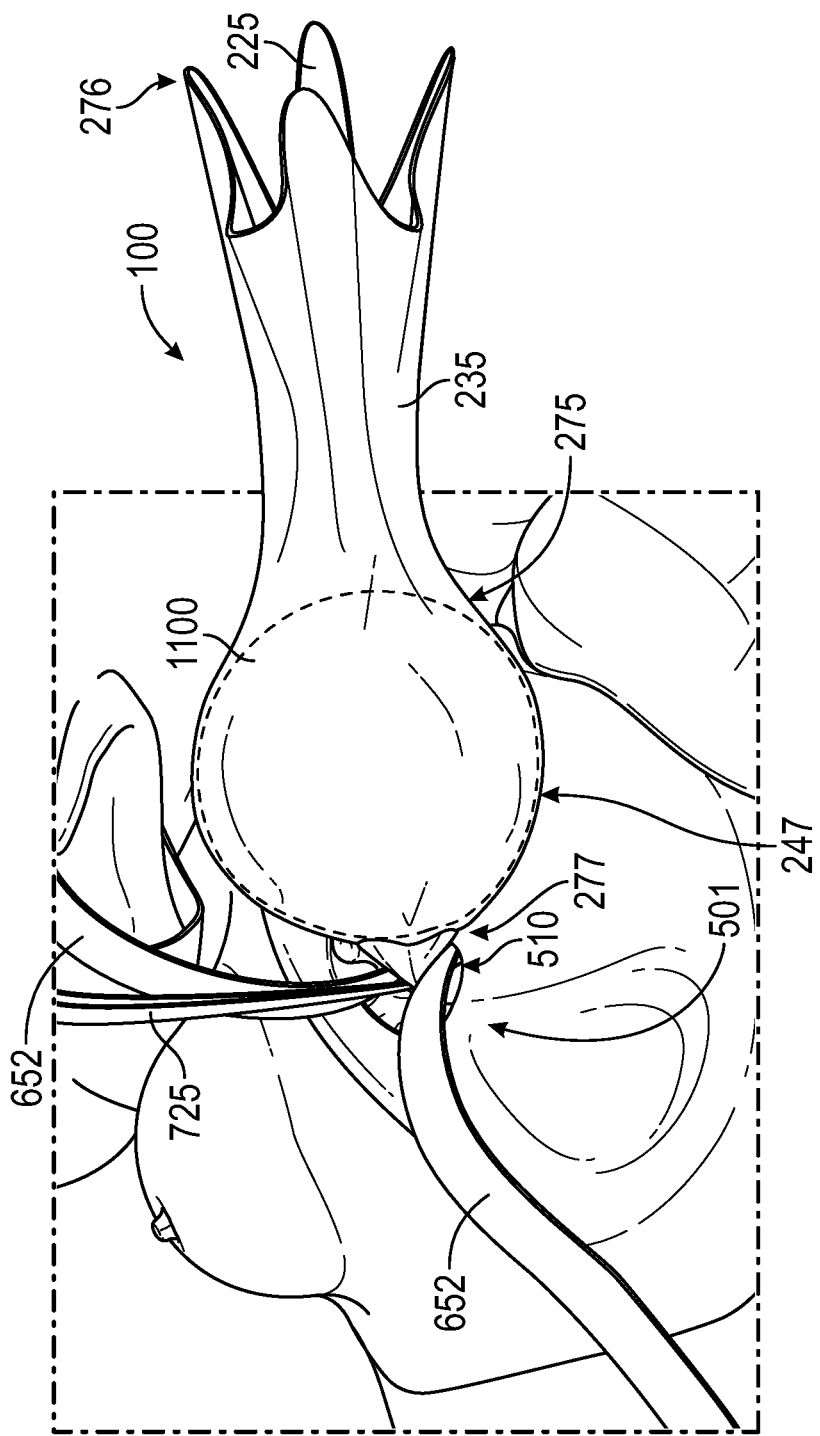
FIG. 29 is an illustration depicting further insertion of the shielding member into the dissection tunnel while the implant is disposed in a conforming cavity formed by the delivery member, according to an exemplary embodiment of the present disclosure.
Figure 30:
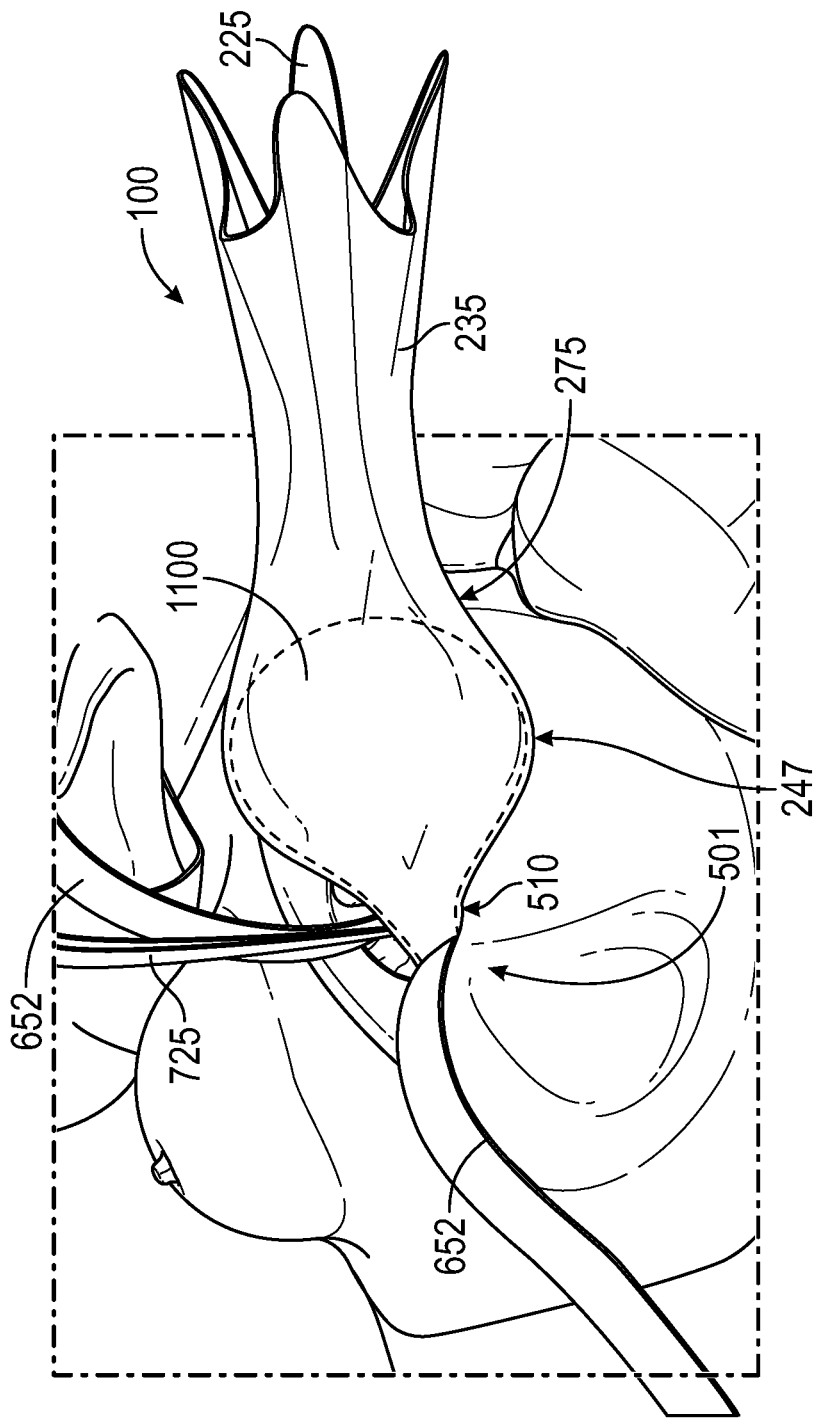
FIG. 30 is an illustration depicting the application of mechanical forces to the lower surface of the delivery member so as to propel the implant from the conforming cavity formed by the delivery member through the aperture formed in the delivery member and through the shielding member into the implant pocket in the subject, according to an exemplary embodiment of the present disclosure.
Figure 31:
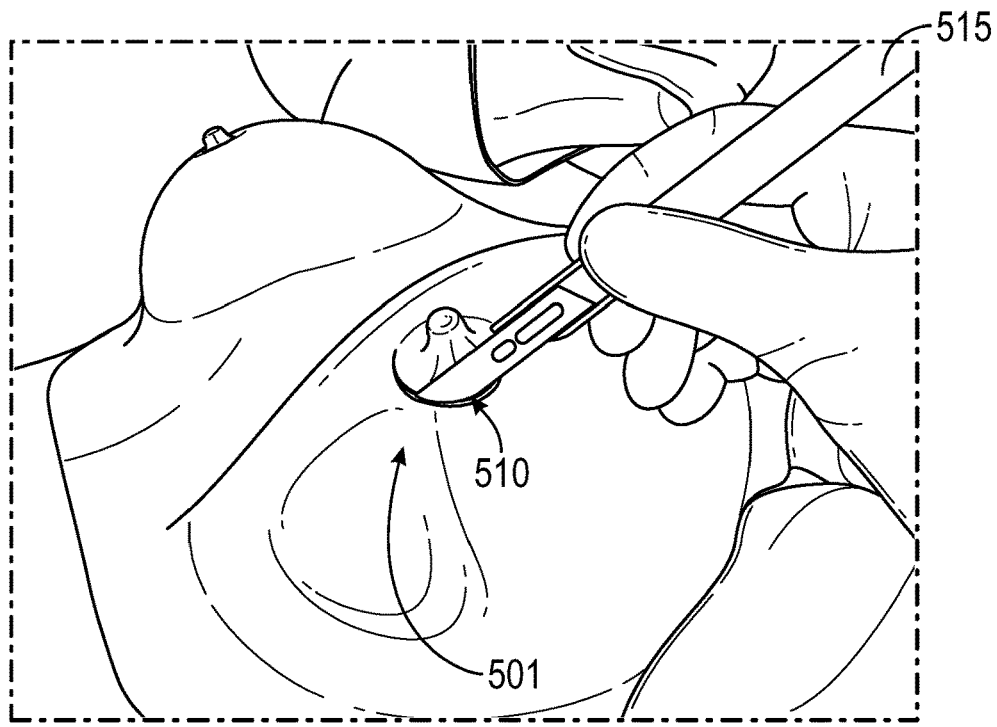
FIG. 31 is an illustration depicting the creation of a periareolar incision in the breast of a subject; according to an exemplary embodiment of the present disclosure.
Figure 32:
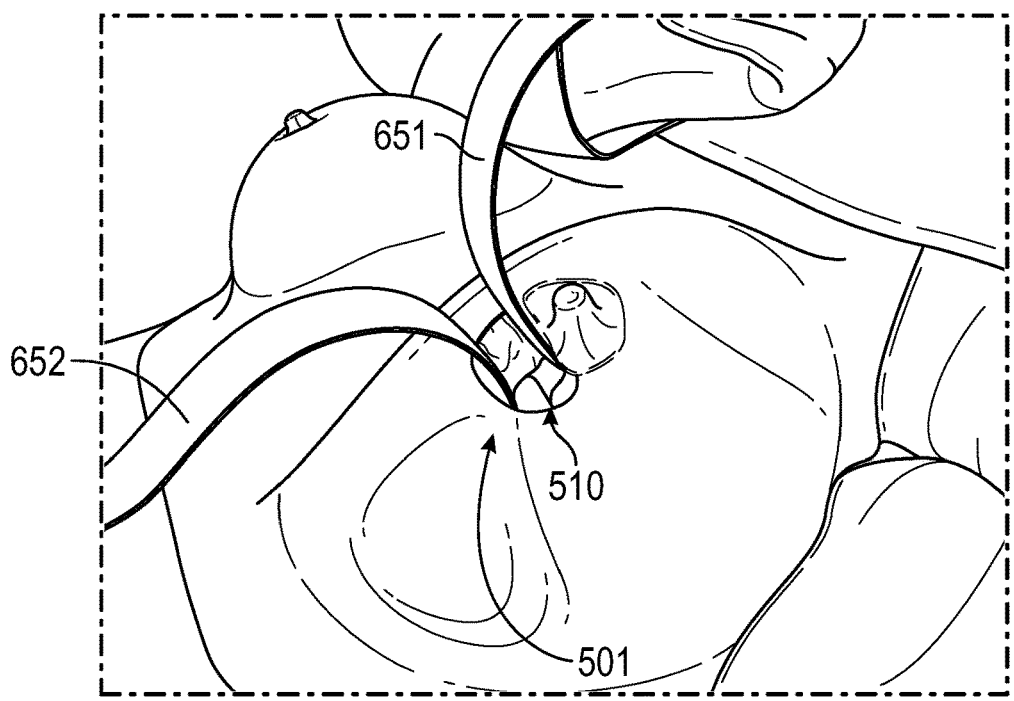
FIG. 32 is an illustration depicting the opening of the periareolar incision using two retractors, according to an exemplary embodiment of the present disclosure.

As shown in FIGS. 29 and 30, once the shielding member 150 is sufficiently inserted into the dissection tunnel, mechanical force may be applied to the lower surface 235 of the delivery member 275 so that the implant 1100 is translated, propelled, or squeezed from the conforming cavity 247 formed in the delivery member 275 and through the aperture 220 formed into the delivery member 275 and into the proximal end of the inner bore 115 of the shielding member 150 and into the implant pocket in the subject.

The application of mechanical force to the lower surface 235 of the delivery member 275 imparts a compressive force on the delivery member 275 above the implant 1100 (e.g., between the proximal end 276 of the delivery member and the conforming cavity) so as to propel the implant 1100 from the delivery member 275 and into the shielding member 150 and into the implant pocket of the subject. In particular, the mechanical force may be applied to the portion of the lower surface 235 of the delivery member 275 corresponding to the portion of the conforming cavity 247 nearest the proximal end 276 of delivery member 275 so as to impart compressive forces on the portion of the implant 1100 closest to the proximal end 276 of the delivery member thereby causing the implant 1100 to translate toward and through aperture 220 and the inner bore 115 of shielding member 150 and ultimately into the implant pocket in the subject. In other instances, the mechanical force may be applied to the lower surface 235 of the delivery member 275 between the proximal end 276 of the delivery member and the conforming cavity 247 so as to impart compressive force above the implant 1100 (e.g., between the proximal end 276 of the delivery member and the conforming cavity) so as to propel the implant 1100 through aperture 220 and inner bore 115 of shielding member 150 and into the implant pocket in the subject. In at least some instances, mechanical force may be applied to the lower surface 235 of the delivery member 275 by the user or surgeon sliding the hand from the proximal end 276 of the delivery member 276 towards the distal end 277 of the delivery member 275 such that compressive force is imparted to the conforming cavity 247 and/or the implant 1100 disposed within the conforming cavity 247, thereby causing the implant 1100 to be propelled from the conforming cavity 247 to the inner bore 115 of the shielding member 150 and into the implant pocket in the subject. In other instances, the proximal end 276 of the delivery member 275 may be twisted until sufficient compressive force is exerted on the conforming cavity 247 and/or the implant 1100 disposed within the conforming cavity 247, such that the implant 1100 is propelled from the conforming cavity 247 into the inner bore 115 of the shielding member 150 and into the implant pocket in the subject.

Figure 33:
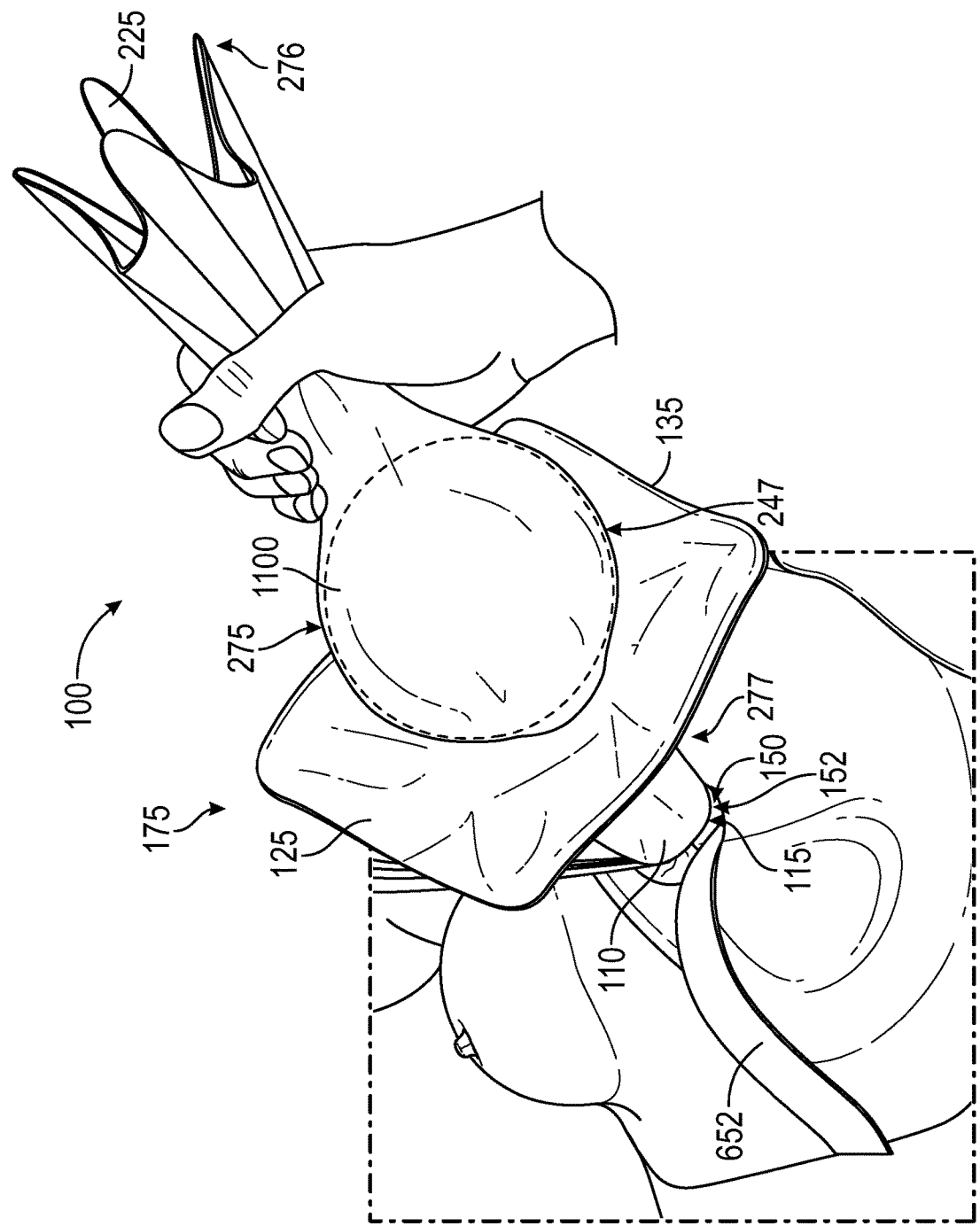
FIG. 33 is an illustration depicting insertion of the distal end of the shielding member of an implant delivery device having a base into the dissection tunnel connecting the periareolar incision to the surgically-created implant pocket while the implant is disposed in a conforming cavity formed by the delivery member, according to an exemplary embodiment of the present disclosure.
Figure 34:
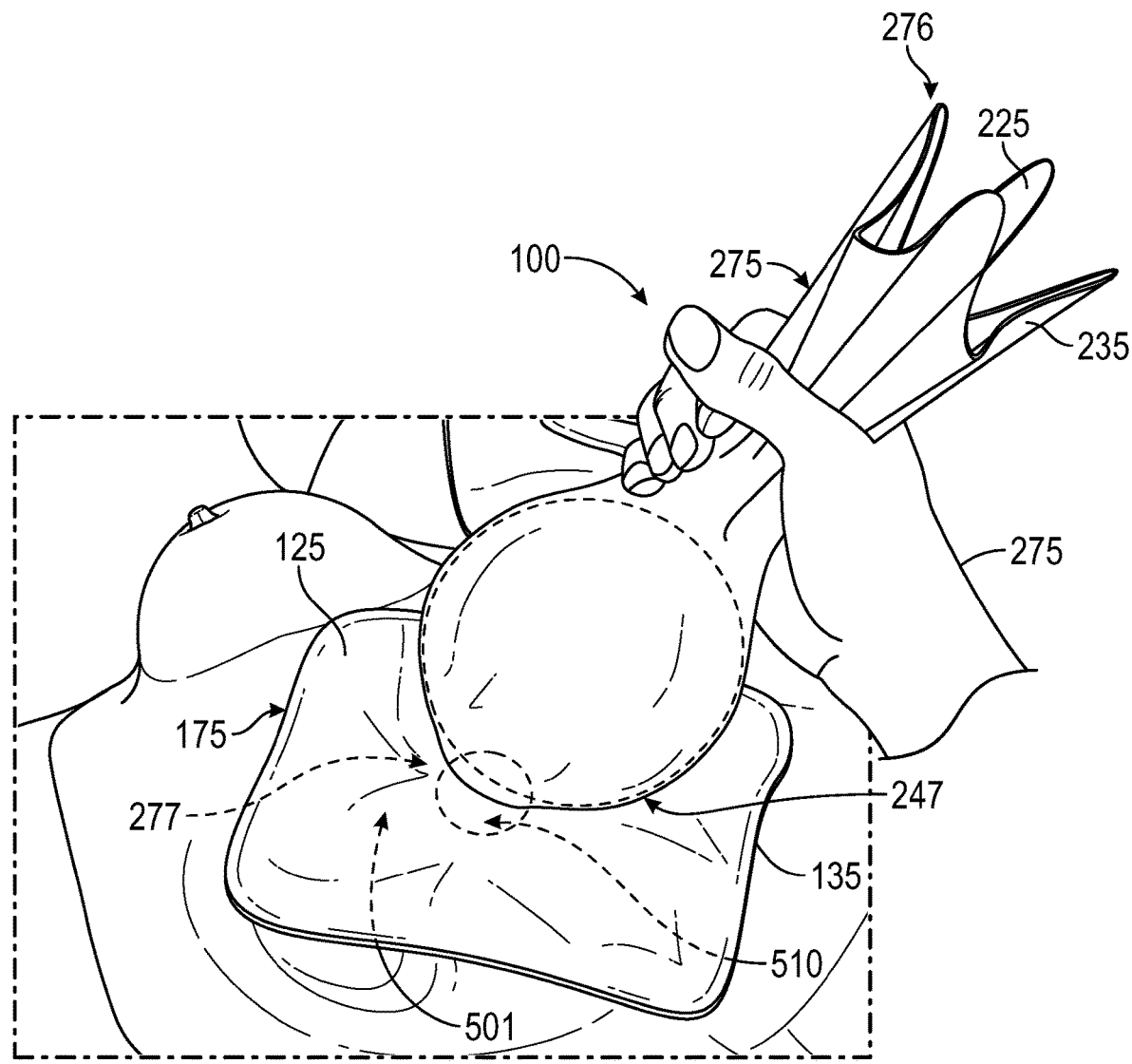
FIG. 34 is an illustration depicting further insertion of the shielding member into the dissection tunnel and engagement of the lower surface of the base with the skin of the subject adjacent to the incision while the implant is disposed in a conforming cavity formed by the delivery member, according to an exemplary embodiment of the present disclosure.

FIGS. 31-34 illustrate a similar method of implant delivery and insertion as described for FIGS. 26-30, but instead using an implant delivery device 100 having an optional base 175. In such instances, as shown in FIGS. 33-34, once the shielding member 150 is sufficiently inserted into the dissection tunnel, the base 175 of device 100 may be engaged with the surface of the skin 501 of the subject so that device 100 may be anchored in place during insertion of the implant. As shown in FIG. 34, the lower surface 135 (opposite of upper surface 125) of base 175 is engaged with the skin 501 of the subject. As described above, the lower surface 135 of the base 175 may be engaged with the skin 501 of the subject by any number of techniques, including, but not limited to, frictional engagement by a textured surface or by wetting with a suitable liquid and by attaching to the skin 501 of the subject using an adhesive exposed by the removal of a removable backing. Once apparatus 100 is securely engaged with the skin 501 of the subject, the collective aperture 222 and inner bore 115 substantially overlie at least a portion of the incision. The implant 1100 is then inserted by the application of mechanical force to the lower surface 235 of the delivery member 275 so that the implant 1100 is translated, propelled, or squeezed from the conforming cavity 247 formed in the delivery member 275 and through the collective aperture 222 formed into the delivery member 275 and base 175 and into the proximal end of the inner bore 115 of the shielding member 150 and into the implant pocket in the subject.

Figure 35:
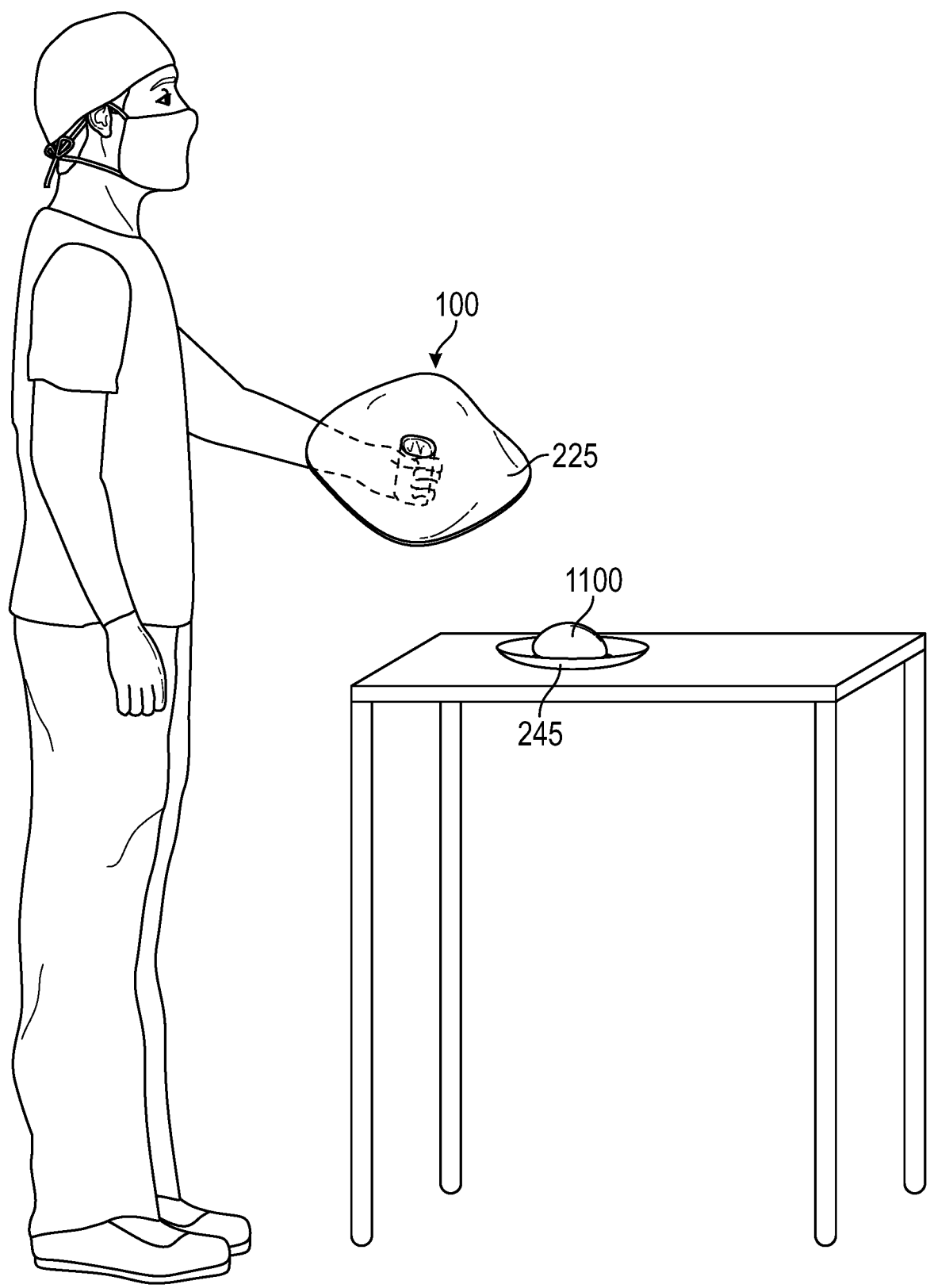
FIG. 35 is an illustration depicting the use of the delivery member to pick up an implant from a sterile bowl followed by wrapping the implant in the delivery member so as to form a conforming cavity around the implant, according to an exemplary embodiment of the present disclosure.
Figure 36:
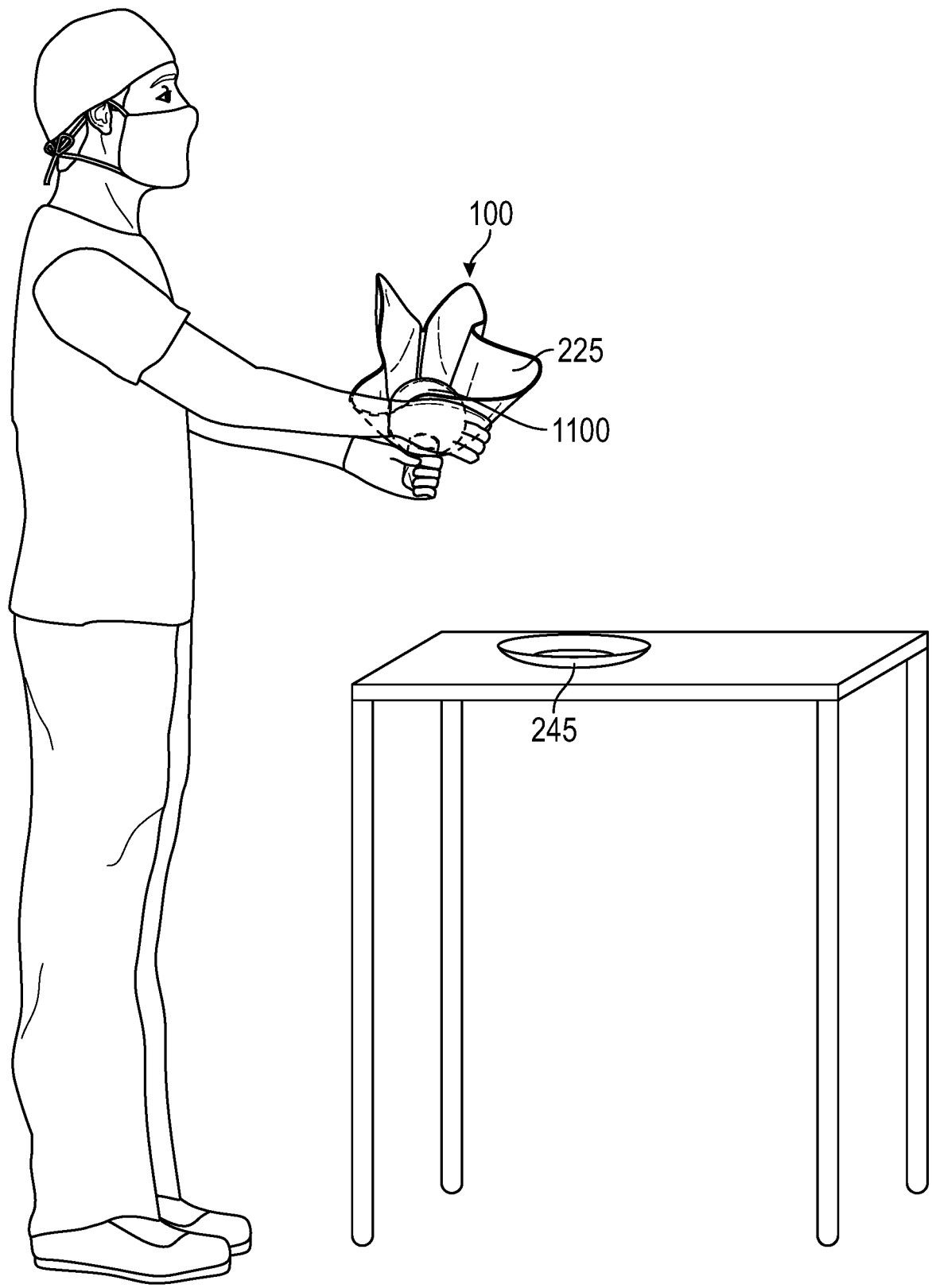
FIG. 36 is an illustration depicting wrapping the implant in the delivery member so as to form a conforming cavity around the implant after picking up the implant from the sterile dish, according to an exemplary embodiment of the present disclosure.

Commonly, implants are provided to surgeons in sterile double bowl packaging in which the sterile implant is in a first bowl secured by a plastic sheet or packaging. The first bowl is placed in a second sterile bowl also secured by a plastic sheet or packaging. Therefore, the sterile implant is typically disposed in a bowl, such as bowl 245 shown in FIG. 35, prior to insertion of the implant into the subject. As shown in FIGS. 35-36, the implant delivery device 100 may be used to pick up a sterile implant from bowl 245 thereby loading the implant delivery device 100 with implant 1100 for no touch delivery and protected insertion of the implant. In such instances, the implant 110 may be loaded into the implant delivery device 100 by lifting it up from its sterile bowl packaging or by loading it from a sterile bowl in common use in the surgical setting. For instance, the implant 1100 may be disposed in a dish or bowl 245 in common use in the surgical setting. The surgeon or assistant may then load the implant delivery device 100 by wrapping the sterile upper surface 225 of delivery member 275 around the implant 1100 sitting in the dish or bowl 245 and picking up the implant within the delivery member 275 wrapping.

Alternatively, the sterile implant 1100 may be poured from the sterile bowl, such as bowl 245 shown in FIG. 35, directly onto the upper surface 225 of the delivery member 275 without touching implant 1100. Once the implant is poured from the sterile bowl on the upper surface 225 of the delivery member 275, the implant 1100 may be wrapped in the delivery member 275 such that the implant 1100 is loaded in the implant delivery device 100 with implant 1100 disposed in the conforming cavity 247 formed by the delivery member 275, as shown, for example in FIGS. 1-8.

Figure 37:
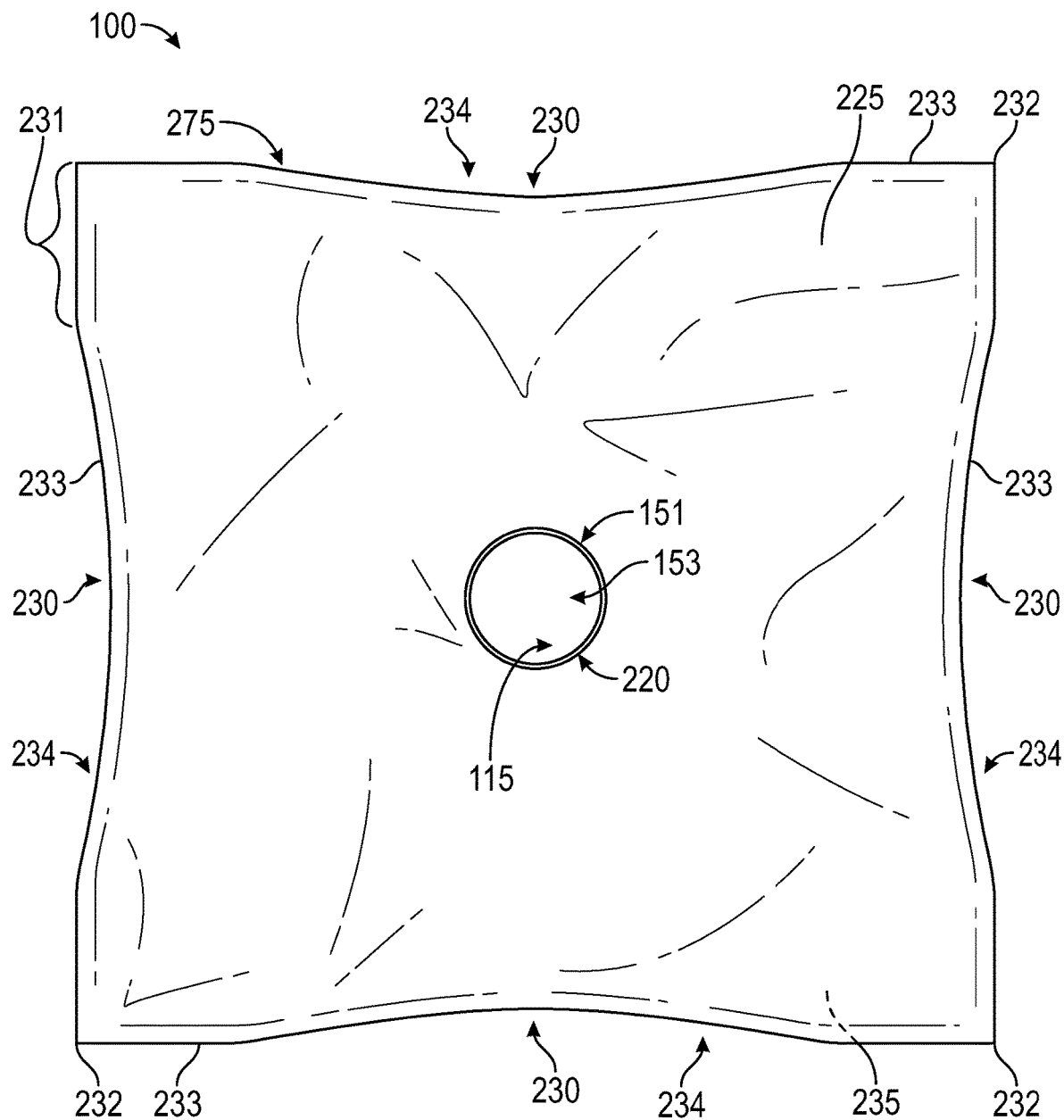
FIG. 37 is a rear planar view of the implant delivery device that includes a delivery member having a radius of curvature along one or more outer edges, according to an exemplary embodiment of the present disclosure.

In order to facilitate wrapping of the implant in the delivery member 275 of the implant delivery device 100, the delivery member 275 may include a plurality of lengths 233 with one or more of the lengths 233 having a radius of curvature 230, as shown in FIG. 37. As depicted in FIG. 37, the delivery member 275 may include a plurality of lengths 233 defining the outer edge 234 of the delivery member 275. As shown in FIG. 37, each of the lengths 233 may have a radius of curvature 230 which have been found to facilitate the wrapping of the implant in delivery member 275 in order to form a conforming cavity around the implant. As used herein, the term "radius of curvature" refers to a curve or a segment of a circle or an ellipse. Each of lengths 233 may have a radius of curvature, as depicted in FIG. 37, or only one or more of the lengths 233 may have a radius of curvature. The delivery member 275 may be substantially rectangular as shown in FIG. 37, or may have any polygonal shape.

As shown in FIG. 37, the plurality of lengths 233 intersect an adjacent length at a vertex 232 such that delivery member 275 includes a plurality of verteces 232. In some instances, the radius of curvature 230 may begin and end at the verteces 232 such that the radius of curvature 230 comprises the entire length of a length 233. In other instances, the radius of curvature 230 may begin or end at a predetermined distance 231 for a vertex 232, as shown in FIG. 37.

Figure 38:
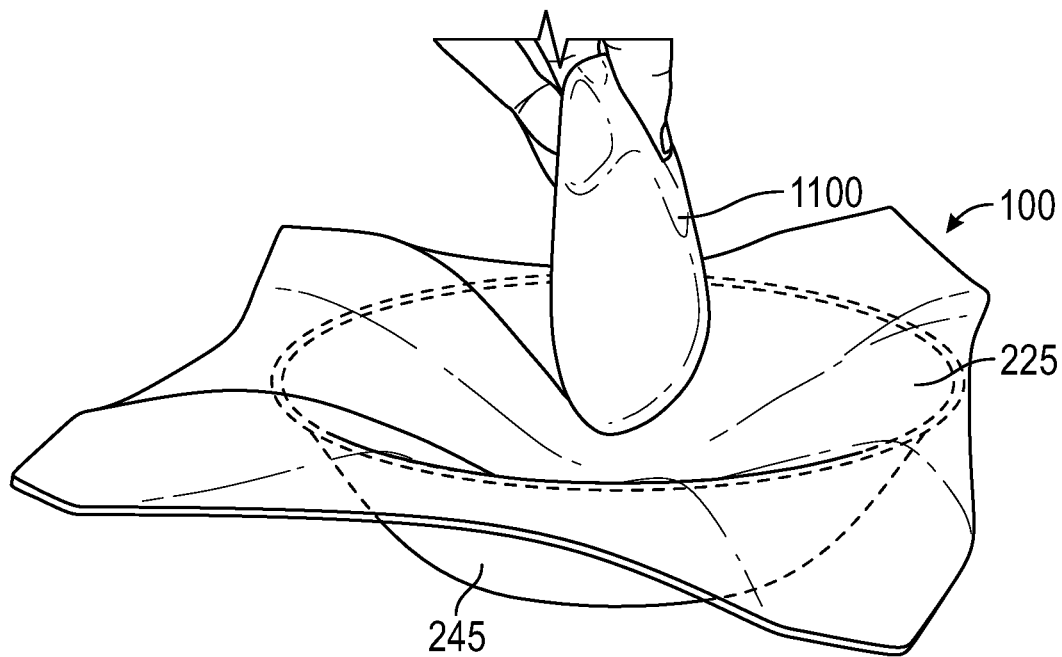
FIG. 38 is an illustration depicting a method of placing the implant on the upper surface of the delivery member while the implant delivery device is disposed in a sterile bowl in order to facilitate wrapping of the implant in the delivery member so as to form a conforming cavity around the implant, according to an exemplary embodiment of the present disclosure.
Figure 39:
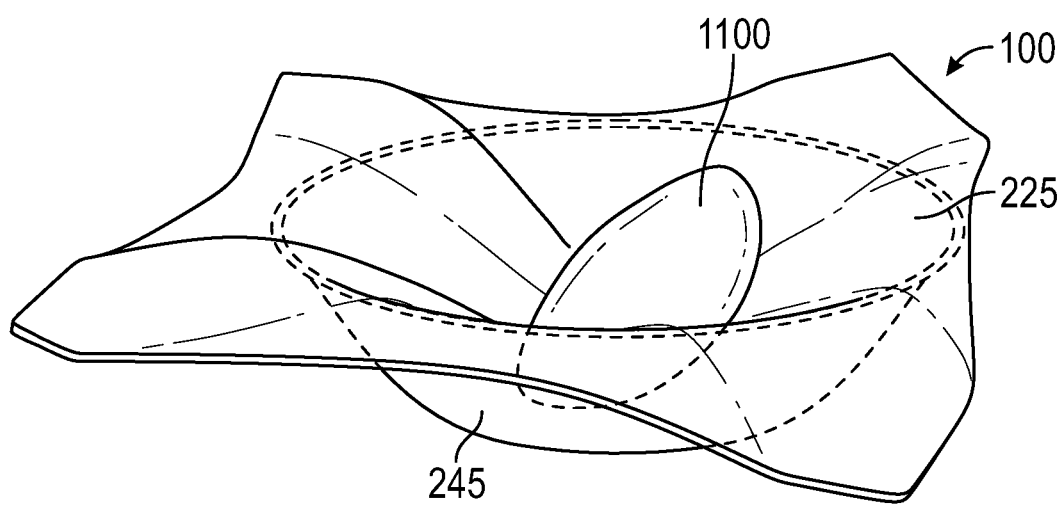
FIG. 39 is an illustration depicting a method of wrapping the implant in the delivery member while the implant delivery device is disposed in a sterile bowl, according to an exemplary embodiment of the present disclosure.

FIGS. 38-39 depict a method of loading the implant delivery device 100 with an implant by placing the implant delivery device 100 in a bowl or dish 245 with the upper surface 225 of the delivery member 275 facing up. The implant 1100 is then delivered from sterile implant packaging without touching the implant and using sterile technique, and then the implant is placed on the upper surface 235 of the delivery member 275 while the implant delivery device 100 is disposed in a sterile bowl in order to facilitate wrapping of the implant 1100 in the delivery member 275 so as to form a conforming cavity around the implant 1100.

STATEMENTS OF THE PRESENT DISCLOSURE

Numerous examples are provided herein to enhance understanding of the present disclosure. A specific set of statements are provided as follows.

Statement 1: A device for delivering an implant into a surgically-created implant pocket in a subject, the device comprising: a delivery member having an upper surface and a lower surface, the delivery member having an aperture formed therein and extending through the upper surface and the lower surface; and a shielding member coupled with the delivery member, the shielding member having an inner bore extending longitudinally between a proximal end having a proximal opening and a distal end having a distal opening, the inner bore extending a predetermined length away from the lower surface of the delivery member; wherein the proximal end of the shielding member is coupled with the delivery member and the inner bore is substantially aligned with the aperture formed in the delivery member; wherein the delivery member is operable to wrap around the implant to form a conforming cavity around the implant that conforms to the shape of the implant; and wherein the inner bore is operable to receive the implant therethrough when mechanical force is applied to the lower surface of the delivery member.

Statement 2: The device according to Statement 1, wherein the delivery member is operable to propel the implant from the conforming cavity into the implant pocket in the subject upon the application of mechanical force to the lower surface of the delivery member.

Statement 3: The device according to Statement 1, wherein the delivery member is operable to propel the implant from the conforming cavity through the aperture formed in the delivery member and into the inner bore of the shielding member upon the application of mechanical force to the lower surface of the delivery member.

Statement 4: The device according to any one of the preceding Statements 1-3, wherein the conforming cavity is formed by the upper surface of the delivery member in contact with the implant.

Statement 5: The device according to any one of the preceding Statements 1-4, wherein the delivery member comprises a plurality of lengths defining the outer edge of the delivery member, each of the lengths comprising a radius of curvature.

Statement 6: The device according to Statement 5, wherein the radius of curvature comprises a curve or a segment of a circle or an ellipse.

Statement 7: The device according to Statement 6, wherein each of the plurality of lengths intersects an adjacent length at a vertex, the radius of curvature beginning and ending at one of the verteces and extending along the entire length of each of the plurality of lengths.

Statement 8: The device according to Statement 6, wherein each of the plurality of lengths intersects an adjacent length at a vertex, the radius of curvature beginning and ending along the length at a predetermined distance from the vertex.

Statement 9: The device according to any one of the preceding Statements 1-4, wherein the delivery member is substantially rectangular and comprises four lengths defining the outer edge of the delivery member.

Statement 10: The device according to Statement 9, wherein each of the four lengths comprises a radius of curvature.

Statement 11: The device according to Statement 10, wherein the radius of curvature comprises a curve or a segment of a circle or an ellipse.

Statement 12: The device according to Statement 11, wherein each of the four lengths intersects an adjacent length at a vertex, the radius of curvature beginning and ending at each of the vertices and extending along the entire length of each of the plurality of lengths.

Statement 13: The device according to Statement 11, wherein each of the four lengths intersects an adjacent length at a vertex, the radius of curvature beginning and ending along each of the four lengths at a predetermined distance from the vertex.

Statement 14: The device according to any one of the preceding Statements 9-13, wherein each of the four lengths are equal in length.

Statement 15: The device according to any one of the preceding Statements 1-14, wherein the proximal end of the shielding member is coupled with the lower surface of the delivery member.

Statement 16: The device according to any one of the preceding Statements 1-15, wherein the delivery member is operable to receive any size implant in common use.

Statement 17: The device according to any one of the preceding Statements 1-16, wherein the delivery member does not comprise an aperture for receiving the implant into the delivery device.

Statement 18: The device according to any one of the Statements 1-16, wherein the delivery member does not comprise an aperture through which an implant may be loaded into the delivery device.

Statement 19: The device according to any one of the preceding Statements 1-18, wherein the delivery member does not comprise a preformed conforming cavity.

Statement 20: The device according to any one of the preceding Statements 1-19, wherein the delivery member is operable to conform to the dimensions of the implant when the delivery member is wrapped around the implant to form a conforming cavity around the implant.

Statement 21: The device according to any one of the preceding Statements 1-20, wherein the delivery member is operable to receive an implant by placing the implant on an upper surface of the delivery member and wrapping the delivery member around the implant to form a conforming cavity around the implant.

Statement 22: The device according to any one of the preceding Statements 1-21, wherein the delivery member is operable to pick up an implant from a bowl or surface without touching the implant, thereby receiving the implant into the delivery member and forming a conforming cavity around the implant.

Statement 23: The device according to any one of the preceding Statements 1-22, wherein the delivery member comprises a diameter that is at least three times greater than the cross-sectional width of the inner bore of the shielding member.

Statement 24: The device according to any one of the preceding Statements 1-22, wherein the delivery member comprises a diameter that is more than three times greater than the cross-sectional width of the inner bore of the shielding member.

Statement 25: The device according to any one of the preceding Statements 1-22, wherein the delivery member comprises a diameter that is at least five times greater than the cross-sectional width of the inner bore of the shielding member.

Statement 26: The device according to any one of the preceding Statements 1-22, wherein the delivery member comprises a diameter that is more than five times greater than the cross-sectional width of the inner bore of the shielding member.

Statement 27: The device according to any one of the preceding Statements 1-22, wherein the base comprises a diameter that is from about five (5) to about eight (8) times greater than the cross-sectional width of the inner bore of the shielding member.

Statement 28: The device according to any one of the preceding Statements 1-22, wherein the base comprises a diameter that is from about six (6) to about eight (8) times greater than the cross-sectional width of the inner bore of the shielding member.

Statement 29: The device according to any one of the preceding Statements 1-28, wherein the cross-sectional width of the inner bore is from about 3.5 cm to about 8 cm.

Statement 30: The device according to any one of the preceding Statements 1-28, wherein the cross-sectional width of the inner bore is from about 2 cm to about 10 cm.

Statement 31: The device according to any one of the preceding Statements 1-30, wherein the diameter of the delivery member is from about 17.5 cm to about 40 cm.

Statement 32: The device according to any one of the preceding Statements 1-30, wherein the diameter of the delivery member is from about 10 cm to about 50 cm.

Statement 33: The device according to any one of the preceding Statements 1-30, wherein the diameter of the delivery member is from about 21 cm to about 48 cm.

Statement 34: The device according to any one of the preceding Statements 1-30, wherein the diameter of the delivery member is from about 12 cm to about 60 cm.

Statement 35: The device according to any one of the preceding Statements 1-30, wherein the diameter of the delivery member is from about 24.5 cm to about 56 cm.

Statement 36: The device according to any one of the preceding Statements 1-30, wherein the diameter of the delivery member is from about 14 cm to about 70 cm.

Statement 37: The device according to any one of the preceding Statements 1-30, wherein the diameter of the delivery member is from about 28 cm to about 64 cm.

Statement 38: The device according to any one of the preceding Statements 1-30, wherein the diameter of the delivery member is from about 16 cm to about 80 cm.

Statement 39: The device according to any one of the preceding Statements 1-30, wherein the diameter of the delivery member is from about 35 cm to about 80 cm.

Statement 40: The device according to any one of the preceding Statements 1-30, wherein the diameter of the delivery member is from about 20 cm to about 100 cm.

Statement 41: The device according to any one of the preceding Statements 1-40, wherein the shielding member and base are formed from a flexible material.

Statement 42: The device according to Statement 41, wherein the flexible material is selected from the group consisting of plastic-containing fabrics, polymers, plastics, ethylene-vinyl acetate (EVA), polyethylene terephthalate, vinyls, polyvinyl chloride, ethylene and alpha-olefin copolymers, silicone, solid silicone, silicone rubber, and any combination thereof.

Statement 43: The device according to any one of the preceding Statements 1-42, wherein the delivery member is formed from a vinyl or polyvinyl chloride.

Statement 44: The device according to any one of the preceding Statements 1-43, wherein the shielding member is formed from elastomeric silicone or silicone rubber.

Statement 45: The device according to any one of the preceding Statements 1-44, wherein the joint or intersection between the delivery member and the shielding member is heat sealed.

Statement 46: The device according to any one of the preceding Statements 1-45, wherein the delivery member and the shielding member are formed from different materials.

Statement 47: The device according to any one of the preceding Statements 1-46, wherein the delivery member is formed from a material that is fairly inelastic to mildly elastic.

Statement 48: The device according to any one of the preceding Statements 1-47, wherein the shielding member is formed from a material that is slightly stretchable to elastic.

Statement 49: The device according to any one of the preceding Statements 1-48, wherein the inner bore is conical or frustoconical.

Statement 50: The device according to any one of the preceding Statements 1-49, wherein the shielding member comprises a conical member.

Statement 51: The device according to any one of the preceding Statements 1-50, wherein the inner bore has a larger cross-sectional width at the proximal end than the cross-sectional width of the inner bore at the distal end of the shielding member.

Statement 52: The device according to any one of the preceding Statements 1-50, wherein the inner bore comprises a conical portion and a tubular portion along its predetermined length.

Statement 53: The device according to any one of the preceding Statements 1-52, wherein the shielding member comprises a conical member and a tubular member.

Statement 54: The device according to Statement 53, wherein the conical member has an inner bore, a distal end, and a proximal end, and the tubular member has an inner bore, a distal end and a proximal end, wherein the proximal end of the conical member is coupled with the lower surface of the delivery member such that the inner bore of the conical member is substantially aligned with the aperture of the delivery member so that the conical member may receive the implant once the implant is inserted into the aperture.

Statement 55: The device according to Statement 54, wherein the distal end of the conical member is coupled with the proximal end of the tubular member such that the inner bore of the conical member is substantially aligned with the inner bore of the tubular member to form the inner bore of the shielding member.

Statement 56: The device according to Statement 55, wherein the tubular member has a first predetermined length and the conical member has a second predetermined length, the predetermined length of the shielding member comprising the sum of the first and second predetermined lengths.

Statement 57: The device according to any one of the preceding Statements 1-56, wherein the shielding member comprises an aperture formed in the distal end of the shielding member.

Statement 58: The device according to any one of the preceding Statements 1-57, wherein the shielding member comprises an outer surface, the outer surface defining an outer bore, wherein the outer bore is substantially tubular and the inner bore is substantially frustoconical.

Statement 59: The device according to any one of the preceding Statements 1-57, wherein the shielding member comprises an outer surface, the outer surface defining an outer bore, wherein the outer bore comprises a cross-sectional width that is substantially tubular and the inner bore comprises a cross-sectional width that is substantially frustoconical.

Statement 60: The device according to any one of the preceding Statements 1-57, wherein the shielding member comprises an outer surface, the outer surface defining an outer bore, wherein the outer bore is substantially tubular and the inner bore comprises a tubular portion and a conical portion.

Statement 61: The device according to Statement 60, wherein the tubular portion of the inner bore comprises a substantially uniform cross-sectional width and the conical portion of the inner bore comprises a larger cross-sectional width that is larger at the proximal end of the shielding member and decreases towards the distal end of the shielding member.

Statement 62: The device according to any one of the preceding Statements 1-57, wherein the inner bore has a substantially uniform cross-sectional width over the predetermined length.

Statement 63: The device according to any one of the preceding Statements 1-62, further comprising: a base having an upper surface and a lower surface, the base having an aperture formed therein and extending through the upper surface and the lower surface; wherein the base is coupled to the proximal end of the shielding member such that the proximal end of the inner bore of the shielding member is substantially aligned with the aperture formed in the base; wherein the aperture formed in the base is also co-aligned with the aperture formed in the delivery member thereby forming a collective aperture through which the implant may pass when mechanical force is applied to the delivery member; and wherein the lower surface of the base is operable to engage with a skin of the subject.

Statement 64: The device according to Statement 63, wherein an adhesive is disposed on the lower surface of the base.

Statement 65: The device according to any one of the preceding Statements 1-64, wherein the predetermined length is greater than 1 cm.

Statement 66: The device according to any one of the preceding Statements 1-64, wherein the predetermined length is from about 2 cm to about 10 cm.

Statement 67: The device according to any one of the preceding Statements 1-66, wherein the delivery member extends away from the shielding member in substantially the same plane as the aperture of the delivery member.

Statement 68: A method for delivering an implant into a surgically-created implant pocket in a subject through a dissection tunnel connecting the implant pocket to an incision on the skin of the subject, the method comprising: providing a sterile implant delivery device, the implant delivery device comprising: a delivery member having an upper surface and a lower surface, the delivery member having an aperture formed therein and extending through the upper surface and the lower surface; and a shielding member coupled with the delivery member, the shielding member having an inner bore extending longitudinally between a proximal end having a proximal opening and a distal end having a distal opening, the inner bore extending a predetermined length away from the lower surface of the delivery member; wherein the proximal end of the shielding member is coupled with the delivery member and the inner bore is substantially aligned with the aperture formed in the delivery member; causing the delivery member to wrap around the implant to form a conforming cavity around the implant that conforms to the shape of the implant; inserting, while the implant is disposed within the conforming cavity formed by the delivery member, the distal end of the shielding member of the implant delivery device through the incision in the skin of subject and into the dissection tunnel such that the distal end of the shielding member is received in at least a portion of the dissection tunnel; and causing, by the application of mechanical force to the lower surface of the delivery member, the implant to translate from the conforming cavity through the aperture formed in the delivery member and into the inner bore of the shielding member and into the implant pocket in the subject.

Statement 69: The method according to Statement 68, wherein the application of mechanical force to the lower surface of the delivery member propels the implant from the conforming cavity formed in the delivery member through the aperture formed in the delivery member and through the inner bore and distal end of the shielding member so as to deliver the implant into the implant pocket in the subject.

Statement 70: The method according to Statement 68 or Statement 69, further comprising: measuring a length of a dissection tunnel connecting the implant pocket to an incision on a skin of the subject; and adjusting the predetermined length of the inner bore of the shielding member such that it is greater than 1 cm but equal to or less than the measured length of the dissection tunnel.

Statement 71: The method according to any one of the preceding Statements 68-70, further comprising: inserting the distal end of the shielding member into the dissection tunnel at least 1.5 cm below the incision.

Statement 72: The method according to any one of the preceding Statements 68-71, further comprising: placing the implant on the upper surface of the delivery member; and wrapping the delivery member around the implant to form a conforming cavity with the implant disposed therein.

Statement 73: The method according to any one of the preceding Statements 68-72, further comprising: providing the implant in a bowl; picking up the implant from the bowl using the upper surface of the delivery member such that the implant is contained by the upper surface of the delivery member; and wrapping the delivery member around the implant to form a conforming cavity with the implant disposed therein and in contact with the upper surface of the delivery member.

Statement 74: The method according to any one of the preceding Statements 68-73, wherein the conforming cavity is formed by the upper surface of the delivery member in contact with the implant.

Statement 75: The method according to any one of the preceding Statements 68-74, wherein the delivery member comprises a plurality of lengths defining the outer edge of the delivery member, each of the lengths comprising a radius of curvature.

Statement 76: The method according to Statement 75, wherein the radius of curvature comprises a curve or a segment of a circle or an ellipse.

Statement 77: The method according to Statement 76, wherein each of the plurality of lengths intersects an adjacent length at a vertex, the radius of curvature beginning and ending at one of the verteces and extending along the entire length of each of the plurality of lengths.

Statement 78: The method according to Statement 76, wherein each of the plurality of lengths intersects an adjacent length at a vertex, the radius of curvature beginning and ending along the length at a predetermined distance from the vertex.

Statement 79: The method according to any one of the preceding Statements 68-78, wherein the delivery member is substantially rectangular and comprises four lengths defining the outer edge of the delivery member.

Statement 80: The method according to Statement 79, wherein each of the four lengths comprises a radius of curvature.

Statement 81: The method according to Statement 80, wherein the radius of curvature comprises a curve or a segment of a circle or an ellipse.

Statement 82: The method according to Statement 81, wherein each of the four lengths intersects an adjacent length at a vertex, the radius of curvature beginning and ending at each of the vertices and extending along the entire length of each of the plurality of lengths.

Statement 83: The method according to Statement 81, wherein each of the four lengths intersects an adjacent length at a vertex, the radius of curvature beginning and ending along each of the four lengths at a predetermined distance from the vertex.

Statement 84: The method according to any one of the preceding Statements 79-93, wherein each of the four lengths are equal in length.

Statement 85: The method according to any one of the preceding Statements 68-84, wherein the proximal end of the shielding member is coupled with the lower surface of the delivery member.

Statement 86: The method according to any one of the preceding Statements 68-85, wherein the delivery member is operable to receive any size implant in common use.

Statement 87: The method according to any one of the preceding Statements 68-86, wherein the delivery member does not comprise an aperture for receiving the implant into the delivery device.

Statement 88: The method according to any one of the preceding Statements 68-86, wherein the delivery member does not comprise an aperture through which an implant may be loaded into the delivery device.

Statement 89: The method according to any one of the preceding Statements 68-88, wherein the delivery member does not comprise a preformed conforming cavity.

Statement 90: The method according to any one of the preceding Statements 68-89, wherein the delivery member is operable to conform to the dimensions of the implant when the delivery member is wrapped around the implant to form a conforming cavity around the implant.

Statement 91: The method according to any one of the preceding Statements 68-90, wherein the delivery member is operable to receive an implant by placing the implant on an upper surface of the delivery member and wrapping the delivery member around the implant to form a conforming cavity around the implant.

Statement 92: The method according to any one of the preceding Statements 68-91, wherein the delivery member is operable to pick up an implant from a bowl or surface without touching the implant, thereby receiving the implant into the delivery member and forming a conforming cavity around the implant.

Statement 93: The method according to any one of the preceding Statements 68-92, wherein the delivery member comprises a diameter that is at least three times greater than the cross-sectional width of the inner bore of the shielding member.

Statement 94: The method according to any one of the preceding Statements 68-92, wherein the delivery member comprises a diameter that is more than three times greater than the cross-sectional width of the inner bore of the shielding member.

Statement 95: The method according to any one of the preceding Statements 68-92, wherein the delivery member comprises a diameter that is at least five times greater than the cross-sectional width of the inner bore of the shielding member.

Statement 96: The method according to any one of the preceding Statements 68-92, wherein the delivery member comprises a diameter that is more than five times greater than the cross-sectional width of the inner bore of the shielding member.

Statement 97: The method according to any one of the preceding Statements 68-92, wherein the base comprises a diameter that is from about five (5) to about eight (8) times greater than the cross-sectional width of the inner bore of the shielding member.

Statement 98: The method according to any one of the preceding Statements 68-92, wherein the base comprises a diameter that is from about six (6) to about eight (8) times greater than the cross-sectional width of the inner bore of the shielding member.

Statement 99: The method according to any one of the preceding Statements 68-98, wherein the cross-sectional width of the inner bore is from about 3.5 cm to about 8 cm.

Statement 100: The method according to any one of the preceding Statements 68-98, wherein the cross-sectional width of the inner bore is from about 2 cm to about 10 cm.

Statement 101: The method according to any one of the preceding Statements 68-100, wherein the diameter of the delivery member is from about 17.5 cm to about 40 cm.

Statement 102: The method according to any one of the preceding Statements 68-100, wherein the diameter of the delivery member is from about 10 cm to about 50 cm.

Statement 103: The method according to any one of the preceding Statements 68-100, wherein the diameter of the delivery member is from about 21 cm to about 48 cm.

Statement 104: The method according to any one of the preceding Statements 68-100, wherein the diameter of the delivery member is from about 12 cm to about 60 cm.

Statement 105: The method according to any one of the preceding Statements 68-100, wherein the diameter of the delivery member is from about 24.5 cm to about 56 cm.

Statement 106: The method according to any one of the preceding Statements 68-100, wherein the diameter of the delivery member is from about 14 cm to about 70 cm.

Statement 107: The method according to any one of the preceding Statements 68-100, wherein the diameter of the delivery member is from about 28 cm to about 64 cm.

Statement 108: The method according to any one of the preceding Statements 68-100, wherein the diameter of the delivery member is from about 16 cm to about 80 cm.

Statement 109: The method according to any one of the preceding Statements 68-100, wherein the diameter of the delivery member is from about 35 cm to about 80 cm.

Statement 110: The method according to any one of the preceding Statements 68-100, wherein the diameter of the delivery member is from about 20 cm to about 100 cm.

Statement 111: The method according to any one of the preceding Statements 68-110, wherein the shielding member and base are formed from a flexible material.

Statement 112: The method according to Statement 111, wherein the flexible material is selected from the group consisting of plastic-containing fabrics, polymers, plastics, ethylene-vinyl acetate (EVA), polyethylene terephthalate, vinyls, polyvinyl chloride, ethylene and alpha-olefin copolymers, silicone, solid silicone, silicone rubber, and any combination thereof.

Statement 113: The method according to any one of the preceding Statements 68-112, wherein the delivery member is formed from a vinyl or polyvinyl chloride.

Statement 114: The method according to any one of the preceding Statements 68-113, wherein the shielding member is formed from elastomeric silicone or silicone rubber.

Statement 115: The method according to any one of the preceding Statements 68-114, wherein the joint or intersection between the delivery member and the shielding member is heat sealed.

Statement 116: The method according to any one of the preceding Statements 68-115, wherein the delivery member and the shielding member are formed from different materials.

Statement 117: The method according to any one of the preceding Statements 68-116, wherein the delivery member is formed from a material that is fairly inelastic to mildly elastic.

Statement 118: The method according to any one of the preceding Statements 68-117, wherein the shielding member is formed from a material that is slightly stretchable to elastic.

Statement 119: The method according to any one of the preceding Statements 68-118, wherein the inner bore is conical or frustoconical.

Statement 120: The method according to any one of the preceding Statements 68-119, wherein the shielding member comprises a conical member.

Statement 121: The method according to any one of the preceding Statements 68-120, wherein the inner bore has a larger cross-sectional width at the proximal end than the cross-sectional width of the inner bore at the distal end of the shielding member.

Statement 122: The method according to any one of the preceding Statements 68-120, wherein the inner bore comprises a conical portion and a tubular portion along its predetermined length.

Statement 123: The method according to any one of the preceding Statements 68-122, wherein the shielding member comprises a conical member and a tubular member.

Statement 124: The method according to Statement 123, wherein the conical member has an inner bore, a distal end, and a proximal end, and the tubular member has an inner bore, a distal end and a proximal end, wherein the proximal end of the conical member is coupled with the lower surface of the delivery member such that the inner bore of the conical member is substantially aligned with the aperture of the delivery member so that the conical member may receive the implant once the implant is inserted into the aperture.

Statement 125: The method according to Statement 124, wherein the distal end of the conical member is coupled with the proximal end of the tubular member such that the inner bore of the conical member is substantially aligned with the inner bore of the tubular member to form the inner bore of the shielding member.

Statement 126: The method according to Statement 125, wherein the tubular member has a first predetermined length and the conical member has a second predetermined length, the predetermined length of the shielding member comprising the sum of the first and second predetermined lengths.

Statement 127: The method according to any one of the preceding Statements 68-126, wherein the shielding member comprises an aperture formed in the distal end of the shielding member.

Statement 128: The method according to any one of the preceding Statements 68-127, wherein the shielding member comprises an outer surface, the outer surface defining an outer bore, wherein the outer bore is substantially tubular and the inner bore is substantially frustoconical.

Statement 129: The method according to any one of the preceding Statements 68-127, wherein the shielding member comprises an outer surface, the outer surface defining an outer bore, wherein the outer bore comprises a cross-sectional width that is substantially tubular and the inner bore comprises a cross-sectional width that is substantially frustoconical.

Statement 130: The method according to any one of the preceding Statements 68-127, wherein the shielding member comprises an outer surface, the outer surface defining an outer bore, wherein the outer bore is substantially tubular and the inner bore comprises a tubular portion and a conical portion.

Statement 131: The method according to Statement 130, wherein the tubular portion of the inner bore comprises a substantially uniform cross-sectional width and the conical portion of the inner bore comprises a larger cross-sectional width that is larger at the proximal end of the shielding member and decreases towards the distal end of the shielding member.

Statement 132: The method according to any one of the preceding Statements 68-127, wherein the inner bore has a substantially uniform cross-sectional width over the predetermined length.

Statement 133: The method according to any one of the preceding Statements 68-132, wherein the predetermined length is greater than 1 cm.

Statement 134: The method according to any one of the preceding Statements 68-132, wherein the predetermined length is from about 2 cm to about 10 cm.

Statement 135: The method according to any one of the preceding Statements 68-134, wherein the delivery member extends away from the shielding member in substantially the same plane as the aperture of the delivery member.

Statement 136: The method according to any one of the preceding Statements 68-135, wherein the implant delivery device further comprises: a base having an upper surface and a lower surface, the base having an aperture formed therein and extending through the upper surface and the lower surface.

Statement 137: The method according to Statement 136, wherein the base is coupled to the proximal end of the shielding member such that the proximal end of the inner bore of the shielding member is substantially aligned with the aperture formed in the base.

Statement 138: The method according to Statement 137, wherein the aperture formed in the base is also co-aligned with the aperture formed in the delivery member thereby forming a collective aperture through which the implant may pass when mechanical force is applied to the delivery member.

Statement 139: The method according to Statement 138, wherein the lower surface of the base is operable to engage with a skin of the subject.

Statement 140: The method according to any one of the preceding Statements 136-139, further comprising: causing the lower surface of the base to substantially engage with at least a portion of the skin adjacent to an incision leading to the implant pocket.

Statement 141: The method according to any one of the preceding Statements 136-139, further comprising: inserting the shielding member of the implant delivery device into a portion of a dissection tunnel connecting the implant pocket to an incision on a skin of the subject, such that the lower surface of the base substantially engages with at least a portion of the skin adjacent to the incision; and inserting the distal end of the shielding member into the dissection tunnel at least 1.5 cm below the incision.

Statement 142: The method according to Statement 140 or Statement 141, wherein the lower surface of the base is operable to engage a skin of the subject so that the distal end of the shielding member remains secured and disposed in a portion of a dissection tunnel connecting the implant pocket to an incision in the skin of the subject during delivery of the implant into the implant pocket.

Statement 143: The method according to any one of the preceding Statements 68-142, further comprising: providing an implant on a sterile surface; and engaging the implant with the implant delivery device in order to load the implant delivery device with the implant such that the implant is disposed in a conforming cavity formed by the delivery member of the implant delivery device, wherein engaging the implant comprises contacting the implant with the upper surface of the delivery member so as to be picked up or translated from the surface with the implant only in contact with the upper surface of the delivery member.

Statement 144: The method according to Statement 143, further comprising causing the delivery member to wrap around the implant to form a conforming cavity around the implant that conforms to the shape of the implant.

Statement 145: The method according to Statement 143 or Statement 144, wherein the surface is a curved surface.

Statement 146: The method according to any one of the preceding Statements 143-145, wherein the surface is a sterile bowl.

Statement 147: The method according to any one of the preceding Statements 68-142, further comprising placing the implant on the upper surface of the delivery member.

Statement 148: The method according to any one of the preceding Statements 68-142, further comprising: placing the implant delivery device on a sterile curved surface with the upper surface of the delivery member facing upwards so as to be operable to receive the implant thereon, wherein the lower surface of the delivery member is in contact with the sterile curved surface; and placing the implant on the upper surface of the delivery member while the delivery member and the implant delivery device are disposed about the sterile curved surface.

Statement 149: The method according to Statement 148, wherein the curved surface is a sterile bowl.

Statement 150: The method according to any one of the preceding Statements 147-149, wherein placing the implant on the upper surface of the delivery member comprises pouring the implant from a sterile bowl onto the upper surface of the delivery member.

Statement 151: The method according to any one of the preceding Statements 68-142, further comprising: providing the implant in a sterile bowl; and pouring the implant from the sterile bowl onto the upper surface of the delivery member.

Statement 152: The method according to any one of the preceding Statements 68-142, further comprising: providing the implant in a sterile bowl; providing the implant delivery device in sterile bowl with the upper surface of the delivery member facing upwards so as to be operable to receive the implant thereon; and pouring the implant from the sterile bowl onto the upper surface of the delivery member while the delivery member and the implant delivery device is disposed in the sterile bowl.

Statement 153: The method according to any one of the preceding Statements 68-142, further comprising: providing the implant delivery device in a sterile curved surface with the upper surface of the delivery member facing upwards so as to be operable to receive the implant thereon, wherein the lower surface of the delivery member is in contact with the sterile curved surface; and placing the implant on the upper surface of the delivery member while the delivery member and the implant delivery device are disposed about the sterile curved surface.

Statement 154: The method according to Statement 153, wherein the curved surface is a sterile bowl.

Statement 155: The method according to Statement 153 or Statement 154, wherein placing the implant on the upper surface of the delivery member comprises pouring the implant from a sterile bowl onto the upper surface of the delivery member.

Statement 156: The method according to any one of the preceding Statements 68-155, wherein causing the implant to translate from the conforming cavity comprises applying a compressive force to the lower surface between the proximal end of the delivery member and the conforming cavity.

Statement 157: The method according to any one of the preceding Statements 68-155, wherein causing the implant to translate from the conforming cavity comprises applying a compressive force to a portion of the conforming cavity nearest the proximal end of delivery member.

Statement 158: The method according to any one of the preceding Statements 68-155, wherein causing the implant to translate from the conforming cavity comprises sliding a user's hand from the proximal end of the delivery member towards the distal end of the delivery member such that compressive force is imparted to the conforming cavity and/or the implant disposed within the conforming cavity, thereby causing the implant to be propelled from the conforming cavity to the inner bore of the shielding member and into the implant pocket in the subject.

Statement 159: The method according to any one of the preceding Statements 68-155, wherein causing the implant to translate from the conforming cavity comprises twisting the proximal end of the delivery member until sufficient compressive force is exerted on the conforming cavity and/or the implant disposed within the conforming cavity, such that the implant is propelled from the conforming cavity into the inner bore of the shielding member and into the implant pocket in the subject.

Statement 160: The device according to any one of the preceding Statements 1-67, wherein the aperture is operable to receive the breast implant therethrough when mechanical force is applied to the lower surface of the delivery member, the inner bore being operable to receive the implant therethrough via the aperture.

Statement 161: The method according to any one of the preceding Statements 68-159, wherein the aperture is operable to receive the breast implant therethrough when mechanical force is applied to the lower surface of the delivery member, the inner bore being operable to receive the implant therethrough via the aperture.

Statement 162: A method for delivering an implant into a surgically-created implant pocket in a subject through a dissection tunnel connecting the implant pocket to an incision on the skin of the subject, the method comprising: providing a first sterile implant delivery device according to any one of the preceding Statements 1-67 and 160, and a second sterile implant delivery device according to any one of the preceding Statements 1-67 and 160; using the first implant delivery device as a biofilm implant shield by inserting the shielding member into the incision and dissection tunnel to a depth greater than 1 cm below the incision and allowing the lower surface of the delivery member to engage the skin of the subject adjacent to the incision or otherwise lay flat against the skin of the subject; causing the delivery member of the second implant delivery device to wrap around the implant to form a conforming cavity around the implant that conforms to the shape of the implant; inserting, while the implant is disposed within the conforming cavity formed by the delivery member, the distal end of the shielding member of the second implant delivery device into the aperture of the first implant delivery device such that the distal end of the shielding member of the second implant delivery device is received in at least a portion of the inner bore of the first implant delivery device; and causing, by the application of mechanical force to the lower surface of the delivery member of the second implant delivery device, the implant to translate from the conforming cavity through the aperture formed in the delivery member and into the inner bore of the shielding member of the second implant delivery device and into aperture and shielding member of the first implant delivery device, thereby providing for sterile delivery of the implant to the implant pocket in the subject.

What is claimed is:

1. A device for delivering an implant into a surgically-created implant pocket in a subject, the device comprising:
   a delivery member having an upper surface and a lower surface, the delivery member having an aperture formed therein and extending through the upper surface and the lower surface; and
   a shielding member coupled with the delivery member, the shielding member having an inner bore extending longitudinally between a proximal end having a proximal opening and a distal end having a distal opening, the inner bore extending a predetermined length away from the lower surface of the delivery member;
   wherein the proximal end of the shielding member is coupled with the delivery member and the inner bore is substantially aligned with the aperture formed in the delivery member;
   wherein the delivery member extends away from the shielding member in substantially the same plane as the aperture of the delivery member and the proximal opening of the shielding member;
   wherein the delivery member is operable to wrap around the implant to form a conforming cavity around the implant that conforms to the shape of the implant; and
   wherein the inner bore is operable to receive the implant therethrough when mechanical force is applied to the lower surface of the delivery member.

2. The device according to claim 1, wherein the aperture is operable to receive the implant therethrough when mechanical force is applied to the lower surface of the delivery member, the inner bore being operable to receive the implant therethrough via the aperture.

3. The device according to claim 1, wherein the delivery member is operable to propel the implant from the conforming cavity through the aperture formed in the delivery member and into the inner bore of the shielding member upon the application of mechanical force to the lower surface of the delivery member.

4. The device according to claim 1, wherein the delivery member is operable to propel the implant from the conforming cavity into the implant pocket in the subject upon the application of mechanical force to the lower surface of the delivery member.

5. The device according to claim 1, wherein the delivery member comprises a diameter that is at least three times greater than the cross-sectional width of the inner bore of the shielding member.

6. The device according to claim 1, wherein the delivery member comprises a diameter that is at least five times greater than the cross-sectional width of the inner bore of the shielding member.

7. The device according to claim 1, wherein the delivery member comprises a plurality of lengths defining the outer edge of the delivery member, each of the lengths comprising a radius of curvature.

8. The device according to claim 7, wherein each of the plurality of lengths intersects an adjacent length at a vertex, the radius of curvature beginning and ending at one of the verteces and extending along the entire length of each of the plurality of lengths.

9. The device according to claim 7, wherein each of the plurality of lengths intersects an adjacent length at a vertex, the radius of curvature beginning and ending along the length at a predetermined distance from the vertex.

10. The device according to claim 1, wherein the delivery member and the shielding member are formed from a flexible material.

11. The device according to claim 10, wherein the flexible material is selected from the group consisting of plastic-containing fabrics, polymers, plastics, ethylene-vinyl acetate (EVA), polyethylene terephthalate, vinyls, polyvinyl chloride, ethylene and alpha-olefin copolymers, silicone, solid silicone, silicone rubber, and any combination thereof.

12. The device according to claim 1, wherein the inner bore has a substantially uniform cross-sectional width over the predetermined length.

13. The device according to claim 1, further comprising:
a base having an upper surface and a lower surface, the base having an aperture formed therein and extending through the upper surface and the lower surface;
wherein the base is coupled to the proximal end of the shielding member such that the proximal end of the inner bore of the shielding member is substantially aligned with the aperture formed in the base;
wherein the aperture formed in the base is also co-aligned with the aperture formed in the delivery member thereby forming a collective aperture through which the implant may pass when mechanical force is applied to the delivery member; and
wherein the lower surface of the base is operable to engage with a skin of the subject.

14. A method for delivering an implant into a surgically-created implant pocket in a subject through a dissection tunnel connecting the implant pocket to an incision on the skin of the subject, the method comprising:
providing a sterile implant delivery device, the implant delivery device comprising:
a delivery member having an upper surface and a lower surface, the delivery member having an aperture formed therein and extending through the upper surface and the lower surface; and
a shielding member coupled with the delivery member, the shielding member having an inner bore extending longitudinally between a proximal end having a proximal opening and a distal end having a distal opening, the inner bore extending a predetermined length away from the lower surface of the delivery member;
wherein the proximal end of the shielding member is coupled with the delivery member and the inner bore is substantially aligned with the aperture formed in the delivery member;
wherein the delivery member extends away from the shielding member in substantially the same plane as the aperture of the delivery member and the proximal opening of the shielding member;
causing the delivery member to wrap around the implant to form a conforming cavity around the implant that conforms to the shape of the implant;
inserting, while the implant is disposed within the conforming cavity formed by the delivery member, the distal end of the shielding member of the implant delivery device through the incision in the skin of subject and into the dissection tunnel such that the distal end of the shielding member is received in at least a portion of the dissection tunnel; and
causing, by the application of mechanical force to the lower surface of the delivery member, the implant to translate from the conforming cavity through the aperture formed in the delivery member and into the inner bore of the shielding member and into the implant pocket in the subject.

15. The method according to claim 14, further comprising: inserting the distal end of the shielding member into the dissection tunnel at least 1.5 cm below the incision.

16. The method according to claim 14, further comprising:
measuring a length of a dissection tunnel connecting the implant pocket to an incision on a skin of the subject; and
adjusting the predetermined length of the inner bore of the shielding member such that it is greater than 1 cm but equal to or less than the measured length of the dissection tunnel.

17. The method according to claim 14, further comprising:
placing the implant on the upper surface of the delivery member; and
wrapping the delivery member around the implant to form a conforming cavity with the implant disposed therein.

18. The method according to claim 14, further comprising:
providing the implant in a bowl;
picking up the implant from the bowl using the upper surface of the delivery member such that the implant is contained by the upper surface of the delivery member; and
wrapping the delivery member around the implant to form a conforming cavity with the implant disposed therein and in contact with the upper surface of the delivery member.

19. The method according to claim 14, further comprising:
providing an implant on a sterile surface; and
engaging the implant with the implant delivery device in order to load the implant delivery device with the implant such that the implant is disposed in a conforming cavity formed by the delivery member of the implant delivery device, wherein engaging the implant comprises contacting the implant with the upper surface of the delivery member so as to be picked up or translated from the surface with the implant only in contact with the upper surface of the delivery member.

20. The method according to claim 14, further comprising:
providing the implant in a sterile bowl; and
pouring the implant from the sterile bowl onto the upper surface of the delivery member.

\* \* \* \* \*